US010746735B2

(12) United States Patent
Lüking et al.

(10) Patent No.: US 10,746,735 B2
(45) Date of Patent: Aug. 18, 2020

(54) MARKER SEQUENCES FOR DIAGNOSING AND STRATIFYING SLE PATIENTS

(71) Applicant: PROTAGEN AG, Dortmund (DE)

(72) Inventors: Angelika Lüking, Bochum (DE); Peter Schulz-Knappe, Hemmingen (DE); Carmen Theek, Herdecke (DE); Petra Budde, Dortmund (DE); Anna Telaar, Dortmund (DE)

(73) Assignee: Oncimmune Germany GmbH, Dortmund (DE)

( * ) Notice: Subject to any disclaimer, the term of this patent is extended or adjusted under 35 U.S.C. 154(b) by 198 days.

(21) Appl. No.: 15/117,508

(22) PCT Filed: Feb. 10, 2015

(86) PCT No.: PCT/EP2015/052805
§ 371 (c)(1),
(2) Date: Aug. 9, 2016

(87) PCT Pub. No.: WO2015/118184
PCT Pub. Date: Aug. 13, 2015

(65) Prior Publication Data
US 2017/0074875 A1 Mar. 16, 2017

(30) Foreign Application Priority Data

Feb. 10, 2014 (EP) .................................... 14154557
Jul. 22, 2014 (EP) .................................... 14178090

(51) Int. Cl.
*G01N 33/564* (2006.01)

(52) U.S. Cl.
CPC ....... *G01N 33/564* (2013.01); *G01N 2500/04* (2013.01); *G01N 2800/104* (2013.01); *G01N 2800/52* (2013.01)

(58) Field of Classification Search
None
See application file for complete search history.

(56) References Cited

U.S. PATENT DOCUMENTS

2013/0303395 A1   11/2013   Lueking et al.

FOREIGN PATENT DOCUMENTS

| EP | 2 441 848 A1 | 4/2012 |
|---|---|---|
| WO | WO-99/57311 A2 | 11/1999 |
| WO | WO-99/57312 A1 | 11/1999 |
| WO | WO-2008/109030 A2 | 9/2008 |
| WO | WO-2012/049225 A2 | 4/2012 |
| WO | WO-2014/020357 A1 | 2/2014 |

OTHER PUBLICATIONS

AKO57299 Deposit information (Year: 2008).*
Collins et al. Pro Natl. Acad. Sci. USA 2002 vol. 99, p. 16899-16903 (Year: 2002).*
Ota et al. (Nat. Genet. 2004 vol. 36, p. 40-45) (Year: 2004).*
Vanarsa F1000 Medicine Reports vol. 2, p. 87; total 5 pages (Year: 2010).*
Kuno J Biol. Chem ; 1993, vol. 268, p. 13510-13518 (Year: 1993).*
Ashmun Blood 1992, vol. 79, page 3344-3349 (Year: 1992).*
Green Pro. Natl. Acad. Sci. 1999 vol. 96, p. 4176-4179 (Year: 1999).*
Erlenbach J. Biol. Chem 2001 vol. 276, p. 29382-39392 (Year: 2001).*
Noutoshi The Plant Journal ; 2005 vol. 43, p. 873-888 (Year: 2005).*
Bowie Science, 1990 vol. 247:1306-1310 (Year: 1990).*
Kataoka et al. (Biochim Biophys Acta 1991 vol. 1089, 393-395) (Year: 1991).*
Godbout et al. (Gene 123 (2), 195-201 (1993)) (Year: 1993).*
Budde, P., et al., "Diagnostic Autoantibody Signatures of Rheumatoid Arthritis Patients Identified with A Bead-Based Assay Approach", Database Biosis Accession No. PREV201300781846, Abstract No. AB0746, 2013.
Budde, P., et al., "Identification of Novel Distinct Autoantigen Clusters Reflecting the Heterogeneity of Systemic Lupus Erythematosus", Database Biosis Accession No. PREV201300782499, Abstract No. 1575, 2013.
Carlsson, A., et al., "Serum Protein Profiling of Systemic Lupus Erythematosus and Systemic Sclerosis Using Recombinant Antibody Microarrays", Molecular & Cellular Proteomics, 2011, vol. 10, No. 5, 10.1074/mcp.M110.005033-13, 14 pages.
Ching, K. H., et al., "Two Major Autoantibody Clusters in Systemic Lupus Erythematosus", PLoS One, 2012, vol. 7, Issue 2, p. e32001, 11 pages.
Gutjahr,m C., et al., "Mouse Protein Arrays from a $T_H1$ Cell cDNA Library for Antibody Screening and Serum Profiling", Genomics, 2005, vol. 85, pp. 285-296.
Liu, C.-C., et al., "Biomarkers in Systemic Lupus Erythematosus: Challenges and Prospects for the Future", Therapeutic Advances in Musculoskeletal Disease, 2013, vol. 5, No. 4, pp. 210-233.
Lueking, A., et al., "Autoantibody Signatures of Systemic Lupus Erythematosus (SLE) Patients Identified with a Bead-Based Assay Approach", Database Biosis Accession No. PREV201400263908, 2014, Abstract No. [2013][FRI0473] (Published in Ann. Rheum. Dis., 2013, vol. 72(Suppl3), p. 535).

(Continued)

*Primary Examiner* — Changhwa J Cheu
(74) *Attorney, Agent, or Firm* — Finnegan, Henderson, Farabow, Garrett and Dunner, LLP

(57) ABSTRACT

The present invention relates to methods for identifying markers for systemic lupus erythematosus (SLE) and to the markers identified with the aid of this method, which can differentiate between SLE and other autoimmune diseases on the one hand and between different SLE subgroups on the other hand. The invention also relates to panels, diagnostic devices and test kits which comprise these markers, and to the use and application thereof, for example for the diagnosis, prognosis and therapy control in SLE. The invention also relates to methods for screening and validating active substances for application in SLE subgroups.

4 Claims, 13 Drawing Sheets
Specification includes a Sequence Listing.

(56) References Cited

OTHER PUBLICATIONS

Mattoon, D., et al., "Sa.27. Discovery of SLE Autoantibody Biomarkers Utilizing Protein Microarray Technology", Clinical Immunology, 2008, vol. 127, p. S89.
Sherer, Y., et al., "Autoantibody Explosion in Systemic Lupus Erythematosus: More than 100 Different Antibodies Found in SLE Patients", Seminars in Arthritis and Rheumatism, 2004, vol. 34, No. 2, pp. 501-537.
International Preliminary Report on Patentability for PCT/EP2015/052805 dated Aug. 16, 2016 with English Translation Attached.
International Search Report for PCT/EP2015/052805 dated May 15, 2015.

* cited by examiner a) Dendogram of the known ENA-4 antigens b) Dendogram of 50 selected SLE antigens a) SLE cohort I B) SLE cohort II C) SLE cohort III

MARKER SEQUENCES FOR DIAGNOSING AND STRATIFYING SLE PATIENTS

RELATED APPLICATIONS

This application is a national stage application (under 35 U.S.C. § 371) of PCT/EP2015/052805, filed Feb. 10, 2015, which claims benefit of European Application No. 14154557.4, filed Feb. 10, 2014, and European Application No. 14178090.8, filed Jul. 22, 2014.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence Listing_074027_0034. The size of the text file is 6,394 KB, and the text file was created on Nov. 30, 2016.

The present invention relates to methods for identifying markers for systemic lupus erythematosus (SLE) and to the markers identified with the aid of this method, which can differentiate between SLE and other autoimmune diseases on the one hand and between different SLE subgroups on the other hand. The invention also relates to panels of markers for SLE, diagnostic devices and test kits for SLE which comprise these markers, and to the use and application thereof, for example for the diagnosis, prognosis and therapy control of SLE. The invention also relates to methods for screening and for validating active substances for application in SLE subgroups.

Systemic lupus erythematosus (SLE) is a rare autoimmune disease. In the case of lupus erythematosus the body's own immune system is disregulated. It not only attacks bacteria, viruses and cancer cells, but also healthy body cells. Organs and organ systems, for example the skin, are damaged as a result.

In clinical practice, SLE is diagnosed on the basis of a combination of clinical and immunological parameters. Here, antinuclear autoantibodies (ANAs) and anti-double-stranded DNA (anti-dsDNA) autoantibodies play a key role. However, the ANA test is not specific for SLE, since other autoimmune diseases and up to 20% of healthy individuals are also positively tested. The autoreactivity against extractable nuclear antigens (ENAs) as recombinant or purified individual antigens is therefore increasingly tested, for example against Sm-protein, U1-RNP, Rho52/SS-A and Ro60/SS-B. These antigens and associated autoantibodies, however, are not sufficient for diagnosing all SLE patients without doubt, in particular in an early phase of the disease. By way of example, anti-dsDNA antibodies are indeed highly specific for SLE and can be detected in approximately 70% of patients. However, the titre of the anti-dsDNA antibodies correlates with the disease activity in some patients, but not in all patients. As a result, SLE is often only diagnosed months or years after the occurrence of the first symptoms. A further problem of the currently used diagnostic methods is that the suitability of the previously tested autoantigens for the diagnosis of organ involvement and complications is disputed, and partly conflicting data has been published.

There is thus a great need to provide new markers for the diagnosis and differential diagnosis of SLE.

Marker sequences for the diagnosis of SLE are disclosed in WO 2012/049225 A2. These marker sequences were discovered by a method in which serum samples of SLE patients and those of healthy individuals were examined by comparison and the results were statistically evaluated. The marker sequences described in WO 2012/049225 A2, however, are not sufficiently suitable for the diagnosis of SLE with regard to a distinction from other autoimmune diseases and the identification of SLE subgroups.

There is therefore still a need for markers for SLE, in particular for the distinction of SLE from other autoimmune diseases.

This object has been achieved in accordance with the invention in that a differential method comprising a multiplicity of steps has been developed, in which serum samples of healthy individuals and patients with various autoimmune diseases were examined by comparison with regard to their reactivity with a multiplicity of potential antigens and these results were statistically evaluated. The selection of the serum samples and the sequence of the steps surprisingly made it possible to identify highly specific markers for SLE which are also suitable for identifying SLE subgroups and complications such as lupus nephritis and for providing a differential diagnosis in respect of other autoimmune diseases, such as rheumatoid arthritis (RA), systemic sclerosis (SSc), ankylosing spondylitis or Bekhterev's disease (SPA), and also in respect of individuals who have early RA, i.e. have been suffering with the disease for less than two years ("patients with early RA").

The present invention relates to a method for identifying markers for systemic lupus erythematosus (SLE) comprising the following steps a) bringing serum samples of SLE patients into contact with more than 5000 antigens coupled to (Luminex) beads, measuring the binding of the individual antigens to proteins, in particular autoantibodies, in the serum of the SLE patients by means of immunofluorescence assay, and determining the median fluorescence intensity (MFI) for each individual antigen;

b) bringing serum samples of patients with rheumatoid arthritis (RA) into contact with the same antigens coupled to (Luminex) beads, measuring the binding of the individual antigens to proteins, in particular autoantibodies, in the serum of the RA patients by means of immunofluorescence assay, and determining from this the median fluorescence intensity (MFI) for each individual antigen;

c) bringing serum samples of healthy individuals into contact with the same antigens coupled to (Luminex) beads, measuring the binding of the individual antigens to proteins, in particular autoantibodies, in the serum of the healthy individuals by means of immunofluorescence assay, and determining from this the median fluorescence intensity (MFI) for each individual antigen;

d) statistically evaluating the MFI data from a), b) and c) by means of univariate analysis and thus identifying marker candidate antigens with which SLE patients can be differentiated from RA patients and from healthy individuals;

e) bringing serum samples of patients with early RA into contact with the marker candidate antigens identified in d) coupled to (Luminex) beads, measuring the binding of marker candidate antigens to proteins, in particular autoantibodies, in the serum of patients with early RA by means of immunofluorescence assay, and determining from this the median fluorescence intensity (MFI) for each marker candidate antigen;

f) bringing serum samples of patients with systemic sclerosis (SSc patients) into contact with the marker candidate antigens identified in d) coupled to (Luminex) beads, measuring the binding of marker candidate antigens to proteins, in particular autoantibodies, in the serum of SSc patients by immunofluorescence assay, and determining from this the median fluorescence intensity (MFI) for each marker candidate;

g) bringing serum samples of patients with ankylosing spondylitis or Bekhterev's disease (SPA patients) into contact with the marker candidate antigens identified in d) coupled to (Luminex) beads, measuring the binding of marker candidate antigens to proteins, in particular autoantibodies, in the serum of SPA patients by means of immunofluorescence assay, and determining from this the median fluorescence intensity (MFI) for each marker candidate antigen;

h) statistically evaluating the MFI data from e), f) and g) by means of univariate analysis and, when a threshold value of 3 standard deviations above the mean value of the healthy samples is not reached, identifying a specific marker for SLE, wherein the markers are selected from sequences SEQ ID No. 1 to 1584, homologues of sequences SEQ ID No. 1 to 1584 with at least 95% homology, subsequences of SEQ ID No. 1 to 1584, subsequences of homologues of SEQ ID No. 1 to 1584 with at least 95% homology.

The term "systemic lupus erythematosus (SLE) relates to a systemic autoimmune disease from the group of collagenoses. What is known as the butterfly rash is particularly characteristic for SLE (systemic lupus erythematosus). The diagnosis criteria for SLE are:

1. butterfly rash, 2. discoid skin changes, 3. sensitivity to light, 4. mucous membrane ulcers (generally painless), 5. arthritis in at least two joints, 6. serositis (pleurisy or pericarditis), 7. kidney involvement (proteinuria >0.5 g/d or cylinder), 8. CNS involvement (cramps or psychosis), 9. haematological findings (haemolytic anaemia, leucopenia or thrombopenia), 10. immunological findings (anti-dsDNA antibodies, anti-Sm antibodies, anticardiolipin antibodies), 11. antinuclear antibodies without taking lupus erythematosus-triggering medication.

Evaluation: With four (three) positive findings, the diagnosis is considered reliable (likely) (definition for example according to Pschyrembel, de Gruyter, 261$^{st}$ edition (2007), Berlin).

One embodiment of the invention relates to methods for identifying markers for SLE which are suitable for the diagnosis and differential diagnosis of SLE, in particular for distinction from other autoimmune diseases, preferably for distinction from other rheumatic diseases, particularly preferably for distinction from RA, SSc, and SPA. These markers are also suitable for distinction from patients with early RA. These markers for SLE according to the invention are the subject of group 1 of antigens in Table 2, which can be used for the diagnosis of SLE. For the generation of these markers, marker candidate antigens which have an adjusted p-value for the non-parametric mean value comparison between groups of <0.05 and at the same time a fold change of >1.5 and additionally an AUC resulting from the ROC analysis of >0.75 are selected on the basis of the univariate results. In addition, the ENA-4 antigens are selected. For this pool of selected marker candidate antigens, an L1-penalised logistic regression model is preferably also established within the scope of a nested cross validation. Marker candidate antigens which are not considered within the scope of the creation of the model are removed from the further consideration. The markers for SLE are thus obtained, selected from the sequences (group 1)

SEQ ID No. 1 to 24, 134, 168, 213, 367 to 369 SEQ ID No. 528 to 551, 661, 695, 741, 895 to 897 and SEQ ID No. 1057 to 1080, 1190, 1224, 1270, 1424 to 1426, homologues of SEQ ID No. 1 to 24, 134, 168, 213, 367 to 369 SEQ ID No. 528 to 551, 661, 695, 741, 895 to 897 and SEQ ID No. 1057 to 1080, 1190, 1224, 1270, 1424 to 1426 with at least 95% homology, subsequences of SEQ ID No. 1 to 24, 134, 168, 213, 367 to 369 SEQ ID No. 528 to 551, 661, 695, 741, 895 to 897 and SEQ ID No. 1057 to 1080, 1190, 1224, 1270, 1424 to 1426 and subsequences of homologues of SEQ ID No. 1 to 24, 134, 168, 213, 367 to 369 SEQ ID No. 528 to 551, 661, 695, 741, 895 to 897 and SEQ ID No. 1057 to 1080, 1190, 1224, 1270, 1424 to 1426 with at least 95% homology.

Another embodiment relates to methods for identifying markers for the subgroup of SLE patients with the complication lupus nephritis, comprising the comparison of the autoantibody profiles of SLE patients with lupus nephritis with those of SLE patients without lupus nephritis. Markers which are found by means of this embodiment of the method are specified for example in Table 2, in group 2 and group 5. These are methods for example in which the markers for the subgroup of the SLE patients with the complication lupus nephritis are selected from the sequences SEQ ID No. 25 to 54, 214, 215, 216, 217, 227, 232, 240, 244, 246, 248, 257, 287, 288, 300, 308, 314, 315, 323, 329, 330, 336, 338, 347, 349, 358, 361, 362, SEQ ID No. 552 to 581, 742, 743, 744, 745, 755, 760, 768, 772, 774, 776, 785, 815, 816, 828, 836, 842, 843, 851, 857, 858, 864, 866, 875, 877, 886, 889, 890 and SEQ ID No. 1081 to 1110, 1271, 1272, 1273, 1274, 1284, 1289, 1297, 1301, 1303, 1305, 1314, 1344, 1345, 1357, 1365, 1371, 1372, 1380, 1386, 1387, 1393, 1395, 1404, 1406, 1415, 1418, 1419, homologues of SEQ ID No. 25 to 54, 214, 215, 216, 217, 227, 232, 240, 244, 246, 248, 257, 287, 288, 300, 308, 314, 315, 323, 329, 330, 336, 338, 347, 349, 358, 361, 362, SEQ ID No. 552 to 581, 742, 743, 744, 745, 755, 760, 768, 772, 774, 776, 785, 815, 816, 828, 836, 842, 843, 851, 857, 858, 864, 866, 875, 877, 886, 889, 890 and SEQ ID No. 1081 to 1110, 1271, 1272, 1273, 1274, 1284, 1289, 1297, 1301, 1303, 1305, 1314, 1344, 1345, 1357, 1365, 1371, 1372, 1380, 1386, 1387, 1393, 1395, 1404, 1406, 1415, 1418, 1419 with at least 95% homology, subsequences of SEQ ID No. 25 to 54, 214, 215, 216, 217, 227, 232, 240, 244, 246, 248, 257, 287, 288, 300, 308, 314, 315, 323, 329, 330, 336, 338, 347, 349, 358, 361, 362, SEQ ID No. 552 to 581, 742, 743, 744, 745, 755, 760, 768, 772, 774, 776, 785, 815, 816, 828, 836, 842, 843, 851, 857, 858, 864, 866, 875, 877, 886, 889, 890 and SEQ ID No. 1081 to 1110, 1271, 1272, 1273, 1274, 1284, 1289, 1297, 1301, 1303, 1305, 1314, 1344, 1345, 1357, 1365, 1371, 1372, 1380, 1386, 1387, 1393, 1395, 1404, 1406, 1415, 1418, 1419 and subsequences of homologues of SEQ ID No. 25 to 54, 214, 215, 216, 217, 227, 232, 240, 244, 246, 248, 257, 287, 288, 300, 308, 314, 315, 323, 329, 330, 336, 338, 347, 349, 358, 361, 362, SEQ ID No. 552 to 581, 742, 743, 744, 745, 755, 760, 768, 772, 774, 776, 785, 815, 816, 828, 836, 842, 843, 851, 857, 858, 864, 866, 875, 877, 886, 889, 890 and SEQ ID No. 1081 to 1110, 1271, 1272, 1273, 1274, 1284, 1289, 1297, 1301, 1303, 1305, 1314, 1344, 1345, 1357, 1365, 1371, 1372, 1380, 1386, 1387, 1393, 1395, 1404, 1406, 1415, 1418, 1419 with at least 95% homology.

A further embodiment relates to methods which comprise the statistical evaluation by means of an L1-penalised logistic regression model with five-fold cross validation and twenty times repetition and selection of the markers which occur at a frequency of 50% or more. Markers which can be identified by means of this embodiment of the method are specified for example in Table 2, group 2. These are methods for example in which the markers for the subgroup of the SLE patients with the complication lupus nephritis are selected from the sequences SEQ ID No. 25 to 54, SEQ ID No. 552 to 581 and SEQ ID No. 1081 to 1110, homologues of 25 to 54, SEQ ID No. 552 to 581 and SEQ ID No. 1081 to 1110 with at least 95% homology, subsequences of SEQ ID No. 25 to 54, SEQ ID No. 552 to 581 and SEQ ID No. 1081 to 1110 and subsequences of homologues of SEQ ID No. 25 to 54, SEQ ID No. 552 to 581 and SEQ ID No. 1081 to 1110 with at least 95% homology.

In a further embodiment of the method, markers for defined subgroups of SLE patients are identified in that the sequences SEQ ID No. 1 to 527 (clone sequences) are correlated with one of the sequences SEQ ID No. 1 to 527 by calculation of the Spearman's rank correlation coefficient for the particular marker. In this way, the markers of groups 1, 2 and 3 in Table 2 can be identified with the method according to the invention, for example. These are methods for example in which the markers which demonstrate a correlation with one another of the reactivities in SLE patients are selected from the sequences (group 3)

SEQ ID No. 55 to 111, SEQ ID No. 582 to 1005 and SEQ ID No. 1111 to 1167, homologues of SEQ ID No. 55 to 111, SEQ ID No. 582 to 1005 and SEQ ID No. 1111 to 1167 with at least 95% homology, subsequences of SEQ ID No. 55 to 111, SEQ ID No. 582 to 1005 and SEQ ID No. 1111 to 1167 and subsequences of homologues of SEQ ID No. 55 to 111, SEQ ID No. 582 to 1005 and SEQ ID No. 1111 to 1167 with at least 95% homology and from the sequences (group 2)

SEQ ID No. 25 to 54, SEQ ID No. 552 to 581 and SEQ ID No. 1081 to 1110, homologues of SEQ ID No. 25 to 54, SEQ ID No. 552 to 581 and SEQ ID No. 1081 to 1110 with at least 95% homology, subsequences of SEQ ID No. 25 to 54, SEQ ID No. 552 to 581 and SEQ ID No. 1081 to 1110 and subsequences of homologues of SEQ ID No. 25 to 54, SEQ ID No. 552 to 581 and SEQ ID No. 1081 to 1110 with at least 95% homology and from the sequences (group 1)

SEQ ID No. 1 to 24, 134, 168, 213, 367 to 369 SEQ ID No. 528 to 551, 661, 695, 741, 895 to 897 and SEQ ID No. 1057 to 1080, 1190, 1224, 1270, 1424 to 1426, homologues of SEQ ID No. 1 to 24, 134, 168, 213, 367 to 369 SEQ ID No. 528 to 551, 661, 695, 741, 895 to 897 and SEQ ID No. 1057 to 1080, 1190, 1224, 1270, 1424 to 1426 with at least 95% homology, subsequences of SEQ ID No. 1 to 24, 134, 168, 213, 367 to 369 SEQ ID No. 528 to 551, 661, 695, 741, 895 to 897 and SEQ ID No. 1057 to 1080, 1190, 1224, 1270, 1424 to 1426 and subsequences of homologues of SEQ ID No. 1 to 24, 134, 168, 213, 367 to 369 SEQ ID No. 528 to 551, 661, 695, 741, 895 to 897 and SEQ ID No. 1057 to 1080, 1190, 1224, 1270, 1424 to 1426 with at least 95% homology.

One embodiment of the invention relates to methods for identifying markers for the subgroup of ENA-4-negative SLE patients. This embodiment of the method for example comprises the testing of the serum samples of SLE patients for the absence of autoantibodies against the extractable nuclear antigens Sm-protein, U1-RNP, Rho52/SS-A and Ro60/SS-B. By way of example, the markers of group 4, Table 2 can thus be identified. These are methods for example in which the markers for ENA-4-negative SLE patients are selected from the sequences (group 4)

SEQ ID No. 112 to 213 and 278, SEQ ID No. 639 to 741 and 806 and SEQ ID No. 1168 to 1270 and 1335, homologues of SEQ ID No. 112 to 213 and 278, SEQ ID No. 639 to 741 and 806 and SEQ ID No. 1168 to 1270 and 1335 with at least 95% homology, subsequences of SEQ ID No. 112 to 213 and 278, SEQ ID No. 639 to 741 and 806 and SEQ ID No. 1168 to 1270 and 1335 and subsequences of homologues of SEQ ID No. 112 to 213 and 278, SEQ ID No. 639 to 741 and 806 and SEQ ID No. 1168 to 1270 and 1335 with at least 95% homology.

One embodiment of the invention relates to methods comprising the selection of markers which have an adjusted p-value for the non-parametric mean value comparison between groups of less than 0.05, and at the same time a fold change of greater than 1.5 and an AUC resulting from the ROC analysis of greater than 0.75. By way of example, the markers of groups 1, 4 and 6 can thus be identified. The corresponding calculations for panels of markers are specified in Table 5, in which the corresponding marker composition in the panels (arrangements) can be inferred from Table 4. These are methods for example in which the markers are selected from the sequences (group 6)

SEQ ID No. 218 to 226, 228 to 231, 233 to 239, 241, 242, 243, 245, 247, 249 to 256, 258 to 277, 279 to 286, 289 to 299, 301 to 307, 309 to 313, 316 to 322, 324 to 328, 331 to 335, 337, 339 to 346, 348, 350 to 357, 359, 360, 363 to 366,

SEQ ID No. 746 to 754, 756 to 759, 761 to 767, 769, 770, 771, 773, 775, 777 to 784, 786 to 805, 807 to 814, 817 to 827, 829 to 835, 837 to 841, 844 to 850, 851 to 855, 859 to 863, 865, 867 to 874, 876, 878 to 885, 887, 888, 891 to 894 and SEQ ID No. 1275 to 1283, 1285 to 1288, 1290 to 1296, 1298, 1299, 1300, 1302, 1304, 1306 to 1313, 1315 to 1334, 1336 to 1343, 1346 to 1356, 1358 to 1364, 1366 to 1370, 1373 to 1379, 1380 to 1384, 1388 to 1392, 1394, 1396 to 1403, 1405, 1407 to 1414, 1416, 1418, 1420 to 1423, homologues of SEQ ID No. 218 to 226, 228 to 231, 233 to 239, 241, 242, 243, 245, 247, 249 to 256, 258 to 277, 279 to 286, 289 to 299, 301 to 307, 309 to 313, 316 to 322, 324 to 328, 331 to 335, 337, 339 to 346, 348, 350 to 357, 359, 360, 363 to 366, SEQ ID No. 746 to 754, 756 to 759, 761 to 767, 769, 770, 771, 773, 775, 777 to 784, 786 to 805, 807 to 814, 817 to 827, 829 to 835, 837 to 841, 844 to 850, 851 to 855, 859 to 863, 865, 867 to 874, 876, 878 to 885, 887, 888, 891 to 894, SEQ ID No. 1275 to 1283, 1285 to 1288, 1290 to 1296, 1298, 1299, 1300, 1302, 1304, 1306 to 1313, 1315 to 1334, 1336 to 1343, 1346 to 1356, 1358 to 1364, 1366 to 1370, 1373 to 1379, 1380 to 1384, 1388 to 1392, 1394, 1396 to 1403, 1405, 1407 to 1414, 1416, 1418, 1420 to 1423 with at least 95% homology, subsequences of SEQ ID No. 218 to 226, 228 to 231, 233 to 239, 241, 242, 243, 245, 247, 249 to 256, 258 to 277, 279 to 286, 289 to 299, 301 to 307, 309 to 313, 316 to 322, 324 to 328, 331 to 335, 337, 339 to 346, 348, 350 to 357, 359, 360, 363 to 366, SEQ ID No. 746 to 754, 756 to 759, 761 to 767, 769, 770, 771, 773, 775, 777 to 784, 786 to 805, 807 to 814, 817 to 827, 829 to 835, 837 to 841, 844 to 850, 851 to 855, 859 to 863, 865, 867 to 874, 876, 878 to 885, 887, 888, 891 to 894, SEQ ID No. 1275 to 1283, 1285 to 1288, 1290 to 1296, 1298, 1299, 1300, 1302, 1304, 1306 to 1313, 1315 to 1334, 1336 to 1343, 1346 to 1356, 1358 to 1364, 1366 to 1370, 1373 to 1379, 1380 to 1384, 1388 to 1392, 1394, 1396 to 1403, 1405, 1407 to 1414, 1416, 1418, 1420 to 1423 and subsequences of homologues of SEQ ID No. 218 to 226, 228 to 231, 233 to 239, 241, 242, 243, 245, 247, 249 to 256, 258 to 277, 279 to 286, 289 to 299, 301 to 307, 309 to 313, 316 to 322, 324 to 328, 331 to 335, 337, 339 to 346, 348, 350 to 357, 359, 360, 363 to 366, SEQ ID No. 746 to 754, 756 to 759, 761 to 767, 769, 770, 771, 773, 775, 777 to 784, 786 to 805, 807 to 814, 817 to 827, 829 to 835, 837 to 841, 844 to 850, 851 to 855, 859 to 863, 865, 867 to 874, 876, 878 to 885, 887, 888, 891 to 894, SEQ ID No. 1275 to 1283, 1285 to 1288, 1290 to 1296, 1298, 1299, 1300, 1302, 1304, 1306 to 1313, 1315 to 1334, 1336 to 1343, 1346 to 1356, 1358 to 1364, 1366 to 1370, 1373 to 1379, 1380 to 1384, 1388 to 1392, 1394, 1396 to 1403, 1405, 1407 to 1414, 1416, 1418, 1420 to 1423 with at least 95% homology.

Group 7 in table 2 contains a further 85 statistically significant antigens from the methods according to the invention; these are markers selected from the sequences SEQ ID No. 367 to 450, SEQ ID No. 895 to 979, SEQ ID No. 1424 to 1507, homologues of SEQ ID No. 367 to 450, SEQ ID No. 895 to 979, SEQ ID No. 1424 to 1507 with at least 95% homology, subsequences of SEQ ID No. 367 to 450, SEQ ID No. 895 to 979, SEQ ID No. 1424 to 1507 and subsequences of homologues of SEQ ID No. 367 to 450, SEQ ID No. 895 to 979, SEQ ID No. 1424 to 1507 with at least 95% homology, which can be used for the diagnosis and differential diagnosis of SLE compared with healthy individuals and other autoimmune diseases. Antigens from group 7 were also used for the calculation of biomarker combinations.

Group 8 consists of further statistically significant antigens from the methods according to the invention; markers selected from the sequences SEQ ID No. 451 to 527, SEQ ID No. 980 to 1056, SEQ ID No. 1508 to 1584, homologues of SEQ ID No. 451 to 527, SEQ ID No. 980 to 1056, SEQ ID No. 1508 to 1584 with at least 95% homology, subsequences of SEQ ID No. 451 to 527, SEQ ID No. 980 to 1056, SEQ ID No. 1508 to 1584 and subsequences of homologues of SEQ ID No. 451 to 527, SEQ ID No. 980 to 1056, SEQ ID No. 1508 to 1584 with at least 95% homology were detected and identified for the autoantibodies in SLE patients.

The invention also relates to the individual markers for SLE identified with the method according to the invention. The method concerns markers for SLE selected from the sequences SEQ ID No. 1 to 1584, homologues of sequences SEQ ID No. 1 to 1584 with at least 95% homology, subsequences of SEQ ID No. 1 to 1584 and subsequences of homologues of SEQ ID No. 1 to 1584 with at least 95% homology. The method concerns the markers of groups 1, 2, 3, 4, 5, 6, 7, 8 in Table 2, wherein the respective groups comprise the markers of the clone sequences specified in Table 2, the corresponding RNA sequences, the corresponding protein sequences, the relevant homologues with a homology of at least 95%, and the relevant subsequences. The invention relates to a marker for SLE selected from the sequences SEQ ID No. 528 to 1056 (RNA sequences), SEQ ID No. 1057 to 1584 (protein sequences). The markers according to the invention and the associated nucleic acid sequences are presented in Table 2 (SEQ ID No. of the relevant clone sequences is specified) and can be unambiguously identified by their cited database entry, for example at www.ncbi.nlm.nih.gov/, by means of their GeneID (Table 2). The sequences SEQ ID No. 1-1584 are specified in the accompanying sequence protocol, wherein SEQ ID No. 1-527 are clone sequences (cDNA), SEQ ID No. 528-1056 are RNA sequences, and SEQ ID No. 1057-1584 are protein sequences.

The invention also relates to the proteins coded by sequences SEQ ID No. 1 to 1056, the proteins coded by homologues of the sequences SEQ ID No. 1 to 1056 with at least 95% homology to the sequences SEQ ID No. 1 to 1056, the proteins coded by subsequences of SEQ ID No. 1 to 1056, the proteins coded by homologues of the subsequences of SEQ ID No. 1 to 1056 with at least 95% homology in the subsequences. In a preferred embodiment these are the proteins SEQ ID No. 1057 to 1584, homologues of the proteins with the sequences SEQ ID No. 1057 to 1584 with at least 95% homology, subsequences of SEQ ID No. 1057 to 1584, homologues of the subsequences of SEQ ID No. 1057 to 1584 with at least 95% homology.

The invention also relates to a panel of markers (also referred to as an arrangement of markers), comprising at least two different markers for SLE which are selected independently of one another from the sequences SEQ ID No. 1 to 1584, homologues of sequences SEQ ID No. 1 to 1584 with at least 95% homology, subsequences of SEQ ID No. 1 to 1584 and subsequences of homologues of SEQ ID No. 1 to 1584 with at least 95% homology. A panel of markers for SLE can comprise 2 to 20 or more, for example 3, 4, 5, 6, 7, 8, 9, 10, 11, 12, 13, 14, 15, 16, 17, 18, 19, 20, 25, 30, 40, 50, 100 or more different markers for SLE and optionally further markers, wherein the markers of SLE are selected independently of one another from the sequences SEQ ID No. 1 to 1584, homologues of sequences SEQ ID No. 1 to 1584 with at least 95% homology, subsequences of SEQ ID No. 1 to 1584 and subsequences of homologues of SEQ ID No. 1 to 1584 with at least 95% homology, and the proteins coded by the sequences.

On account of the high clinical and serological heterogeneity of the SLE disease, it is difficult to diagnose SLE unambiguously using just one biomarker. It is therefore often necessary to combine (where possible) uncorrelated autoantigens to form what are known as panels of markers (biomarker panels for SLE). By way of example, within the scope of individualised medicine, corresponding panels of markers for SLE can be composed individually for the relevant SLE subtype (subgroup) for individual patients or patient groups. It is therefore also necessary to have available a multiplicity of potential markers for SLE in order to select suitable subgroups or subtypes of specific markers for SLE for the individual case in question. A corresponding panel can be embodied for example in the form of an arrangement, an array, or also one or more beads, preferably Luminex beads. The invention thus relates to an arrangement comprising one or more markers according to the invention, a protein array comprising one or more markers according to the invention, a bead (small ball or platelet) comprising one or more markers according to the invention. Examples of SLE panels (SLE arrangements) are given in Table 4.

The invention also relates to a diagnostic device or a test kit comprising at least one marker for SLE selected from the sequences SEQ ID No. 1 to 1584, homologues of sequences SEQ ID No. 1 to 1584 with at least 95% homology, subsequences of SEQ ID No. 1 to 1584 and subsequences of homologues of SEQ ID No. 1 to 1584 with at least 95% homology, and the proteins coded by the sequences. A corresponding diagnostic device or a corresponding test kit can also comprise a panel of markers for SLE and optionally further auxiliaries and additives.

The invention also relates to the use of one or more markers for SLE selected from sequences SEQ ID No. 1 to 1584, homologues of sequences SEQ ID No. 1 to 1584 with at least 95% homology, subsequences of SEQ ID No. 1 to 1584 and subsequences of homologues of SEQ ID No. 1 to 1584 with at least 95% homology, and the proteins coded by the sequences, a marker panel for SLE, or a diagnostic device or test kit for identifying subgroups of SLE patients, for diagnosing SLE, for differential diagnosis (i.e. for distinction from other autoimmune diseases or other rheumatic diseases), for prognosis in the case of SLE, for therapy control in the case of SLE, for active substance selection in the case of SLE, for therapy monitoring in the case of SLE, or for aftercare in the case of SLE.

The invention also relates to the use of one or more of the markers for SLE selected from the sequences SEQ ID No. 1 to 1584, homologues of sequences SEQ ID No. 1 to 1584 with at least 95% homology, subsequences of SEQ ID No. 1 to 1584 and subsequences of homologues of SEQ ID No. 1 to 1584 with at least 95% homology, and the proteins coded by the sequences for the differentiation of SLE from RA and/or other autoimmune diseases, for example SSc and/or SPA and/or RA and/or early RA.

The invention also relates to the use of one or more markers for SLE selected from the sequences SEQ ID No. 112 to 213 and 278, SEQ ID No. 639 to 741 and 806 and SEQ ID No. 1168 to 1270 and 1335, homologues of SEQ ID No. 112 to 213 and 278, SEQ ID No. 639 to 741 and 806 and SEQ ID No. 1168 to 1270 and 1335 with at least 95% homology, subsequences of SEQ ID No. 112 to 213 and 278, SEQ ID No. 639 to 741 and 806 and SEQ ID No. 1168 to 1270 and 1335 and subsequences of homologues of SEQ ID No. 112 to 213 and 278, SEQ ID No. 639 to 741 and 806 and SEQ ID No. 1168 to 1270 and 1335 with at least 95% homology, and the proteins coded by the sequences for the diagnosis of SLE in ENA-4-negative SLE patients.

The invention also relates to the use of one or more markers for SLE selected from the sequences SEQ ID No. 25 to 54, SEQ ID No. 552 to 581 and SEQ ID No. 1081 to 1110, homologues of SEQ ID No. 25 to 54, SEQ ID No. 552 to 581 and SEQ ID No. 1081 to 1110 with at least 95% homology, subsequences of SEQ ID No. 25 to 54, SEQ ID No. 552 to 581 and SEQ ID No. 1081 to 1110 and subsequences of homologues of SEQ ID No. 25 to 54, SEQ ID No. 552 to 581 and SEQ ID No. 1081 to 1110 with at least 95% homology, and the proteins coded by the sequences for the diagnosis and differential diagnosis of lupus nephritis in SLE patients. Lupus nephritis is a common and serious complication of SLE. In the case of complete failure of the kidney function, therapy with dialysis is necessary. In order to avoid long-term damage, it is therefore important to identify and treat any kidney involvement early on. This is also of particular importance for the development of active substances for SLE in general, i.e. for the development of active substances for patients with lupus nephritis. Previously, there were still no biomarkers available able to diagnose lupus nephritis in all patients.

The invention also relates to markers for SLE and lupus nephritis selected from the sequences SEQ ID No. 25 to 54, SEQ ID No. 552 to 581 and SEQ ID No. 1081 to 1110, homologues of SEQ ID No. 25 to 54, SEQ ID No. 552 to 581 and SEQ ID No. 1081 to 1110 with at least 95% homology, subsequences of SEQ ID No. 25 to 54, SEQ ID No. 552 to 581 and SEQ ID No. 1081 to 1110 and subsequences of homologues of SEQ ID No. 25 to 54, SEQ ID No. 552 to 581 and SEQ ID No. 1081 to 1110 with at least 95% homology, and the proteins coded by the sequences.

The autoantibody profiles of SLE patients with lupus nephritis were therefore compared with those without lupus nephritis. Following univariate statistical evaluation, a threshold value of p<0.05 and a 1.5 times modified reactivity compared with the control group were applied.

The invention also relates to a method for the early detection, diagnosis, differential diagnosis, prognosis, therapy control and/or after-care of SLE, in which a. at least one of the markers for SLE selected from the sequences SEQ ID No. 1 to 1584, the homologues of sequences SEQ ID No. 1 to 1584 with at least 95% homology, the subsequences of SEQ ID No. 1 to 1584 or the subsequences of homologues of SEQ ID No. 1 to 1584 with at least 95% homology, and the proteins coded by the sequences b. is brought into contact with bodily fluid or a tissue sample from an individual to be tested, and c. an interaction of the bodily fluid or of the tissue sample with the one this or more markers from a. is detected.

The invention also relates to a target for the therapy of SLE selected from the sequences SEQ ID No. 1 to 1584, the homologues of sequences SEQ ID No. 1 to 1584 with at least 95% homology, the subsequences of SEQ ID No. 1 to 1584 and the subsequences of homologues of SEQ ID No. 1 to 1584 with at least 95% homology, and the proteins coded by the sequences.

The invention also relates to a composition, in particular a pharmaceutical composition, comprising at least one of the sequences SEQ ID No. 1 to 1584, the homologues of sequences SEQ ID No. 1 to 1584 with at least 95% homology, the subsequences of SEQ ID No. 1 to 1584 or the subsequences of the homologues of SEQ ID No. 1 to 1584 with at least 95% homology, and the proteins coded by the sequences.

The invention also relates to a method for screening active substances for SLE, in which a. at least one of the markers for SLE selected from the sequences SEQ ID No. 1 to 1584, the homologues of sequences SEQ ID No. 1 to 1584 with at least 95% homology, the subsequences of SEQ ID No. 1 to 1584 or the subsequences of homologues of SEQ ID No. 1 to 1584 with at least 95% homology, and the proteins coded by the sequences b. is brought into contact with a substance to be tested, and c. an interaction of the substance with the one or more markers from a. is detected.

The large clinical heterogeneity of SLE currently constitutes a big problem both for diagnosis and for active substance development.

The identification of specific antibody signatures in SLE patient subgroups therefore constitutes an important step for the improved definition of patient groups in clinical studies.

By way of example, as presented under Example 9, specific autoantibodies for lupus nephritis could be used to recruit this subgroup for drug studies.

A large number of new active substances and therapeutic antibodies are currently undergoing clinical development: inter alia, therapeutic antibodies against cell-surface receptors of immune cells, such as anti-CD20, anti-CD22, or against pro-inflammatory cytokines, such as anti-IL6, are being developed. It is therefore now possible, due to the identification of serologically defined subgroups of SLE, to link this to a target-specific response to a drug. The invention also relates to the use of one or more markers for SLE according to the invention, of an arrangement according to the invention (panel of markers for SLE), of a protein array according to the invention, of a bead according to the invention, of a diagnostic device according to the invention, or of a test kit according to the invention for the individualised diagnosis and/or therapy in individual patients, patient groups, cohorts, population groups, variants of SLE, or stages of SLE.

The invention also relates to the use of one or more markers according to the invention for SLE, of an arrangement according to the invention (panel of markers for SLE), of a protein array according to the invention, of a bead according to the invention, of a diagnostic device according to the invention, or of a test kit according to the invention for the detection and/or determination of the amount of one or more autoantibodies associated with SLE, for example in bodily fluids such as serum, tissue or tissue samples of the patient. The invention also relates to the use of one or more markers according to the invention, of an arrangement according to the invention, of a protein array according to the invention, of a bead according to the invention, of a diagnostic device according to the invention, or of a test kit according to the invention for the analysis of autoantibody profiles of patients, in particular for the qualitative and/or quantitative analysis of autoantibodies and/or for the monitoring of changes of autoantibody profiles associated with SLE, for example in bodily fluids such as serum, tissue or tissue samples of the patient.

A particular embodiment of the invention relates to methods for the early identification and diagnosis of SLE, in which the detection of an interaction of the bodily fluid or the tissue sample with the one or more markers indicates an SLE-associated autoantibody profile of the patient or of a cohort or of a population group or of a certain course of disease (prognosis) or of a certain response to a therapy/drug. The invention therefore includes the use of at least one marker for SLE selected from the sequences SEQ ID No. 1 to 1584, the homologues of sequences SEQ ID No. 1 to 1584 with at least 95% homology, the subsequences of SEQ ID No. 1 to 1584 or the subsequences of homologues of SEQ ID No. 1 to 1584 with at least 95% homology, and the proteins coded by the sequences for the analysis of autoantibody profiles of patients, in particular for the quantitative analysis and/or for the monitoring of changes of autoantibody profiles of SLE patients.

An interaction of the bodily fluid or the tissue sample with the one or more SLE markers can be detected for example by a probe, in particular by an antibody.

In a preferred embodiment at least 2, for example 3, 4, 5, 6, 7, 8, 9, 10, preferably 15 to 20 markers for SLE or 30 to 50 or 100 or more markers are used together or in combination, either simultaneously or in succession, wherein the markers for SLE are selected independently of one another from the sequences SEQ ID No. 1 to 1584, the homologues of sequences SEQ ID No. 1 to 1584 with at least 95% homology, the subsequences of SEQ ID No. 1 to 1584 or the subsequences of homologues of SEQ ID No. 1 to 1584 with at least 95% homology, and the proteins coded by the sequences.

A particular embodiment of the invention relates to a method according to the invention, wherein the stratification or therapy control includes decisions relating to the treatment and therapy of the patient, in particular hospitalisation of the patient, use, efficacy and/or dosage of one or more drugs, a therapeutic measure, or the monitoring of the course of the disease and course of therapy, aetiology, or classification of a disease inclusive of prognosis. The invention also relates to a method for stratification, in particular for risk stratification and/or therapy control of a patient with SLE.

The stratification of the patient with SLE into new or established SLE subgroups as well as the expedient selection of patient groups for the clinical development of new therapeutic agents is also included. The term therapy control likewise includes the division of patients into responders and non-responders with regard to a therapy or course thereof.

The invention in particular also relates to the detection and determination of the amount of at least two different autoantibodies in a patient by means of the SLE markers according to the invention, wherein at least two different SLE markers are preferably used. The invention also relates to a use according to the invention of one or more SLE markers, wherein at least 2, for example 3 to 5 or 10, preferably 30 to 50, or 50 to 100 or more SLE markers or the relevant autoantibodies on or from a patient to be tested are determined.

The invention comprises the SLE markers on a solid substrate, for example a filter, a membrane, a small platelet or ball, for example a magnetic or fluorophore-labelled ball, a silicon wafer, a bead, a chip, a mass spectrometry target, or a matrix, or the like. Different materials are suitable as substrates and are known to a person skilled in the art, for example glass, metal, plastic, filter, PVDF, nitrocellulose, or nylon (for example Immobilon P Millipore, Protran Whatman, Hybond N+ Amersham).

The substrate for example can correspond to a grid with the dimensions of a microtitre plate (8-12 well strips, 96 wells, 384 wells or more), of a silicon wafer, of a chip, of a mass spectrometry target, or of a matrix.

In one embodiment of the invention markers for SLE are present in the form of clone sequences or clone(s).

The markers according to the invention can be combined, supplemented or extended with known biomarkers for SLE or biomarkers for other diseases. With a combination of this type, a proportion of markers for SLE according to the invention of preferably at least 50%, preferably 60%, and particularly preferably 70% or more is comprised.

In a preferred embodiment the use of the SLE markers and the methods according to the invention are implemented outside the human or animal body, for example the diagnosis is performed ex vivo/in vitro, preferably by means of an assay, as detailed below.

In the sense of this invention, the term "diagnosis" means the positive determination of SLE with the aid of the markers according to the invention and the assignment of the patients or symptoms thereof to the disease SLE. The term "diagnosis" includes the medical diagnosis and tests in this respect, in particular in vitro diagnosis and laboratory diagnosis, and also proteomics and nucleic acid blots. Further tests may be necessary for assurance and in order to rule out other diseases. The term "diagnosis" therefore includes in particular the differential diagnosis of SLE by means of the markers according to the invention.

In the sense of this invention, "stratification or therapy control" means that, for example, the methods according to the invention allow decisions for the treatment and therapy of the patient, whether it is the hospitalisation of the patient, the use, efficacy and/or dosage of one or more drugs, a therapeutic measure or the monitoring of the course of a disease and the course of therapy or aetiology or classification of a disease, for example into a new or existing sub-type, or the differentiation of diseases and patients thereof. In a further embodiment of the invention, the term "stratification" in particular includes the risk stratification with the prognosis of an "outcome" of a negative health event.

"Prognosis" means the prediction of the course of a disease.

In accordance with the invention, "therapy control" means, for example, the prediction and monitoring of the response to a drug or a therapy as well as aftercare.

Within the scope of this invention, the term "patient" is understood to mean any test subject, any individual (human or mammal), with the provision that the test subject or individual is tested for SLE.

The term "marker for SLE" in the sense of this invention means that the nucleic acid, for example DNA, in particular cDNA or RNA or the coded amino acid sequence or the polypeptide or protein are significant (specific) for SLE and/or the autoantibody profiles associated with SLE. Markers according to the invention are nucleic acid sequences and/or amino acid sequences according to the definition in the appended sequence protocol (SEQ ID No. 1 to SEQ ID No. 1584), homologues and subsequences thereof, wherein modified nucleic acid and amino acid sequences are also included. Here, marker for SLE means, for example, that the cDNA or RNA or the polypeptide or protein obtainable therefrom interacts with substances from the bodily fluid or tissue sample from a patient with SLE (for example antigen (epitope)/antibody (paratope) interaction). In a particularly preferred embodiment of the invention the marker for SLE is an antigen or part of an antigen or codes for an antigen or for part of an antigen.

The substances from the bodily fluid or tissue sample occur either only in an amplified manner or at least in an amplified manner in the case of SLE or are expressed, whereas these substances are not present in patients without SLE or healthy individuals, or at least are present to a lesser extent (smaller amount, lower concentration). Markers for SLE can also be characterised in that they interact with substances from the bodily fluid or tissue sample from patients with SLE, because these substances no longer occur or are no longer expressed or occur or are expressed at least in a much lower amount/concentration in the case of SLE, whereas these substances are present or are at least present to a much higher extent in patients without SLE. Markers for SLE can also be present in healthy test subjects, however the amount (concentration) thereof changes for example with the development, establishment and therapy of SLE. One or more markers can in this way map a profile of substances from bodily fluid and tissue sample, for example an SLE-associated autoantibody profile of the patient in question. Markers according to the invention are biomarkers for SLE.

Autoantibody profiles comprise the amount of one or more autoantibodies of which the occurrence/expression accompanies the development and/or establishment of SLE. Autoantibody profiles therefore include on the one hand the composition, i.e. one or more autoantibodies is/are expressed only in the case of SLE for example, and also the amount/concentration of individual autoantibodies, i.e. the amount/concentration of individual autoantibodies changes with the development and establishment of SLE. These changes can be detected with the aid of the marker sequences according to the invention.

In a particularly preferred embodiment the SLE marker identifies/binds to autoantibodies which are present (intensified) or are present to a lower extent (or no longer) during the course of the development, establishment and therapy of SLE. Autoantibodies are formed by the body against endogenous antigens which are formed for example in the case of SLE. Autoantibodies are formed by the body against different substances and pathogens. Within the scope of the present invention, the autoantibodies which are formed with the occurrence and during the course of the development of SLE and/or of which the expression is up-regulated or down-regulated are detected in particular. These autoantibodies can be detected with the aid of the methods and markers according to the invention, and the detection and monitoring (for example of the amount) thereof can be used for the early identification, diagnosis and/or therapy monitoring/therapy control and the prognosis and prediction of the risk of the re-occurrence of SLE within the scope of the after-care.

The autoantibody profiles can be sufficiently characterised with use of just a single SLE marker. In other cases, two or more SLE markers are necessary in order to map an autoantibody profile which is specific for SLE.

In one embodiment of the invention autoantibodies which derive from another individual and which for example originate from a commercial cDNA bank can be detected using SLE markers.

In another embodiment of the invention these autoantibodies can be detected using SLE markers which derive from the same individual and which for example originate from a cDNA bank produced individually for the patient or a group of patients for example within the scope of individualised medicine. By way of example, homologues of the specified SLE markers with the sequences SEQ ID. No. 1 to 1584 or subsequences thereof can be used.

Autoantibodies can be formed by the patient already many years prior to the occurrence of the first symptoms of disease. An early identification, diagnosis and also prognosis and preventative treatment or lifestyle change and other possibilities for prevention might therefore be possible even years prior to the visible outbreak of the disease. The devices, means and methods according to the invention enable a very early intervention compared with known methods, which significantly improves the prevention, treatment possibilities and effects of SLE.

Since the SLE-associated autoantibody profiles change during the establishment and treatment/therapy of SLE, the invention also enables the detection and monitoring of SLE at any stage of the development and treatment and also monitoring within the scope of SLE after-care. The means according to the invention, for example a corresponding diagnostic device or a test kit, also allow simple handling at home by the patient and an economical routine precautionary measure for early identification.

In particular due to the use of antigens as specific markers for SLE which derive from sequences already known, for example from commercial cDNA banks, test subjects can be tested and any present SLE-associated autoantibodies can be detected in these test subjects, even if the corresponding autoantigens are not (yet) known in these test subjects.

Different patients can have different SLE-associated autoantibody profiles, for example different cohorts or population groups can differ from one another. Here, any patient can form one or more different SLE-associated autoantibodies during the course of the development of SLE and the progression of the SLE disease, that is to say even different autoantibody profiles. In addition, the composition and/or the amount of formed autoantibodies can change during the course of the SLE development and progression of the disease, such that a quantitative evaluation is necessary. The therapy/treatment of SLE leads to changes in the composition and/or the amount of SLE-associated autoantibodies. The large selection of SLE markers according to the invention which are provided with this invention enables the individual compilation of SLE markers in an arrangement, i.e. a panel, for individual patients, groups of patients, certain cohorts, population groups and the like. In one individual case, the use of one SLE marker may therefore be sufficient, whereas in other cases at least two or more SLE markers must be used together or in combination in order to create a conclusive autoantibody profile.

Compared with other biomarkers, the detection of SLE-associated autoantibodies for example in the serum or plasma of patients has the advantage of high stability and storage capability and good detectability. The presence of autoantibodies also is not subject to a circadian rhythm, and therefore the sampling is independent of the time of day, food intake, and the like.

In addition, the SLE-associated autoantibodies can be detected with the aid of the corresponding antigens/autoantigens in known assays, such as ELISA or Western Blot, and the results can be checked in this way.

In the sense of the invention, an interaction between the SLE marker and the serum in question, for example an autoantibody of the patient, is detected. Such an interaction is, for example, a bond, in particular a binding substance on at least one SLE-specific marker, or, in the case that the SLE-specific marker is a nucleic acid, for example a cDNA, the hybridisation with a suitable substance under selected conditions, in particular stringent conditions (for example as defined conventionally in J. Sambrook, E. F. Fritsch, T. Maniatis (1989), Molecular cloning: A laboratory manual, 2nd Edition, Cold Spring Harbor Laboratory Press, Cold Spring Harbor, USA or Ausubel, "Current Protocols in Molecular Biology", Green Publishing Associates and Wiley Interscience, N.Y. (1989)). One example of stringent hybridisation conditions is: hybridisation in 4×SSC at 65° C. (alternatively in 50% formamide and 4×SSC at 42° C.), followed by a number of washing steps in 0.1×SSC at 65° C. for a total of approximately one hour. An example of less stringent hybridisation conditions is hybridisation in 4×SSC at 37° C., followed by a number of washing steps in 1×SSC at room temperature. The interaction between the bodily fluid or tissue sample from a patient and the markers for SLE is preferably a protein-protein interaction.

In accordance with the invention, such substances, for example antigens, autoantigens and SLE-associated autoantibodies, are part of a bodily fluid, in particular blood, whole blood, blood plasma, blood serum, patient serum, urine, cerebrospinal fluid, synovial fluid or a tissue sample from the patient. The invention in particular relates to the use of these bodily fluids and tissue samples for early detection, diagnosis, prognosis, therapy control and aftercare.

The SLE-specific markers, in a further embodiment of the invention, have a recognition signal that is addressed to the substance to be bound (for example antibody, nucleic acid). In accordance with the invention, the recognition signal for a protein is preferably an epitope and/or paratope and/or hapten, and for a cDNA is preferably a hybridisation or binding region.

Homologues of the markers according to the invention SEQ ID No. 1 to 1584, as presented in the claims for example are also included. Within the sense of the invention, homologues are those with homology of the amino or nucleic acid sequence and those in which the corresponding sequence is modified, for example the protein variants, which indeed have the same amino acid sequence, but differ with regard to the modification, in particular the post-translational modification.

In accordance with the invention, modifications of the nucleic acid sequence and of the amino acid sequence, for example citrullination, acetylation, phosphorylation, glycosylation, ethylation, or polyA strand extensions and further modifications known as appropriate to a person skilled in the art are included.

Homologues also include sequence homologues of the markers and subsequences thereof. Sequence homologues are, for example, nucleic acid sequences and/or protein sequences that have an identity with the SLE markers of the sequences SEQ ID No. 1 to 1584 of at least 70% or 80%, preferably 90% or 95%, particularly preferably 96% or 97% or more, for example 98% or 99%. In a particularly preferred embodiment of the invention, for the case in which the SLE markers are antigens, the homology in the sequence range in which the antigen-antibody or antigen-autoantibody interaction takes place, is at least 95%, preferably at least 97%, particularly preferably at least 99%. For example, mutations such as base exchange mutations, frameshift mutations, base insertion mutations, base loss mutations, point mutations and insertion mutations, are included in accordance with the invention.

The invention also relates to subsequences of the SLE markers with the sequence SEQ ID No. 1 to 1584. Subsequences also include nucleic acid or amino acid sequences that are shortened compared with the entire nucleic acid or the entire protein/peptide. Here, the deletion may occur at the end or the ends and/or within the sequence. For example, subsequences and/or fragments that have 50 to 100 nucleotides or 70-120 nucleotides of the sequence SEQ ID No. 1 to 1584 are included. Homologues of subsequences are also included in accordance with the invention. In a particular embodiment, the SLE markers are shortened compared with the sequences SEQ ID No. 1 to 1584 to such an extent that they still consist only of the binding point(s) for the SLE-associated autoantibody in question. In accordance with the invention, SLE markers are also included that differ from the sequences SEQ ID No. 1 to 1584 in that they contain one or more insertions, wherein the insertions for example are 1 to 100 or more nucleotide/amino acids long, preferably 5 to 50, particularly preferably 10 to 20 nucleotides/amino acids long and the sequences are otherwise identical however or homologous to sequences SEQ ID No. 1 to 1584. Subsequences that have at least 90%, preferably at least 95%, particularly preferably 97% or 98%, of the length of the SLE markers according to the invention with sequences SEQ ID No. 1 to 1584 are particularly preferred.

In a further embodiment, the respective SLE marker can be represented in different quantities in one or more regions in the arrangement or on the substrate or in a panel. This allows a variation of the sensitivity. The regions may each have a totality of SLE markers, that is to say a sufficient number of different SLE markers, in particular 2, 3, 4, 5, 6, 7, 8, 9 or 10 or more different SLE markers. By way of example, 20 to 50 (numerically) or more, preferably more than 100, particularly preferably 150 or more, for example 25,000 or 5000 or 10000 different or same SLE marker sequences and where applicable further nucleic acids and/or proteins, in particular other biomarkers can be represented on the substrate or in the panel.

One or more panels as presented in the examples and selected from the sequences, preferably protein sequences, consisting of at least two markers, five markers or 10 markers or more, selected from:

panel I (P1)

SEQ ID No. 1, 2, 3, 5, 7, 8, 10, 12, 13, 15, 17, 18, 19, 20, 24,

SEQ ID No. 528, 529, 530, 532, 534, 535, 537, 539, 540, 542, 544, 545, 546, 547, 551, preferably SEQ ID No. 1057, 1058, 1059, 1061, 1063, 1064, 1066, 1068, 1069, 1071, 1073, 1074, 1075, 1076, 1080, and/or panel II (P2)

SEQ ID No. 1, 3, 4, 5, 7, 12, 13, 14, 15, 17, 18, 19, 20, 24

SEQ ID No. 528, 530, 531, 532, 534, 539, 540, 541, 542, 544, 545, 546, 547, 551, preferably SEQ ID No. 1057, 1059, 1060, 1061, 1063, 1068, 1069, 1070, 1071, 1073, 1074, 1075, 1076, 1080, and/or panel III (P3)

SEQ ID No. 1, 2, 3, 5, 6, 7, 8, 9, 10, 15, 16, 18, 21, 23

SEQ ID No. 528, 529, 530, 532, 533, 534, 535, 536, 537, 542, 543, 545, 548, 550, preferably SEQ ID No. 1057, 1058, 1059, 1061, 1062, 1063, 1064, 1065, 1066, 1071, 1072, 1074, 1077, 1079, and/or panel IV (P4)

SEQ ID No. 1, 2, 3, 4, 5, 8, 9, 10, 12, 13, 14, 15, 17, 19, 20

SEQ ID No. 528, 529, 530, 531, 532, 533, 536, 537, 539, 540, 541, 542, 544, 546, 547, preferably SEQ ID No. 1057, 1058, 1059, 1060, 1061, 1064, 1065, 1066, 1068, 1069, 1070, 1071, 1073, 1075, 1076, and/or panel V SEQ ID No. 1, 2, 3, 4, 5, 6, 7, 11, 15, 16, 18, 21, 22, 23, 24

SEQ ID No. 528, 529, 530, 531, 532, 533, 534, 538, 542, 543, 545, 548, 549, 550, 551, preferably SEQ ID No. 1057, 1058, 1059, 1060, 1061, 1062, 1063, 1067, 1071, 1072, 1074, 1077, 1078, 1079, 1080, and/or panel VI SEQ ID No. 2, 5, 6, 7, 8, 10, 13, 18, 19, 22, 168

SEQ ID No. 529, 532, 533, 534, 535, 537, 540, 545, 546, 549, 695, preferably

SEQ ID No. 1058, 1061, 1062, 1063, 1064, 1066, 1069, 1074, 1075, 1078, 1224, and/or panel VII SEQ ID No. 1, 2, 5, 6, 7, 8, 9, 10, 13, 15, 19, 22, 24, 134, 168, 213, 367, 368, 369

SEQ ID No. 528, 529, 532, 533, 534, 535, 536, 537, 540, 542, 546, 549, 551, 661, 695, 741, 895, 896, 897, preferably SEQ ID No. 1057, 1058, 1061, 10642, 1063, 1064, 1065, 1066, 1069, 1071, 1075, 1078, 1080, 1190, 1224, 1270, 1424, 1425, 1426, and/or panel VIII (P8)

SEQ ID No. 1, 2, 4, 5, 6, 7, 8, 9, 10, 12, 13, 15, 17, 18, 19, 20, 21, 22, 23, 24, 29, 31, 46, 95, 128, 134, 136, 143, 163, 168, 169, 171, 188, 213, 348, 367, 368, 369, 370-391, 423-433

SEQ ID No. 528, 529, 531, 532, 533, 534, 535, 536, 537, 539, 540, 542, 544, 545, 546, 547, 548, 549, 550, 551, 556, 558, 573, 622, 655, 661, 663, 690, 695, 696, 698, 715, 741, 876, 895, 896, 897, 898-919, 951-961, preferably SEQ ID No. 1057, 1058, 1060, 1061, 1062, 1063, 1064, 1065, 1066, 1068, 1069, 1071, 1073, 1074, 1075, 1076, 1077, 1078, 1079, 1080, 1085, 1087, 1102, 1151, 1184, 1190, 1192, 1219, 1220, 1224, 1225, 1227, 1244, 1270, 1405, 1424, 1425, 1426, 1427-1448, 1480-1490, and/or panel IX (P9)

SEQ ID No. 1, 2, 3, 4, 5, 6, 7, 8, 9, 10, 11, 12, 13, 14, 15, 16, 17, 18, 19, 20, 21, 22, 23, 24, 29, 31, 33, 41, 46, 48, 74, 95, 105, 108, 114, 115, 116, 128, 132, 134, 136, 143, 163, 168, 169, 171, 188, 213, 348, 367, 368, 369, 370-391, 423-433

SEQ ID No. 528, 529, 530, 531, 532, 533, 534, 535, 536, 537, 538, 539, 540, 541, 542, 543, 544, 545, 546, 547, 548, 549, 550, 551, 556, 558, 560, 568, 573, 575, 601, 622, 632, 635, 641, 642, 643, 655, 659, 661, 663, 670, 690, 695, 696, 698, 715, 741, 876, 895, 896, 897, 898-919, 951-961, preferably SEQ ID No. 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1085, 1087, 1089, 1097, 1102, 1104, 1130, 1151, 1161, 1164, 1170, 1171, 1172, 1184, 1188, 1190, 1192, 1199, 1219, 1224, 1225, 1227, 1244, 1270, 1405, 1424, 1425, 1426, 1427-1448, 1480-1490 or respective homologues or subsequences thereof, as mentioned previously with regard to the individual marker sequences, is/are very particularly preferred.

These aforementioned panels particularly advantageously allow the execution of the method according to the invention; see the examples.

Within the scope of this invention, "arrangement" is synonymous with "array", and, if this "array" is used to identify substances on SLE markers, this is to be understood preferably to be an "assay" or a bead or a diagnostic device or a screening assay. In a preferred embodiment, the arrangement is designed such that the markers represented on the arrangement are present in the form of a grid on a substrate. Furthermore, those arrangements are preferred that permit a high-density arrangement of SLE markers. The markers are preferably spotted. Such high-density spotted arrangements are disclosed for example in WO 99/57311 and WO 99/57312 and can be used advantageously in a robot-supported automated high-throughput method.

Within the scope of this invention, however, the term "assay" or diagnostic device likewise comprises those embodiments such as ELISA, bead-based assay, line assay, Western Blot, and immunochromatographic methods (for example what are known as lateral flow immunoassays) or similar immunological single or multiplex detection methods.

A "protein array" in the sense of this invention is the systematic arrangement of SLE markers on a solid substrate, wherein the substrate can have any shape and/or size, and wherein the substrate is preferably a solid substrate.

The SLE markers of the arrangement/panel are fixed on the substrate, preferably spotted or immobilised, printed on or the like, in particular in a reproducible manner. One or more SLE markers can be present multiple times in the totality of all SLE markers and may be present in different quantities based on a spot. Furthermore, the SLE markers can be standardised on the substrate (for example by means of serial dilution series of, for example, human globulins as internal calibrators for data normalisation and quantitative evaluation). A standard (for example a gold standard) can also be applied to the substrate where necessary.

In a further embodiment, the SLE markers are present as clones. Such clones can be obtained for example by means of a cDNA expression library according to the invention. In a preferred embodiment, such expression libraries are obtained using expression vectors from a cDNA expression library comprising the cDNAs of the SLE-specific marker sequences. These expression vectors preferably contain inducible promoters. The induction of the expression can be carried out for example by means of an inducer, such as IPTG. Suitable expression vectors are described in Terpe et al. (Terpe T Appl Microbiol Biotechnol. 2003 January; 60(5):523-33).

Expression libraries are known to a person skilled in the art; they can be produced in accordance with standard works, such as Sambrook et al, "Molecular Cloning, A laboratory handbook, 2nd edition (1989), CSH press, Cold Spring Harbor, N.Y. Expression libraries that are tissue-specific (for example human tissue, in particular human organs) are furthermore preferable. Further, expression libraries that can be obtained by means of exon trapping are also included in accordance with the invention.

Protein arrays or corresponding expression libraries that do not exhibit any redundancy (what is known as a Uni-clone® library) and that can be produced for example in accordance with the teaching of WO 99/57311 and WO 99/57312 are furthermore preferred. These preferred Uni-clone® libraries have a high proportion of non-defective fully expressed proteins of a cDNA expression library.

Within the scope of this invention, the clones can also be, but are not limited to, transformed bacteria, recombinant phages or transformed cells of mammals, insects, fungi, yeasts or plants.

The clones are fixed, spotted or immobilised on a solid substrate. The invention therefore relates to an arrangement/use, wherein the SLE-specific markers are present as clones.

In addition, the SLE markers can be present in the respective form in the form of a fusion protein, which for example contains at least one affinity epitope or "tag", wherein the tag is selected for example from c-myc, his tag, arg tag, FLAG, alkaline phosphatase, V5 tag, T7 tag or strep tag, HAT tag, NusA, S tag, SBP tag, thioredoxin, DsbA, or the fusion protein has one or more additional domains for example, such as a cellulose-binding domain, green fluorescent protein, maltose-binding protein, calmodulin-binding protein, glutathione S-transferase or lacZ.

In a further embodiment the invention relates to an assay, for example a multiplex assay, a bead-based assay, or protein array for identifying and characterising a substance, for example a hit, a lead substance, or an active substance for SLE. Here, a substance to be tested is used. This can be any native or non-native biomolecule, a (synthetic) chemical molecule, a natural substance, a mixture or a substance library. Once the substance to be tested has contacted an SLE marker, the binding success is evaluated, for example with use of commercially available image-analysis software (GenePix Pro (Axon Laboratories), Aida (Raytest), ScanArray (Packard Bioscience).

Binding according to the invention, binding success, interactions, for example protein-protein interactions (for example protein to SLE marker, such as antigen/antibody) or corresponding "means for detecting the binding success" can be visualised for example by means of fluorescence labelling, biotinylation, radio-isotope labelling or colloid gold or latex particle labelling in the conventional manner. Bound antibodies are detected with the aid of secondary antibodies, which are labelled using commercially available reporter molecules (for example Cy, Alexa, Dyomics, FITC or similar fluorescent dyes, colloidal gold or latex particles), or with reporter enzymes, such as alkaline phosphatase, horseradish peroxidase, etc. and the corresponding colorimetric, fluorescent or chemoluminescent substrates. A read-out is performed for example by means of a microarray laser scanner, a CCD camera or visually.

In a further embodiment, the invention relates to a drug or an active substance or prodrug for SLE, developed and obtainable by the use of an SLE marker according to the invention.

The invention also relates to the use of an SLE marker selected from sequences SEQ ID No. 1 to 1584 and subsequences of SEQ ID No. 1 to 1584 with at least 90%, preferably at least 95% of the length of SEQ ID No. 1 to 1584 and homologues of SEQ ID No. 1 to 1584 and subsequences thereof with an identity of at least 95%, preferably at least 98% or more, to the corresponding sequences and proteins/peptides coded by the sequences SEQ ID No. 1 to 1056, coded by the subsequences thereof and homologues as affinity material for carrying out an apheresis or blood washing for patients with SLE, i.e. apheresis of SLE autoantibodies. The invention thus relates to the use of the markers according to the invention, preferably in the form of an arrangement, as affinity material for carrying out an apheresis or a blood washing in the broader sense, wherein substances from bodily fluids from a patient with SLE, such as blood or plasma, bind to the markers according to the invention and consequently can be removed selectively from the bodily fluid. The application in blood washing is a special case of use of the SLE markers as a target. Devices for carrying out a blood washing, in particular immunapheresis, are known to a person skilled in the art and can be carried out for example by means of dialysis.

The following examples and drawings explain the invention, but do not limit the invention to the examples.

Figure 3:
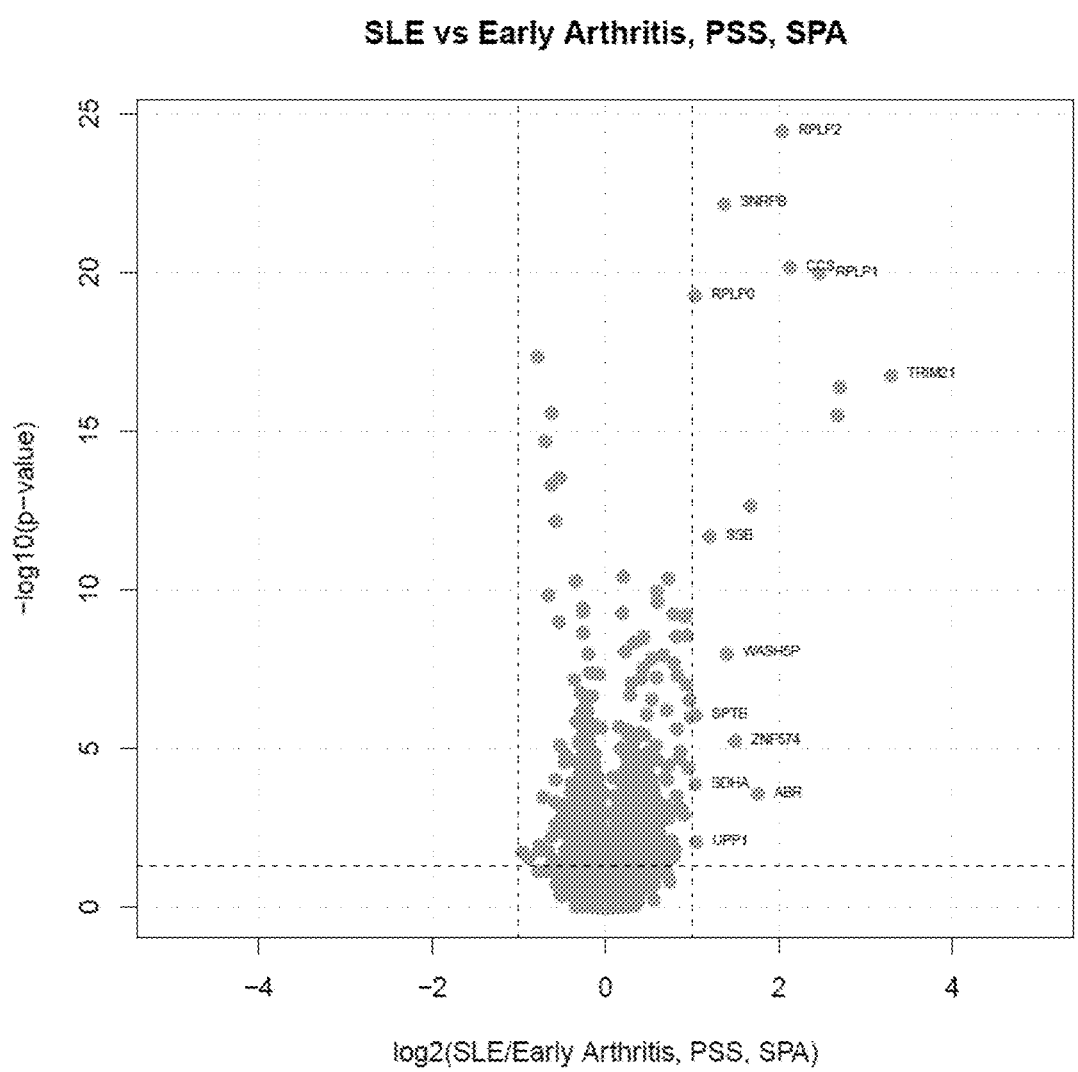

FIG. 3: volcano plot of the antigen reactivities of SLE patients compared with a combined group of patients with various autoimmune diseases, such as SSc (PSS), SPA, early rheumatoid arthritis and SPA.

Figure 4:
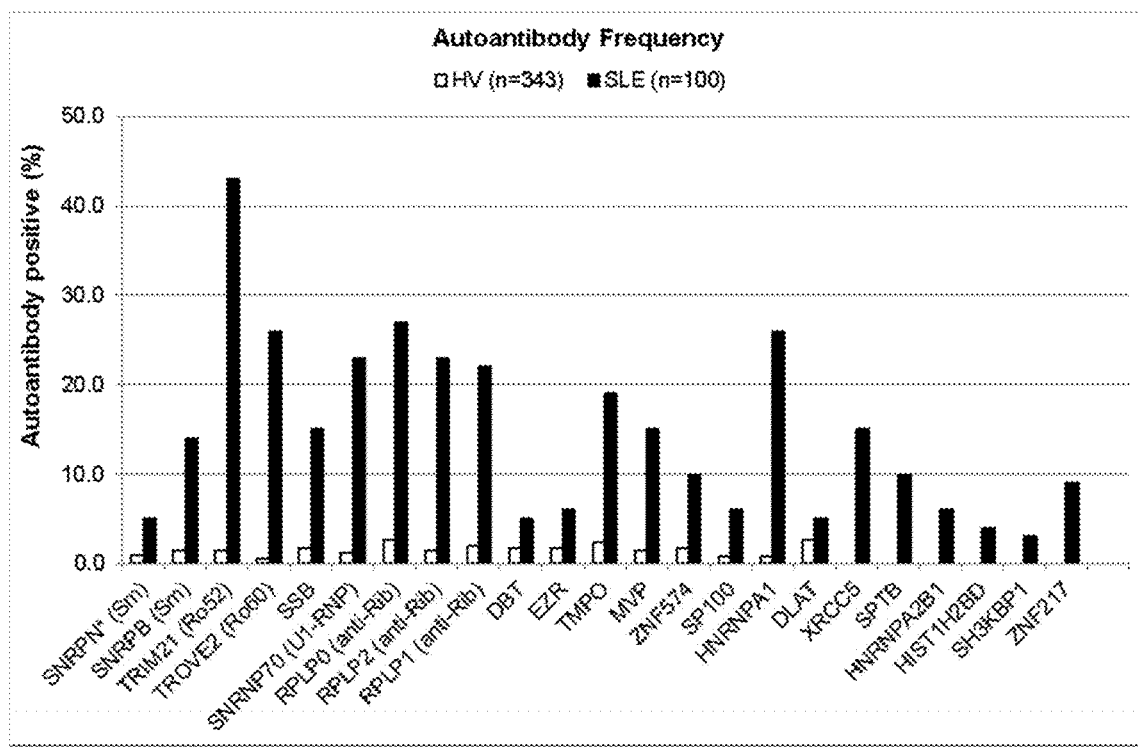

FIG. 4 frequency of the autoantibody reactivities of selected antigens in SLE patients and healthy test subjects. A threshold value of 3 SD deviations above the mean value of the healthy test subject was applied. The threshold value for the antigen SNRNP was set to 2SD.

Figure 5:
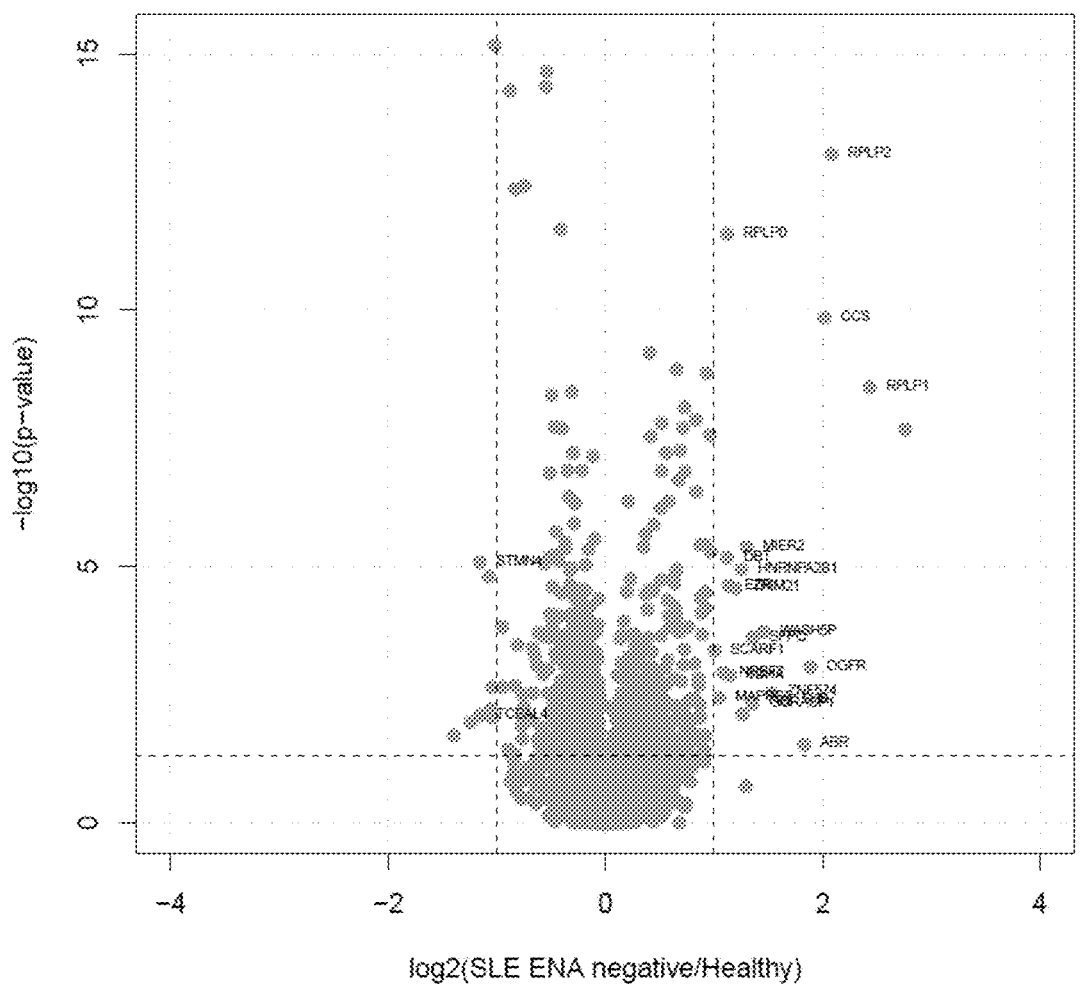

FIG. 5: volcano plot of the autoantibody reactivities of ENA-4-negative SLE patients compared with healthy controls.

Figure 6:
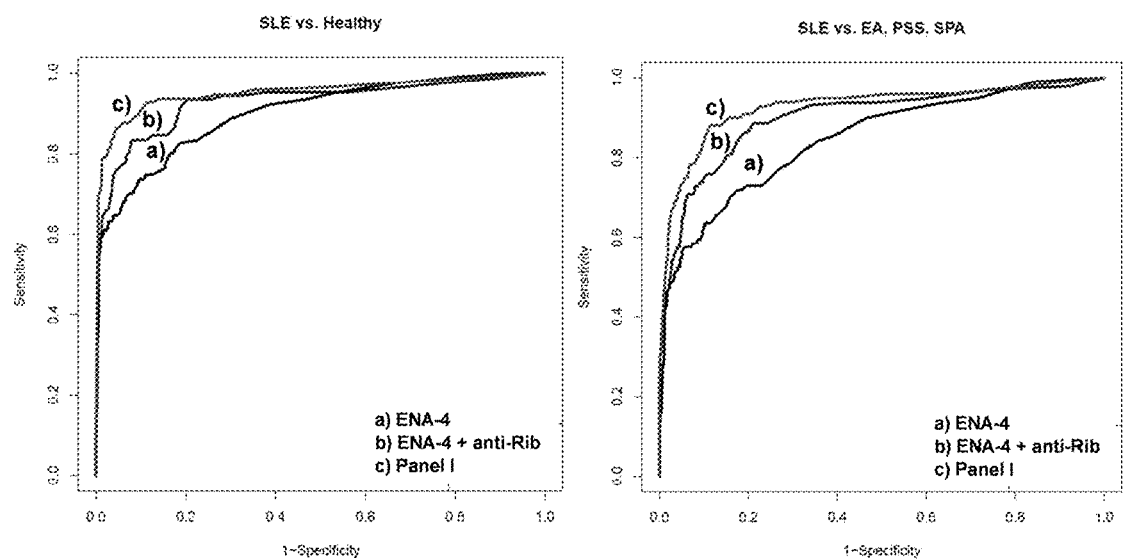
Figure 7:
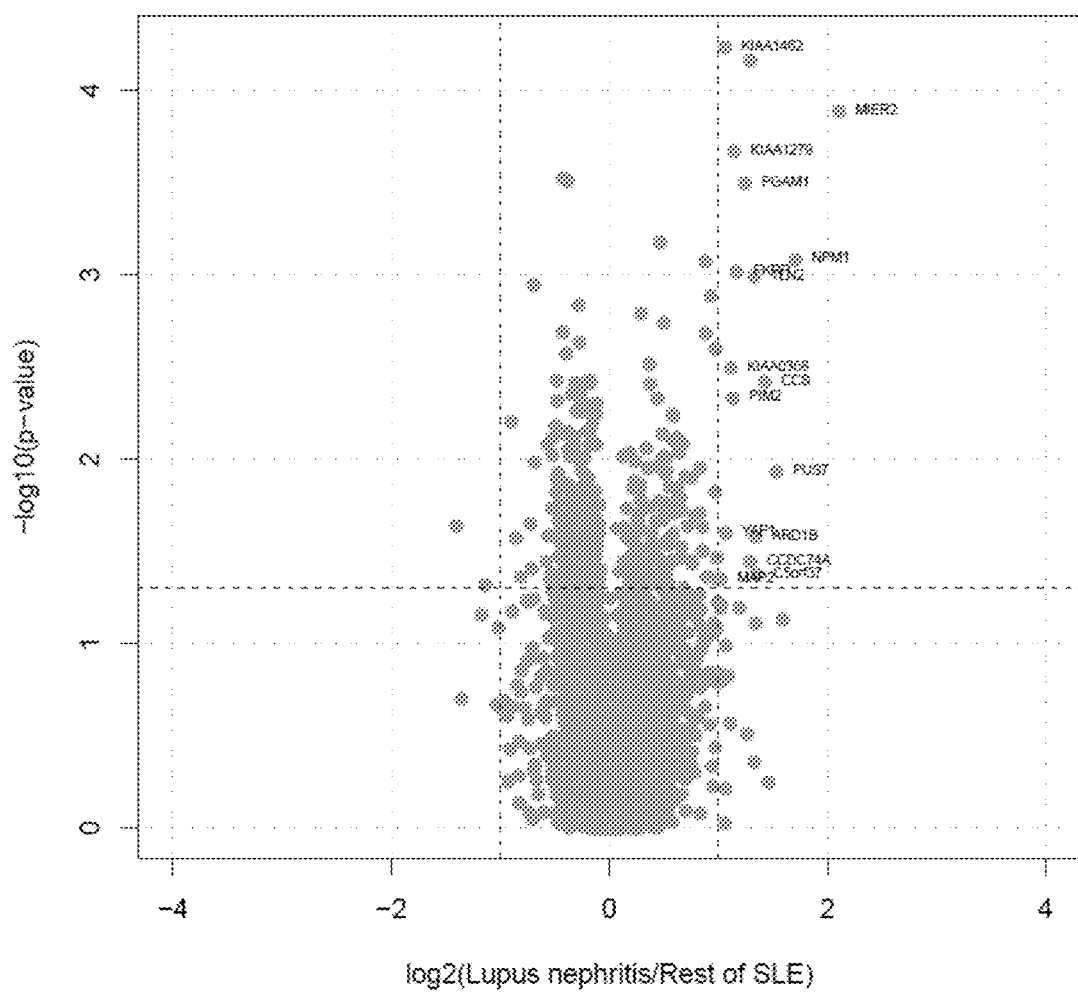
Figure 8:
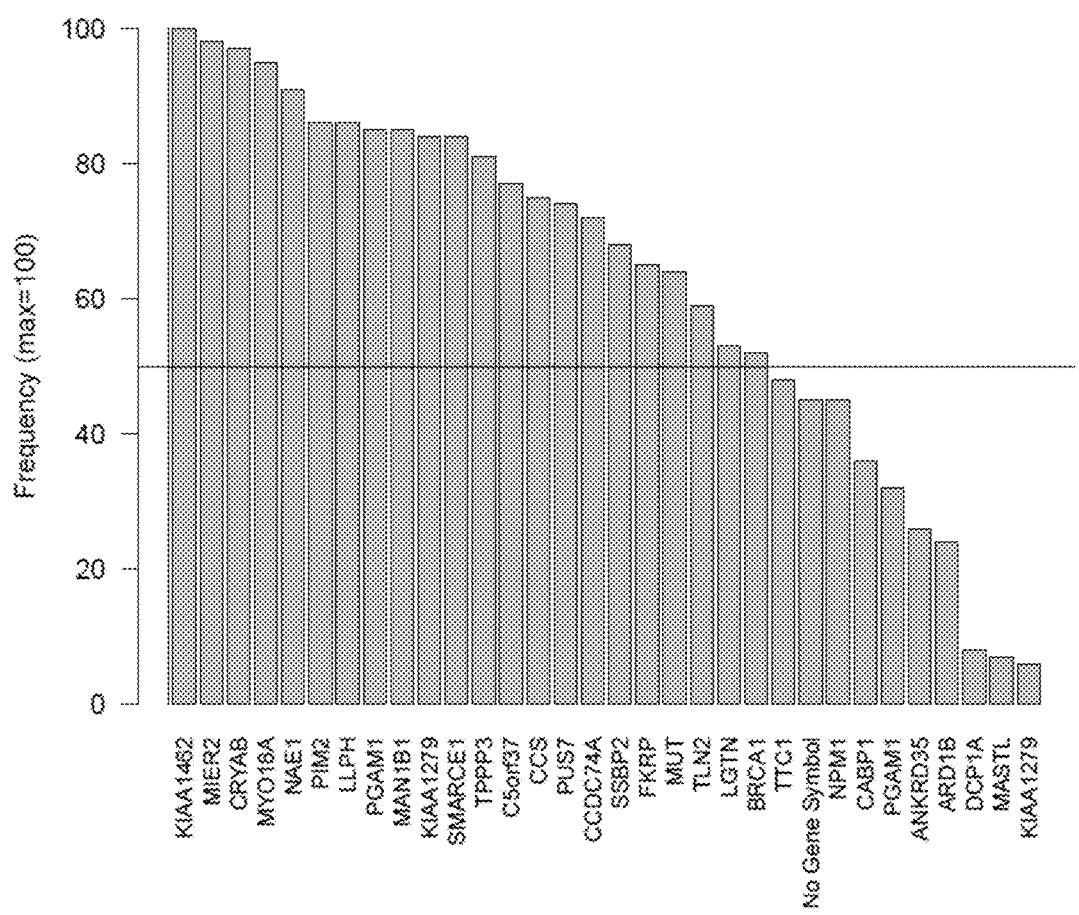

FIG. 6: receiver operating characteristic curves (ROCs) for the diagnosis of SLE compared to healthy test subjects and AID samples FIG. 7: volcano plot for SLE lupus nephritis compared with SLE without lupus nephritis FIG. 8: frequency of the lupus nephritis antigens in a model with nested cross validation.

Figure 9:
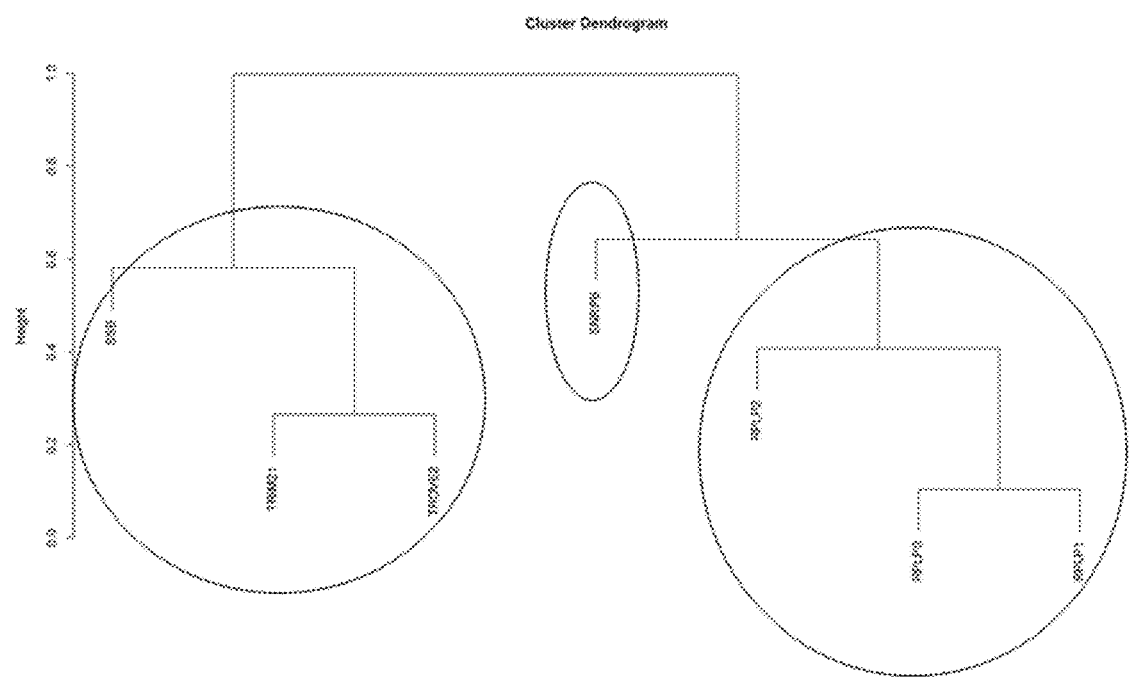
Figure 9:
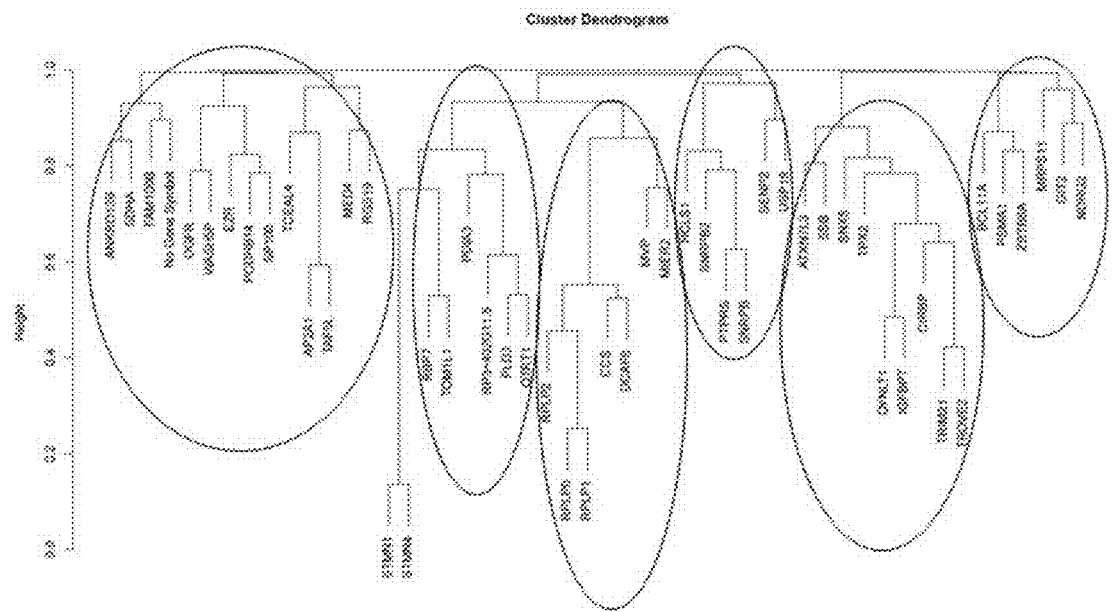

FIG. 9: dendogram of the SLE antigens following calculation of Spearman's rank correlation coefficient a) dendogram of the known ENA-4 antigens and b) dendogram of 50 selected SLE antigens.

FIG. 10: PPLS-DA biplot of the SLE patients and healthy controls with use of the SLE antigens a) PPLS-DA biplot based on the ENA-4 and ribosomal antigen b) PPLS-DA biplot based on 50 SLE antigens.

EXAMPLES

Example 1

Selection of the SLE Patients and Test Subjects

Selection of the patient groups to be tested: Blood samples were analysed from 129 SLE patients, 100 patients with systemic sclerosis (SSc, PSS), 75 patients with rheumatoid arthritis (RA), 537 patients with early RA (period of disease less than 6 months) and 75 patients with ankylosing spondylitis (SPA)/Bekhterev's disease (SPA). 343 blood samples from the Bavarian Red Cross (BRC) were used as control group. An informed consent of the Ethics Commission of the clinical partners and of the biobank of the BRC was received from all test subjects.

TABLE 1

Patient samples and clinical data (test cohort I)

| | 1. Screen | | | 2. Screen | | | | | |
|---|---|---|---|---|---|---|---|---|---|
| | | | | SLE | SSc (PSS) | | Early RA | | |
| | SLE | RA | Healthy | SLE | Total | Sub-type | (<6 months) | SPA | Healthy |
| Number | 129 | 75 | 123 | 100 | 100 | | 537 | 82 | 343 |
| Age (years) | 39 +/− 12 | 56.6 +/− 13.2 | 41.3 +/− 11 | 39.8 +/− 11.9 | 56.9 +/− 13.4 | Limited n = 50 | 56.8 +/− 14.3 | 43.7 +/− 10.1 | 47.7 +/− 11.7 |
| % female | 86.1 | 72 | 86.2 | 83 | 87 | Diffuse n = 32 | 62.2 | 15.9 | 58.3 |
| % ANA | 77.5 | N.D. | N.D. | 100 | 95 | Overlap n = 9 | N.D. | N.D. | N.D. |
| SLAM | 7.7 +/− 5.1 | | | 7.7 +/− 5.1 | | | | | |
| SLICC | 1.45 +/− 1.8 | | | 1.45 +/− 1.8 | | | | | |
| ANA % | | | | | | | | | |
| ENA-4 positive % | 37 | | | 48 | | | | | |
| U1-RNP (% of ENA-4 pos.) | 13 | | | 13 | | | | | |
| Sm (% of ENA-4 pos.) | 8 | | | 8 | | | | | |
| SS-A/Ro52 (% of ENA-4 pos.) | 35 | | | 35 | | | | | |
| SS-B/Ro60 (% of ENA-4 pos.) | 10 | | | 10 | | | | | |
| Kidney involvement % | 26.4 | | | 34 | | | | | |

Example 2

Antigen Production

Five cDNA libraries that had been produced from different human tissues (foetal brain, intestine, lung, liver and T-cells) were used for the production of the recombinant antigens. All cDNAs were expressed in *E. coli* under the transcriptional control of the lactose-inducible promoter. The resultant proteins carry, at their amino terminus, an additional sequence for a hexahistidine purification tag (His6 tag). Target antigens which were not present in the cDNA library were produced by chemical synthesis (Life Technologies) and cloned into the expression vector pQE30-NST, which already codes an amino-terminal His6 tag.

Following recombinant expression of the proteins, these were isolated in denaturising conditions and purified by means of metal affinity chromatography (IMAC). The proteins were lyophilised and stored at −20° C. until further use (lifesciences.sourcebioscience.com).

Example 3

Production of the BBAs

The production of BBAs was adapted to a microtitre plate format, such that 384 coupling reactions could be assessed in parallel using automated pipette systems (Starlet, Hamilton Robotics, Evo Freedom 150, Tecan). For the use of automated pipette systems, the individual bead regions were transferred into coupling plates (96 well Greiner) and the antigens were transferred into 2D barcode vessels (Thermo Scientific). For each coupling reaction, 0.6 to 2.5 million beads and, depending on the antigen, 1 to 100 µg protein were used.

All washing and pipetting steps of the coupling reaction were carried out in coupling plates which were fixed on magnets.

The beads were washed twice with 100 µl LxAP buffer (100 mM NaH2PO4, pH 6.2) and then received in 120 µl LxAP buffer. For the activation, 15 µl 1-ethyl-3-(3-dimethylaminopropyl)carbodiimide (EDC; 50 mg/ml) and 15 µl N-hydroxysulfosuccinimide (sulfo-NHS; 50 mg/ml) were added by pipette to form a bead suspension, and these suspensions were then incubated for 20 minutes in the shaker (RT, 900 rpm, protected against light). The beads were then washed 3× with 150 µl LxKPT buffer and then the protein solution was added. Following an incubation period of two hours in the shaker (RT, 900 rpm, protected against light), the beads were then washed three times with 150 µl LxKPT buffer. To block free binding points, 100 µl LxCBSP buffer (PBS, 1% BSA, 0.05% ProClin300) were added, and these mixtures were then incubated for 20 min in the shaker (RT, 900 rpm, protected against light). This was followed by incubation over night at 4-8° C. The BBA was produced by the combination of beads coupled to antigens and was stored at 4-8° C., protected against light, until use.

Example 4

Quality Control of the BBAs

In order to check the immobilisation of the proteins at the respective bead regions, a coupling control was carried out.

Here, different amounts of beads were used (250, 500 and 750 beads per bead region). For a reaction mixture, 500 beads for example per bead region were diluted in LxCBS buffer (PBS, 1% BSA) and transferred into an assay plate (96 well half area microplate, Greiner).

Before each washing step, the assay plate with the beads was placed for 2 minutes on a magnet and the supernatant was then removed. After three washing steps, the beads were incorporated with 100 µl LxWPT buffer (PBS, 0.05% Tween-20), and 10 µg/ml penta-his antibodies (Qiagen) or LxCBS buffer (PBS, 1% BSA) were added by pipette. Following incubation for 45 minutes in the shaker (RT, 900 rpm, protected against light), the supernatant was removed and the beads were washed in two steps. 5 µg/ml goat anti-mouse IgG-PE (Phycoerythrin) or goat anti-human IgG-PE (Dianova) were then added as secondary antibody to the reaction mixture and incubated for 30 minutes. Following two washing steps, 100 µl of carrier liquid (Luminex) was added to the beads. The fluorescence signal of the beads was detected with the aid of the FlexMAP3D instrument. Here, the bead count on the one hand and the median of the fluorescence intensity (MFI value) on the other hand were measured.

Example 5

Application of BBAs

For application, BBAs were incubated with sera and all IgG-based autoantibodies bonded to antigens were detected with the aid of a secondary antibody. In order to enable a high throughput of measurements, the application of BBAs was adapted to a microtiter plate format so that either an 8-channel (Starlet, Hamilton Robotics) or a 96-channel (Evo Freedom 150, Tecan) automated pipetting system could be used. The sera to be examined were transferred into 2D barcode vessels and then diluted 1:100 with assay buffer (PBS, 0.5% BSA, 10% E. coli lysate, 50% low-cross buffer (Candor Technologies)). In order to neutralise human antibodies directed against E. coli, a pre-incubation of the sera dilutions was performed for 20 min. In this time, 500 beads per bead region were distributed in the assay plate. 50 µl of diluted serum were added to the beads in the coupling plate, and the reaction mixtures were incubated for 18-22 h in the shaker (4-8° C., 900 rpm, protected against light). After three washing steps in each case with 100 µl LxWPT buffer, 5 µg/ml of the detection antibody goat anti-human IgG-PE (Dianova) were added to the reaction mixtures and incubated for 1 h in the shaker (RT, 900 rpm). The beads were then washed three times with 100 µl LxWPT and incorporated in 100 µl carrier liquid (Luminex). The fluorescence signal of the beads was detected with the aid of the FlexMAP3D instrument. Here, the bead count on the one hand and the MFI value (median fluorescence intensity) on the other hand were measured.

Example 6

Biostatistical Analysis

The biostatistical analysis comprised univariate and multivariate methods for describing the statistical properties of individual antigens and of groups of antigens. In order to discover interesting candidates for panels, the key property was a good separation between the groups of samples based on the MFI values. In order to find antigen candidates for panel generation, univariate testing, receiver operating characteristic (ROC) analyses, correlation profiles, powered partial least squares discriminant analysis (PPLS-DA) and random forests were used as methods. Biostatistical analyses were subject to expert assessment in order to define final antigen panels.

Before the statistical analysis, the MFI values were log 2-transformed in order to reduce the skew in the distributions. If more than 20% of the values were missing, antigens were excluded from the analysis. Missing values were replaced by median imputation. A quantile normalisation was carried out under consideration of the reference sera in order to normalise, per BBA set, all measured samples on individual plates.

Besides descriptive standardisation for MFI values, non-parametric tests were also carried out with the aid of the two-sided Mann-Whitney-U test in order to uncover differences in the median values of the groups. The test level for multiple testing was corrected in accordance with the Bonferroni-Holm procedure. In addition, the Benjamin-Hochberg procedure inclusive of the determination of the False Discovery Rate (FDR, q-value) was applied. In addition, fold-change and effect size were determined. In order to assess the classification quality, an ROC analysis was carried out, within the scope of which sensitivity, specificity and the area under the ROC curve (AUC) were calculated, in each case inclusive of the 95% confidence interval on the basis of the bootstrap method. Boxplots and volcano plots were used for graphical representation. A scoring system was implemented on the basis of the univariate results.

By means of the application of a PPLS-DA, it was attempted to maximise the correlation between the component of the response matrix. A linear discriminant analysis with the latent component as predictors was used for the final classification. A random forest was applied, in which binary decision trees are combined. The decision trees were formed on the basis of a number of bootstrap samples of a training sample and by random selection of a subgroup of explaining variables at each node. The number of input variables, which was selected randomly with each division step, was determined as the square root of the total number of variables, and the number of trees in the random forest was set to 1000. A cross validation with 500 times throughput was implemented for both multi-variant approaches.

Example 7

Autoantibodies/Antigen Reactivities Differentiate SLE from Healthy Controls, Rheumatoid Arthritis and Other Autoimmune Diseases In a first screening the antigen reactivities of 129 SLE patients, 75 RA patients, and 134 healthy controls categorised in accordance with age and sex were differentially tested. For this purpose, the autoantibody reactivities of these blood samples were tested on 5857 antigens coupled to Luminex beads.

Figure 1:
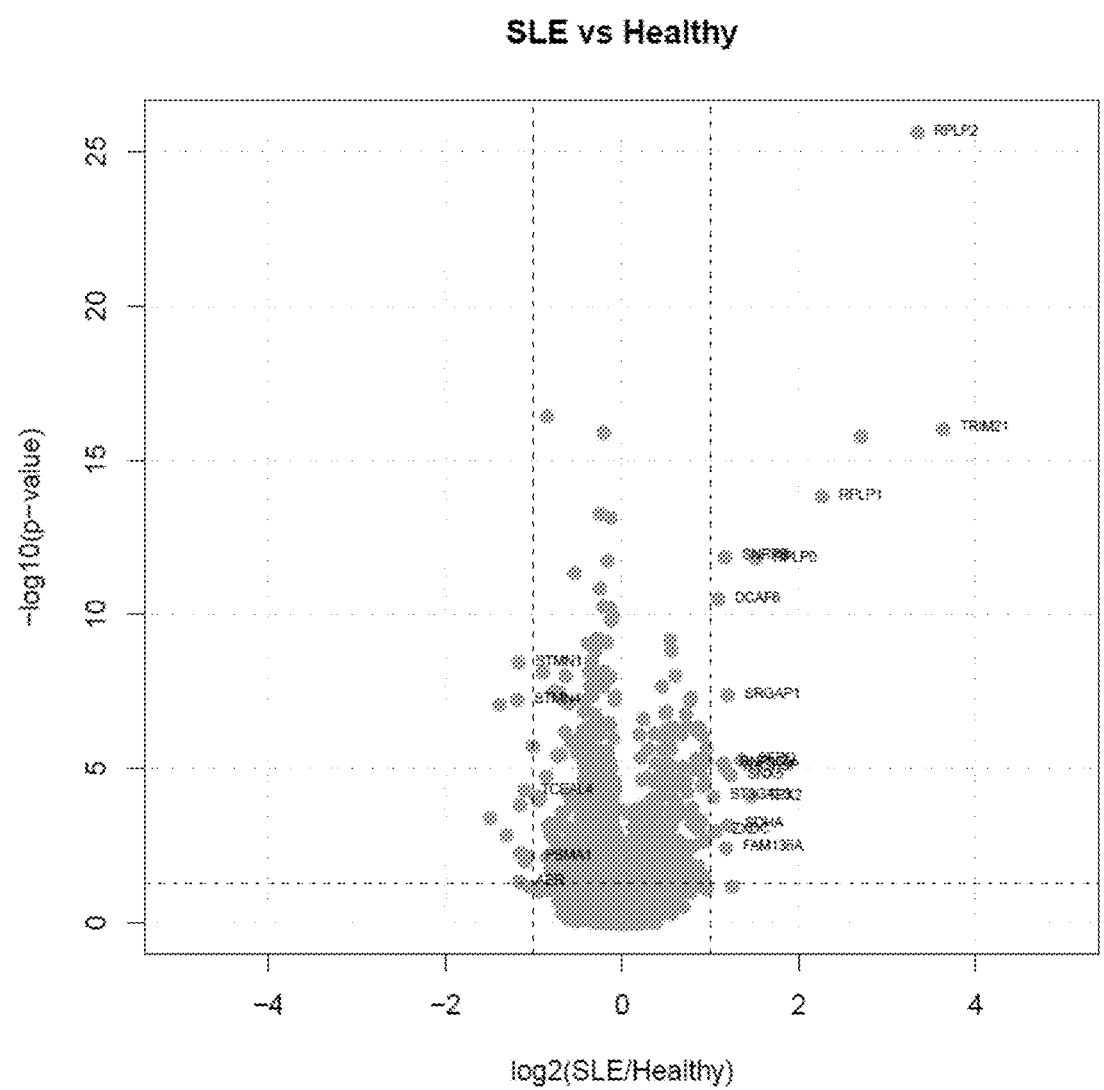
FIG. 1 shows a volcano plot of the relative antigen reactivities of the SLE patients compared to healthy controls.
Figure 2:
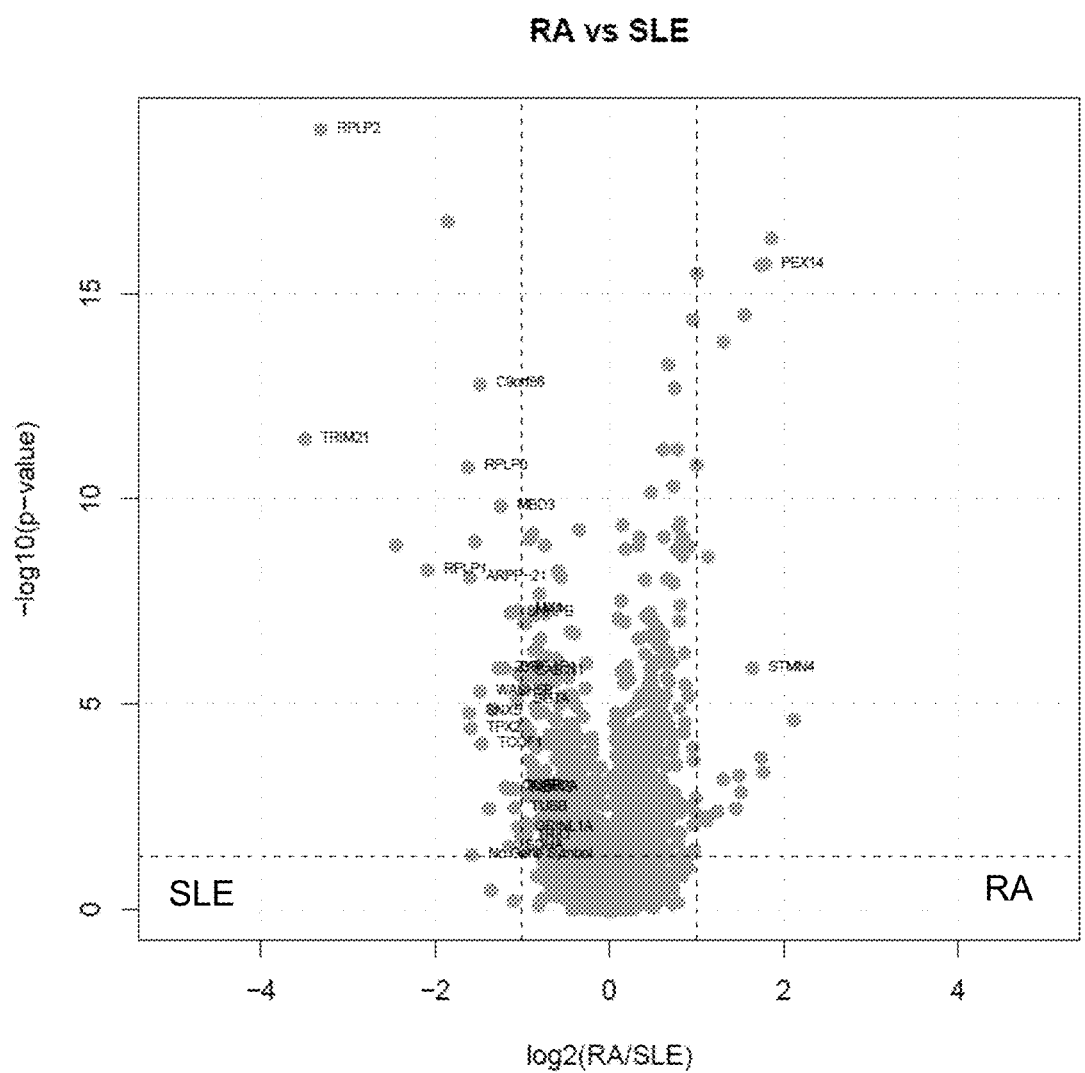
FIG. 2 shows a volcano plot of the relative antigen reactivities of the SLE patients compared to RA patients.

In order to identify antigens with which the group of all SLE patients can be distinguished from different control groups consisting of healthy samples and patients with RA, univariate statistical tests were carried out. The result of the statistical test is illustrated as a volcano plot for all 5857 antigens. In the volcano plot, the x-axis shows the relative change of the antigen reactivity in SLE patients compared with healthy controls (FIG. 1) and RA patients (FIG. 2). The y-axis presents the p-value of the statistical tests. FIGS. 1 and 2 show that specific autoantibody reactivities were found which are increased in the group of all SLE and which can distinguish both from healthy donors and from RA patients.

Example 8

Autoantibodies/Antigen Reactivities Differentiate SLE from Healthy Controls, Early Rheumatoid Arthritis and Other Autoimmune Diseases In a second screening with 6088 antigens, the antigens which differentiate between healthy controls and donors with rheumatoid arthritis were tested on patients with early rheumatoid arthritis, SSc and SPA. This is of importance in particular since patients with collagenoses and mixed collagenoses have an overlapping autoantibody profile and therefore are difficult to diagnose, particularly in the early phase.

FIG. 3 shows a volcano plot of the antigen reactivities of SLE patients against a combined group of patients with various autoimmune diseases, such as SSc, SPA, early rheumatoid arthritis, and SPA.

Following univariate statistical evaluation, a threshold value of $p<0.05$ and a 1.5 times modified reactivity compared with the control group were applied. A final list of antigen reactivities over both screens was established (Table 2).

In order to analyse the frequency of the newly identified antigens in comparison with known antigens, a threshold value of 3 standard deviations (SD) above the mean value of the healthy samples was defined.

Astonishingly, at least 4 additional antigens were identified of which the frequency in SLE patients lies above 15%. These include TMPO (19%) (SEQ ID No. 18), HNRNPA1 (26%) (SEQ ID No. 5), XRCC5 (15%) (SEQ ID No. 22) and MVP (15%) (SEQ ID No. 7).

FIG. 4 shows the frequency of 23 antigens in comparison to the healthy controls.

Table 2 summarises the identified antigen reactivities and different group comparisons.

TABLE 2

List of all antigen reactivities

| SEQ ID No. | GeneID | Gene Symbol | Gene Name | Group | Panel SLE | Panel L. Nephr. | SLE Cluster | Statistical Test ENA-4 neg vs HV | L. Nephr. vs SLE | SLE vs control |
|---|---|---|---|---|---|---|---|---|---|---|
| 1 | 1629 | DBT | dihydrolipoamide branched chain transacylase E2 | 1 | x | | | x | | SLE vs AID |
| 2 | 1737 | DLAT | dihydrolipoamide S-acetyltransferase | 1 | x | | | | | SLE vs AID |
| 3 | 7430 | EZR | ezrin | 1 | x | | x | x | | SLE vs AID |
| 4 | 3017 | HIST1H2BD | histone cluster 1, H2bd | 1 | x | | | x | | SLE vs AID |
| 5 | 3178 | HNRNPA1 | heterogeneous nuclear ribonucleoprotein A1 | 1 | x | | | x | | SLE vs AID |
| 6 | 3181 | HNRNPA2B1 | heterogeneous nuclear ribonucleoprotein A2/B1 | 1 | x | | | x | | SLE vs AID |
| 7 | 9961 | MVP | major vault protein | 1 | x | x | x | x | | SLE vs AID |
| 8 | 6175 | RPLP0 | ribosomal protein, large, P0 | 1 | x | x | x | | | SLE vs AID |
| 9 | 6176 | RPLP1 | ribosomal protein, large, P1 | 1 | x | x | x | | x | SLE vs AID |
| 10 | 6181 | RPLP2 | ribosomal protein, large, P2 | 1 | x | x | x | | | SLE vs AID |
| 11 | 30011 | SH3KBP1 | SH3-domain kinase binding protein 1 | 1 | x | | | x | | SLE vs AID |
| 12 | 6625 | SNRNP70 | small nuclear ribonucleoprotein 70 kDa (U1) | 1 | x | | | | | SLE vs AID |
| 13 | 6628 | SNRPB | small nuclear ribonucleoprotein polypeptides B and B1 | 1 | x | x | x | | | SLE vs AID |
| 14 | 6638 | SNRPN | small nuclear ribonucleoprotein polypeptide N | 1 | x | | | | | SLE vs AID |
| 15 | 6672 | SP100 | SP100 nuclear antigen | 1 | x | | | x | | SLE vs AID |
| 16 | 6710 | SPTB | spectrin, beta, erythrocytic | 1 | x | | | x | | SLE vs AID |
| 17 | 6741 | SSB | Sjogren syndrome antigen B (autoantigen La) | 1 | x | x | | | | SLE vs AID |
| 18 | 7112 | TMPO | thymopoietin | 1 | x | | | x | x | SLE vs AID |

TABLE 2-continued

List of all antigen reactivities

| SEQ ID No. | Gene GeneID | Gene Symbol | Gene Name | Group | Panel SLE | Panel L. Nephr. | SLE Cluster | Statistical Test ENA-4 neg vs HV | L. Nephr. vs SLE | SLE vs control |
|---|---|---|---|---|---|---|---|---|---|---|
| 19 | 6737 | TRIM21 | tripartite motif-containing 21 | 1 | x | | x | x | | SLE vs AID |
| 20 | 6738 | TROVE2 | TROVE domain family, member 2 | 1 | x | | x | | | SLE vs RA |
| 21 | 7431 | VIM | vimentin | 1 | x | | | x | | SLE vs AID |
| 22 | 7520 | XRCC5 | X-ray repair complementing defective repair in Chinese hamster cells 5 (double-strand-break rejoining) | 1 | x | | | x | | SLE vs AID |
| 23 | 7764 | ZNF217 | zinc finger protein 217 | 1 | x | | | x | | SLE vs AID |
| 24 | 64763 | ZNF574 | zinc finger protein 574 | 1 | x | | | x | | SLE vs AID |
| 25 | 148741 | ANKRD35 | ankyrin repeat domain 35 | 2 | | x | | | x | SLE vs HV |
| 26 | 84779 | ARD1B | ARD1 homolog B (*S. cerevisiae*) | 2 | | x | | | x | SLE vs AID |
| 27 | 672 | BRCA1 | breast cancer 1, early onset | 2 | | x | | | x | SLE vs HV |
| 28 | 134359 | C5orf37 | chromosome 5 open reading frame 37 | 2 | | x | | x | x | SLE vs HV |
| 29 | 9478 | CABP1 | calcium binding protein 1 | 2 | | x | | | x | SLE vs HV |
| 30 | 90557 | CCDC74A | coiled-coil domain containing 74A | 2 | | x | | | x | SLE vs HV |
| 31 | 9973 | CCS | copper chaperone for superoxide dismutase | 2 | | x | x | x | x | SLE vs AID |
| 32 | 1410 | CRYAB | crystallin, alpha B | 2 | | x | | | x | SLE vs HV |
| 33 | 55802 | DCP1A | DCP1 decapping enzyme homolog A (*S. cerevisiae*) | 2 | | x | | | x | SLE vs HV |
| 34 | 79147 | FKRP | fukutin related protein | 2 | | x | | | x | SLE vs HV |
| 35 | 26128 | KIAA1279 | KIAA1279 | 2 | | x | | | x | SLE vs HV |
| 36 | 57608 | KIAA1462 | KIAA1462 | 2 | | x | | | x | SLE vs HV |
| 37 | 1939 | LGTN | ligatin | 2 | | x | | | x | SLE vs HV |
| 38 | 84298 | LLPH | LLP homolog, long-term synaptic facilitation (*Aplysia*) | 2 | | x | | | x | SLE vs HV |
| 39 | 11253 | MAN1B1 | mannosidase, alpha, class 1B, member 1 | 2 | | x | | | x | SLE vs HV |
| 40 | 84930 | MASTL | microtubule associated serine/threonine kinase-like | 2 | | x | | | x | SLE vs HV |
| 41 | 54531 | MIER2 | mesorm induction early response 1, family member 2 | 2 | | x | x | x | x | SLE vs RA |
| 42 | 4594 | MUT | methylmalonyl Coenzyme A mutase | 2 | | x | | | x | SLE vs HV |
| 43 | 399687 | MYO18A | myosin XVIIIA | 2 | | x | | | x | SLE vs HV |
| 44 | 8883 | NAE1 | NEDD8 activating enzyme E1 subunit 1 | 2 | | x | | | x | SLE vs HV |
| 45 | 10458 | BAIAP2 | BAI1-associated protein 2 | 2 | | x | | | x | SLE vs HV |
| 46 | 4869 | NPM1 | nucleophosmin (nucleolar phosphoprotein B23, numatrin) | 2 | | x | | | x | SLE vs HV |
| 47 | 5223 | PGAM1 | phosphoglycerate mutase 1 (brain) | 2 | | x | | | x | SLE vs HV |

TABLE 2-continued

List of all antigen reactivities

| SEQ ID No. | Gene GeneID | Gene Symbol | Gene Name | Group | Panel SLE | Panel L. Nephr. | SLE Cluster | Statistical Test ENA-4 neg vs HV | L. Nephr. vs SLE | SLE vs control |
|---|---|---|---|---|---|---|---|---|---|---|
| 48 | 11040 | PIM2 | pim-2 oncogene | 2 | x | | | | x | SLE vs HV |
| 49 | 54517 | PUS7 | pseudouridylate synthase 7 homolog (S. cerevisiae) | 2 | x | | | | x | SLE vs HV |
| 50 | 6605 | SMARCE1 | SWI/SNF related, matrix associated, actin dependent regulator of chromatin, subfamily e, member 1 | 2 | x | | | | x | SLE vs AID |
| 51 | 23635 | SSBP2 | single-stranded DNA binding protein 2 | 2 | x | | | x | x | SLE vs HV |
| 52 | 83660 | TLN2 | talin 2 | 2 | x | | | | x | SLE vs HV |
| 53 | 51673 | TPPP3 | tubulin polymerization-promoting protein family member 3 | 2 | x | | | | x | SLE vs HV |
| 54 | 7265 | TTC1 | tetratricopeptide repeat domain 1 | 2 | x | | | | x | SLE vs HV |
| 55 | 124930 | ANKRD13B | ankyrin repeat domain 13B | 3 | | | x | | | SLE vs HV |
| 56 | 160 | AP2A1 | adaptor-related protein complex 2, alpha 1 subunit | 3 | | | x | | | SLE vs HV |
| 57 | 53335 | BCL11A | B-cell CLL/lymphoma 11A (zinc finger protein) | 3 | | | x | x | | |
| 58 | 79959 | CEP76 | centrosomal protein 76 kDa | 3 | | | | | x | |
| 59 | 1153 | CIRBP | cold inducible RNA binding protein | 3 | | | x | | | SLE vs HV |
| 60 | 51084 | CRYL1 | crystallin, lambda 1 | 3 | | | | | x | |
| 61 | 55827 | DCAF6 | DDB1 and CUL4 associated factor 6 | 3 | | | x | x | x | SLE vs AID |
| 62 | 6993 | DYNLT1 | dynein, light chain, Tctex-type 1 | 3 | | | x | | | SLE vs HV |
| 63 | 283991 | FAM100B | family with sequence similarity 100, member B | 3 | | | x | | | SLE vs HV |
| 64 | 9815 | GIT2 | G protein-coupled receptor kinase interacting ArfGAP 2 | 3 | | | x | | | SLE vs HV |
| 65 | 84706 | GPT2 | glutamic pyruvate transaminase (alanine aminotransferase) 2 | 3 | | | | | x | |
| 66 | 3059 | HCLS1 | hematopoietic cell-specific Lyn substrate 1 | 3 | | | x | x | | SLE vs AID |
| 67 | 3329 | HSPD1 | heat shock 60 kDa protein 1 (chaperonin) | 3 | | | | | x | |
| 68 | 3490 | IGFBP7 | insulin-like growth factor binding protein 7 | 3 | | | x | | | SLE vs HV |
| 69 | 23392 | KIAA0368 | KIAA0368 | 3 | | | | | x | |
| 70 | 84695 | LOXL3 | lysyl oxidase-like 3 | 3 | | | | | x | |
| 71 | 4133 | MAP2 | microtubule-associated protein 2 | 3 | | | | | x | SLE vs RA |
| 72 | 6837 | MED22 | mediator complex subunit 22 | 3 | | | | | x | |
| 73 | 29079 | MED4 | mediator complex subunit 4 | 3 | | | x | x | | |
| 74 | 10933 | MORF4L1 | mortality factor 4 like 1 | 3 | | | | | x | |

TABLE 2-continued

List of all antigen reactivities

| SEQ ID No. | GeneID | Gene Symbol | Gene Name | Group | Panel SLE | Panel L. Nephr. | SLE Cluster | Statistical Test ENA-4 neg vs HV | Statistical Test L. Nephr. vs SLE | SLE vs control |
|---|---|---|---|---|---|---|---|---|---|---|
| 75 | 64963 | MRPS11 | mitochondrial ribosomal protein S11 | 3 | | | x | x | | SLE vs HV |
| 76 | 81565 | NDEL1 | nudE nuclear distribution gene E homolog (*A. nidulans*)-like 1 | 3 | | | | | x | |
| 77 | 57447 | NDRG2 | NDRG family member 2 | 3 | | | x | | | SLE vs HV |
| 78 | 4744 | NEFH | neurofilament, heavy polypeptide | 3 | | | | | x | |
| 79 | 153478 | PLEKHG4B | pleckstrin homology domain containing, family G (with RhoGef domain) member 4B [*homo sapiens* (human)] | 3 | | | x | | | SLE vs RA |
| 80 | 11054 | OGFR | opioid growth factor receptor | 3 | | | x | x | | SLE vs AID |
| 81 | 56122 | PCDHB14 | protocadherin beta 14 | 3 | | | x | | | SLE vs HV |
| 82 | 2923 | PDIA3 | protein disulfide isomerase family A, member 3 | 3 | | | x | | | SLE vs HV |
| 83 | 23646 | PLD3 | phospholipase D family, member 3 | 3 | | | x | | | SLE vs HV |
| 84 | 23759 | PPIL2 | peptidylprolyl isomerase (cyclophilin)-like 2 | 3 | | | | | x | |
| 85 | 5557 | PRIM1 | primase, DNA, polypeptide 1 (49 kDa) | 3 | | | | x | x | |
| 86 | 5682 | PSMA1 | proteasome (prosome, macropain) subunit, alpha type, 1 | 3 | | | x | | | SLE vs HV |
| 87 | 5802 | PTPRS | protein tyrosine phosphatase, receptor type, S | 3 | | | x | | | SLE vs HV |
| 88 | 81890 | QTRT1 | queuine tRNA-ribosyltransferase 1 | 3 | | | x | | | SLE vs HV |
| 89 | 116362 | RBP7 | retinol binding protein 7, cellular | 3 | | | x | | | SLE vs HV |
| 90 | 10287 | RGS19 | regulator of G-protein signaling 19 | 3 | | | x | x | | |
| 91 | 83642 | RP3-402G11.5 | selenoprotein O | 3 | | | x | | | SLE vs HV |
| 92 | 6389 | SDHA | succinate dehydrogenase complex, subunit A, flavoprotein (Fp) | 3 | | | x | x | | SLE vs AID |
| 93 | 54437 | SEMA5B | sema domain, seven thrombospondin repeats (type 1 and type 1-like), transmembrane domain (TM) and short cytoplasmic domain, (semaphorin) 5B | 3 | | | | | x | |
| 94 | 59343 | SENP2 | SUMO1/sentrin/SMT3 specific peptidase 2 | 3 | | | x | | | SLE vs HV |
| 95 | 6629 | SNRPB2 | small nuclear ribonucleoprotein polypeptide B" | 3 | | | x | | | SLE vs AID |
| 96 | 27131 | SNX5 | sorting nexin 5 | 3 | | | x | | | SLE vs HV |

TABLE 2-continued

List of all antigen reactivities

| SEQ ID No. | Gene GeneID | Gene Symbol | Gene Name | Group | Panel SLE | L. Nephr. | SLE Cluster | Statistical Test ENA-4 neg vs HV | L. Nephr. vs SLE | SLE vs control |
|---|---|---|---|---|---|---|---|---|---|---|
| 97 | 9021 | SOCS3 | suppressor of cytokine signaling 3 | 3 | | | | x | x | SLE vs HV |
| 98 | 3925 | STMN1 | stathmin 1 | 3 | | | x | | | SLE vs HV |
| 99 | 81551 | STMN4 | stathmin-like 4 | 3 | | | x | | | SLE vs HV |
| 100 | 27097 | TAF5L | TAF5-like RNA polymerase II, p300/CBP-associated factor (PCAF)-associated factor, 65 kDa | 3 | | | x | | | SLE vs HV |
| 101 | 79921 | TCEAL4 | transcription elongation factor A (SII)-like 4 | 3 | | | x | | | SLE vs HV |
| 102 | 10040 | TOM1L1 | target of myb1 (chicken)-like 1 | 3 | | | x | | | SLE vs HV |
| 103 | 22974 | TPX2 | TPX2, microtubule-associated, homolog (*Xenopus laevis*) | 3 | | | x | | | SLE vs HV |
| 104 | 51567 | TTRAP | TRAF and TNF receptor associated protein | 3 | | | | | x | |
| 105 | 8615 | USO1 | USO1 homolog, vesicle docking protein (yeast) | 3 | | | | x | x | |
| 106 | 10869 | USP19 | ubiquitin specific peptidase 19 | 3 | | | x | | | SLE vs RA |
| 107 | 29761 | USP25 | ubiquitin specific peptidase 25 | 3 | | | | | x | |
| 108 | 375690 | WASH5P | WAS protein family homolog 5 pseudogene | 3 | | | x | x | | SLE vs HV |
| 109 | 10413 | YAP1 | Yes-associated protein 1, 65 kDa | 3 | | | | | x | |
| 110 | 653121 | ZBTB8A | zinc finger and BTB domain containing 8A | 3 | | | x | x | | SLE vs HV |
| 111 | 55311 | ZNF444 | zinc finger protein 444 | 3 | | | | | x | |
| 112 | 29 | ABR | active BCR-related gene | 4 | | | | x | | SLE vs AID |
| 113 | 118 | ADD1 | adducin 1 (alpha) | 4 | | | | x | | SLE vs AID |
| 114 | 55256 | ADI1 | acireductone dioxygenase 1 | 4 | | | | x | | SLE vs HV |
| 115 | 9255 | AIMP1 | aminoacyl tRNA synthetase complex-interacting multifunctional protein 1 | 4 | | | | x | | |
| 116 | 54522 | ANKRD16 | ankyrin repeat domain 16 | 4 | | | | x | | SLE vs HV |
| 117 | 348 | APOE | apolipoprotein E | 4 | | | | x | | SLE vs HV |
| 118 | 64333 | ARHGAP9 | Rho GTPase activating protein 9 | 4 | | | | x | | SLE vs HV |
| 119 | 22994 | AZI1 | 5-azacytidine induced 1 | 4 | | | | x | | SLE vs HV |
| 120 | 55971 | BAIAP2L1 | BAI1-associated protein 2-like 1 | 4 | | | | x | | |
| 121 | 7919 | BAT1 | HLA-B associated transcript 1 | 4 | | | | x | | SLE vs RA |
| 122 | 6046 | BRD2 | bromodomain containing 2 | 4 | | | | x | | |
| 123 | 56912 | C11orf60 | chromosome 11 open reading frame 60 | 4 | | | | x | | |
| 124 | 79415 | C17orf62 | chromosome 17 open reading frame 62 | 4 | | | | x | | |

TABLE 2-continued

List of all antigen reactivities

| SEQ ID No. | Gene GeneID | Gene Symbol | Gene Name | Group | Panel SLE | Panel L. Nephr. | SLE Cluster | Statistical Test ENA-4 neg vs HV | L. Nephr. vs SLE | SLE vs control |
|---|---|---|---|---|---|---|---|---|---|---|
| 125 | 51300 | C3orf1 | chromosome 3 open reading frame 1 | 4 | | | | x | | SLE vs RA |
| 126 | 128866 | CHMP4B | chromatin modifying protein 4B | 4 | | | | x | | SLE vs AID |
| 127 | 23152 | CIC | capicua homolog (*Drosophila*) | 4 | | | | x | | SLE vs AID |
| 128 | 10970 | CKAP4 | cytoskeleton-associated protein 4 | 4 | | | | x | | SLE vs HV |
| 129 | 23122 | CLASP2 | cytoplasmic linker associated protein 2 | 4 | | | | x | | SLE vs HV |
| 130 | 1311 | COMP | cartilage oligomeric matrix protein | 4 | | | | x | | |
| 131 | 7812 | CSDE1 | cold shock domain containing E1, RNA-binding | 4 | | | | x | | SLE vs HV |
| 132 | 8642 | DCHS1 | dachsous 1 (*Drosophila*) | 4 | | | | x | | SLE vs AID |
| 133 | 9909 | DENND4B | DENN/MADD domain containing 4B | 4 | | | | x | x | |
| 134 | 1743 | DLST | dihydrolipoamide S-succinyltransferase (E2 component of 2-oxo-glutarate complex) | 4 | | | | x | | |
| 135 | 84444 | DOT1L | DOT1-like, histone H3 methyltransferase (*S. cerevisiae*) | 4 | | | | x | | |
| 136 | 51143 | DYNC1LI1 | dynein, cytoplasmic 1, light intermediate chain 1 | 4 | | | | x | | SLE vs HV |
| 137 | 51011 | FAHD2A | fumarylacetoacetate hydrolase domain containing 2A | 4 | | | | x | | |
| 138 | 92689 | FAM114A1 | family with sequence similarity 114, member A1 | 4 | | | | x | | |
| 139 | 54463 | FAM134B | family with sequence similarity 134, member B | 4 | | | | x | | |
| 140 | 100129583 | FAM47E | family with sequence similarity 47, member E | 4 | | | | x | | SLE vs HV |
| 141 | 93611 | FBXO44 | F-box protein 44 | 4 | | | | x | | |
| 142 | 60681 | FKBP10 | FK506 binding protein 10, 65 kDa | 4 | | | | x | | SLE vs AID |
| 143 | 23360 | FNBP4 | formin binding protein 4 | 4 | | | | x | | SLE vs HV |
| 144 | 2300 | FOXL1 | forkhead box L1 | 4 | | | | x | | SLE vs HV |
| 145 | 64689 | GORASP1 | golgi reassembly stacking protein 1, 65 kDa | 4 | | | | x | | SLE vs AID |
| 146 | 2934 | GSN | gelsolin (amyloidosis, Finnish type) | 4 | | | | x | | SLE vs HV |
| 147 | 3039 | HBA1 | hemoglobin, alpha 1 | 4 | | | | x | | |
| 148 | 3040 | HBA2 | hemoglobin, alpha 2 | 4 | | | | x | | |
| 149 | 388585 | HES5 | hairy and enhancer of split 5 (*Drosophila*) | 4 | | | | x | | |
| 150 | 10525 | HYOU1 | hypoxia up-regulated 1 | 4 | | | | x | | |
| 151 | 3608 | ILF2 | interleukin enhancer binding factor 2, 45 kDa | 4 | | | | x | | SLE vs RA |
| 152 | 23135 | KDM6B | lysine (K)-specific demethylase 6B | 4 | | | | x | | SLE vs AID |

TABLE 2-continued

List of all antigen reactivities

| SEQ ID No. | Gene GeneID | Gene Symbol | Gene Name | Group | Panel SLE | Panel L. Nephr. | SLE Cluster | Statistical Test ENA-4 neg vs HV | L. Nephr. vs SLE | SLE vs control |
|---|---|---|---|---|---|---|---|---|---|---|
| 153 | 56243 | KIAA1217 | KIAA1217 | 4 | | | | x | | SLE vs HV |
| 154 | 57662 | KIAA1543 | KIAA1543 | 4 | | | | x | | |
| 155 | 57498 | KIDINS220 | kinase D-interacting substrate, 220 kDa | 4 | | | | x | | |
| 156 | 3855 | KRT7 | keratin 7 | 4 | | | | x | | SLE vs HV |
| 157 | 729970 | LOC729970 | similar to hCG2028352 | 4 | | | | x | | |
| 158 | 9935 | MAFB | v-maf musculoaponeurotic fibrosarcoma oncogene homolog B (avian) | 4 | | | | x | | |
| 159 | 23764 | MAFF | v-maf musculoaponeurotic fibrosarcoma oncogene homolog F (avian) | 4 | | | | x | | SLE vs HV |
| 160 | 22924 | MAPRE3 | microtubule-associated protein, RP/EB family, member 3 | 4 | | | | x | | |
| 161 | 8079 | MLF2 | myeloid leukemia factor 2 | 4 | | | | x | | |
| 162 | 4676 | NAP1L4 | nucleosome assembly protein 1-like 4 | 4 | | | | x | | |
| 163 | 4688 | NCF2 | neutrophil cytosolic factor 2 | 4 | | | | x | | SLE vs HV |
| 164 | 4780 | NFE2L2 | nuclear factor (erythroid-derived 2)-like 2 | 4 | | | | x | | |
| 165 | 79840 | NHEJ1 | nonhomologous end-joining factor 1 | 4 | | | | x | x | |
| 166 | 22861 | NLRP1 | NLR family, pyrin domain containing 1 | 4 | | | | x | | SLE vs HV |
| 167 | 65009 | NDRG4 | NDRG family member 4 | 4 | | | | x | | SLE vs HV |
| 168 | 4841 | NONO | non-POU domain containing, octamer-binding | 4 | | | | x | | SLE vs AID |
| 169 | 29982 | NRBF2 | nuclear receptor binding factor 2 | 4 | | | | x | | SLE vs AID |
| 170 | 8439 | NSMAF | neutral sphingomyelinase (N-SMase) activation associated factor | 4 | | | | x | | SLE vs HV |
| 171 | 4926 | NUMA1 | nuclear mitotic apparatus protein 1 | 4 | | | | x | | SLE vs RA |
| 172 | 84759 | PCGF1 | polycomb group ring finger 1 | 4 | | | | x | | |
| 173 | 84306 | PDCD2L | programmed cell death 2-like | 4 | | | | x | | SLE vs HV |
| 174 | 5195 | PEX14 | peroxisomal biogenesis factor 14 | 4 | | | | x | | SLE vs HV |
| 175 | 9091 | PIGQ | phosphatidylinositol glycan anchor biosynthesis, class Q | 4 | | | | x | | SLE vs RA |
| 176 | 100137049 | PLA2G4B | phospholipase A2, group IVB (cytosolic) | 4 | | | | x | | SLE vs RA |
| 177 | 10226 | PLIN3 | perilipin 3 | 4 | | | | x | | |
| 178 | 5373 | PMM2 | phosphomannomutase 2 | 4 | | | | x | | |
| 179 | 10450 | PPIE | peptidylprolyl isomerase E (cyclophilin E) | 4 | | | | x | | |

TABLE 2-continued

List of all antigen reactivities

| SEQ ID No. | Gene GeneID | Gene Symbol | Gene Name | Group | Panel SLE | L. Nephr. | SLE Cluster | Statistical Test ENA-4 neg vs HV | L. Nephr. vs SLE | SLE vs control |
|---|---|---|---|---|---|---|---|---|---|---|
| 180 | 5694 | PSMB6 | proteasome (prosome, macropain) subunit, beta type, 6 | 4 | | | | x | | |
| 181 | 22913 | RALY | RNA binding protein, autoantigenic (hnRNP-associated with lethal yellow homolog (mouse)) | 4 | | | | x | | SLE vs HV |
| 182 | 8241 | RBM10 | RNA binding motif protein 10 | 4 | | | | x | | |
| 183 | 9904 | RBM19 | RNA binding motif protein 19 | 4 | | | | x | | SLE vs HV |
| 184 | 9743 | RICS | Rho GTPase-activating protein | 4 | | | | x | | |
| 185 | 8780 | RIOK3 | RIO kinase 3 (yeast) | 4 | | | | x | | |
| 186 | 8578 | SCARF1 | scavenger receptor class F, member 1 | 4 | | | | x | | SLE vs AID |
| 187 | 23513 | SCRIB | scribbled homolog (*Drosophila*) | 4 | | | | x | | SLE vs HV |
| 188 | 644096 | SDHAF1 | succinate dehydrogenase complex assembly factor 1 | 4 | | | | x | | SLE vs RA |
| | 57794 | SF4 | splicing factor 4 | 4 | | | | x | | SLE vs RA |
| 189 | 9814 | SFI1 | Sfi1 homolog, spindle assembly associated (yeast) | 4 | | | | x | | |
| 190 | 6421 | SFPQ | splicing factor proline/glutamine-rich (polypyrimidine tract binding protein associated) | 4 | | | | x | | SLE vs AID |
| 191 | 83442 | SH3BGRL3 | SH3 domain binding glutamic acid-rich protein like 3 | 4 | | | | x | | |
| 192 | 6461 | SHB | Src homology 2 domain containing adaptor protein B | 4 | | | | x | | SLE vs AID |
| 193 | 23381 | SMG5 | Smg-5 homolog, nonsense mediated mRNA decay factor (*C. elegans*) | 4 | | | | x | | SLE vs HV |
| 194 | 112574 | SNX18 | sorting nexin 18 | 4 | | | | x | | SLE vs HV |
| 195 | 84501 | SPIRE2 | spire homolog 2 (*Drosophila*) | 4 | | | | x | | SLE vs HV |
| 196 | 54961 | SSH3 | slingshot homolog 3 (*Drosophila*) | 4 | | | | x | | SLE vs AID |
| 197 | 9263 | STK17A | serine/threonine kinase 17a | 4 | | | | x | | |
| 198 | 51111 | SUV420H1 | suppressor of variegation 4-20 homolog 1 (*Drosophila*) | 4 | | | | x | | |
| 199 | 6902 | TBCA | tubulin folding cofactor A | 4 | | | | x | | |
| 200 | 7024 | TFCP2 | transcription factor CP2 | 4 | | | | x | | SLE vs HV |
| 201 | 7030 | TFE3 | transcription factor binding to IGHM enhancer 3 | 4 | | | | x | | SLE vs HV |
| 202 | 90326 | THAP3 | THAP domain containing, apoptosis associated protein 3 | 4 | | | | x | | SLE vs AID |

TABLE 2-continued

List of all antigen reactivities

| SEQ ID No. | Gene GeneID | Gene Symbol | Gene Name | Group | Panel SLE | Panel L. Nephr. | SLE Cluster | Statistical Test ENA-4 neg vs HV | L. Nephr. vs SLE | SLE vs control |
|---|---|---|---|---|---|---|---|---|---|---|
| 203 | 10043 | TOM1 | target of myb1 (chicken) | 4 | | | | x | | |
| 204 | 7168 | TPM1 | tropomyosin 1 (alpha) | 4 | | | | x | | SLE vs HV |
| 205 | 54952 | TRNAU1AP | tRNA selenocysteine 1 associated protein 1 | 4 | | | | x | | |
| 206 | 26140 | TTLL3 | tubulin tyrosine ligase-like family, member 3 | 4 | | | | x | | |
| 207 | 7371 | UCK2 | uridine-cytidine kinase 2 | 4 | | | | x | | SLE vs HV |
| 208 | 9277 | WDR46 | WD repeat domain 46 | 4 | | | | x | | SLE vs HV |
| 209 | 55100 | WDR70 | WD repeat domain 70 | 4 | | | | x | | SLE vs AID |
| 210 | 23038 | WDTC1 | WD and tetratricopeptide repeats 1 | 4 | | | | x | | SLE vs HV |
| 211 | 9831 | ZNF623 | zinc finger protein 623 | 4 | | | | x | | |
| 212 | 79364 | ZXDC | ZXD family zinc finger C | 4 | | | | x | x | SLE vs AID |
| 213 | 7791 | ZYX | zyxin | 4 | | | | x | | SLE vs AID |
| 214 | 55964 | SEPT3 | septin 3 | 5 | | | | | x | |
| 215 | 5413 | SEPT5 | septin 5 | 5 | | | | | x | |
| 216 | 26574 | AATF | apoptosis antagonizing transcription factor | 5 | | | | | x | |
| 217 | 91703 | ACY3 | aspartoacylase (aminocyclase) 3 | 5 | | | | | x | |
| 218 | 9509 | ADAMTS2 | ADAM metallopeptidase with thrombospondin type 1 motif, 2 | 6 | | | | | | SLE vs RA |
| 219 | 10939 | AFG3L2 | AFG3 ATPase family gene 3-like 2 (yeast) | 6 | | | | | | SLE vs HV |
| 220 | 1646 | AKR1C2 | aldo-keto reductase family 1, member C2 (dihydrodiol dehydrogenase 2; bile acid binding protein; 3-alpha hydroxysteroid dehydrogenase, type III) | 6 | | | | | | SLE vs RA |
| 221 | 267 | AMFR | autocrine motility factor receptor | 6 | | | | | | SLE vs RA |
| 222 | 10777 | ARPP-21 | cyclic AMP-regulated phosphoprotein, 21 kD | 6 | | | | | | SLE vs RA |
| 223 | 421 | ARVCF | armadillo repeat gene deletes in velocardiofacial syndrome | 6 | | | | | | SLE vs RA |
| 224 | 80150 | ASRGL1 | asparaginase like 1 | 6 | | | | | | SLE vs RA |
| 225 | 539 | ATP5O | ATP synthase, H+ transporting, mitochondrial F1 complex, O subunit | 6 | | | | | | SLE vs RA |
| 226 | 79870 | BAALC | brain and acute leukemia, cytoplasmic | 6 | | | | | | SLE vs RA |
| 227 | 9531 | BAG3 | BCL2-associated athanogene 3 | 5 | | | | | x | |
| 228 | 9275 | BCL7B | B-cell CLL/lymphoma 7B | 6 | | | | | | SLE vs HV |

TABLE 2-continued

List of all antigen reactivities

| SEQ ID No. | GeneID | Gene Symbol | Gene Name | Group | Panel SLE | Panel L. Nephr. | SLE Cluster | Statistical Test ENA-4 neg vs HV | L. Nephr. vs SLE | SLE vs control |
|---|---|---|---|---|---|---|---|---|---|---|
| 229 | 55108 | BSDC1 | BSD domain containing 1 | 6 | | | | | | SLE vs AID |
| 230 | 54934 | C12orf41 | chromosome 12 open reading frame 41 | 6 | | | | | | SLE vs RA |
| 231 | 55049 | C19orf60 | chromosome 19 open reading frame 60 | 6 | | | | | | SLE vs RA |
| 232 | 388799 | C20orf107 | chromosome 20 open reading frame 107 | 5 | | | | | x | |
| 233 | 149840 | C20orf196 | chromosome 20 open reading frame 196 | 6 | | | | | | SLE vs RA |
| 234 | 51507 | C20orf43 | chromosome 20 open reading frame 43 | 6 | | | | | | SLE vs RA |
| 235 | 55684 | C9orf86 | chromosome 9 open reading frame 86 | 6 | | | | | | SLE vs HV |
| 236 | 23523 | CABIN1 | calcineurin binding protein 1 | 6 | | | | | | SLE vs RA |
| 237 | 157922 | CAMSAP1 | calmodulin regulated spectrin-associated protein 1 | 6 | | | | | | SLE vs RA |
| 238 | 23624 | CBLC | Cas-Br-M (murine) ecotropic retroviral transforming sequence c | 6 | | | | | | SLE vs HV |
| 239 | 124808 | CCDC43 | coiled-coil domain containing 43 | 6 | | | | | | SLE vs RA |
| 240 | 100133941 | CD24 | CD24 molecule | 5 | | | | | x | |
| 241 | 11140 | CDC37 | cell division cycle 37 homolog (*S. cerevisiae*) | 6 | | | | | | SLE vs RA |
| 242 | 10153 | CEBPZ | CCAAT/enhancer binding protein (C/EBP), zeta | 6 | | | | | | SLE vs RA |
| 243 | 51510 | CHMP5 | chromatin modifying protein 5 | 6 | | | | | | SLE vs RA |
| 244 | 63922 | CHTF18 | CTF18, chromosome transmission fidelity factor 18 homolog (*S. cerevisiae*) | 5 | | | | | x | |
| 245 | 51727 | CMPK1 | cytidine monophosphate (UMP-CMP) kinase 1, cytosolic | 6 | | | | | | SLE vs AID |
| 246 | 64708 | COPS7B | COP9 constitutive photomorphogenic homolog subunit 7B (*Arabidopsis*) | 5 | | | | | x | |
| 247 | 51117 | COQ4 | coenzyme Q4 homolog (*S. cerevisiae*) | 6 | | | | | | SLE vs RA |
| 248 | 27254 | CSDC2 | cold shock domain containing C2, RNA binding | 5 | | | | | x | |
| 249 | 162989 | DEDD2 | death effector domain containing 2 | 6 | | | | | | SLE vs RA |
| 250 | 9704 | DHX34 | DEAH (Asp-Glu-Ala-His) box polypeptide 34 | 6 | | | | | | SLE vs RA |
| 251 | 55837 | EAPP | E2F-associated phosphoprotein | 6 | | | | | | SLE vs RA |
| 252 | 1915 | EEF1A1 | eukaryotic translation elongation factor 1 alpha 1 | 6 | | | | | | SLE vs RA |
| 253 | 1936 | EEF1D | eukaryotic translation elongation factor 1 delta (guanine nucleotide exchange protein) | 6 | | | | | | SLE vs RA |

TABLE 2-continued

List of all antigen reactivities

| SEQ ID No. | Gene GeneID | Gene Symbol | Gene Name | Group | Panel SLE | Panel L. Nephr. | SLE Cluster | Statistical Test ENA-4 neg vs HV | L. Nephr. vs SLE | SLE vs control |
|---|---|---|---|---|---|---|---|---|---|---|
| 254 | 8669 | EIF3J | eukaryotic translation initiation factor 3, subunit J | 6 | | | | | | SLE vs RA |
| 255 | 55740 | ENAH | enabled homolog (*Drosophila*) | 6 | | | | | | SLE vs HV |
| 256 | 2023 | ENO1 | enolase 1, (alpha) | 6 | | | | | | SLE vs HV |
| 257 | 11124 | FAF1 | Fas (TNFRSF6) associated factor 1 | 5 | | | | | x | |
| 258 | 11170 | FAM107A | family with sequence similarity 107, member A | 6 | | | | | | SLE vs HV |
| 259 | 84908 | FAM136A | family with sequence similarity 136, member A | 6 | | | | | | SLE vs RA |
| 260 | 10144 | FAM13A | family with sequence similarity 13, member A | 6 | | | | | | SLE vs RA |
| 261 | 26017 | FAM32A | family with sequence similarity 32, member A | 6 | | | | | | SLE vs HV |
| 262 | 64762 | FAM59A | family with sequence similarity 59, member A | 6 | | | | | | SLE vs RA |
| 263 | 150946 | FAM59B | family with sequence similarity 59, member B | 6 | | | | | | SLE vs HV |
| 264 | 83706 | FERMT3 | fermitin family homolog 3 (*Drosophila*) | 6 | | | | | | SLE vs RA |
| 265 | 23307 | FKBP15 | FK506 binding protein 15, 133 kDa | 6 | | | | | | SLE vs HV |
| 266 | 2670 | GFAP | glial fibrillary acidic protein | 6 | | | | | | SLE vs RA |
| 267 | 51031 | GLOD4 | glyoxalase domain containing 4 | 6 | | | | | | SLE vs AID |
| 268 | 81488 | GRINL1A | glutamate receptor, ionotropic, N-methyl D-aspartate-like 1A | 6 | | | | | | SLE vs RA |
| 269 | 2922 | GRP | gastrin-releasing peptide | 6 | | | | | | SLE vs RA |
| 270 | 2935 | GSPT1 | G1 to S phase transition 1 | 6 | | | | | | SLE vs RA |
| 271 | 93323 | HAUS8 | HAUS augmin-like complex, subunit 8 | 6 | | | | | | SLE vs HV |
| 272 | 3054 | HCFC1 | host cell factor C1 (VP16-accessory protein) | 6 | | | | | | SLE vs AID |
| 273 | 3069 | HDLBP | high density lipoprotein binding protein | 6 | | | | | | SLE vs RA |
| 274 | 3184 | HNRNPD | heterogeneous nuclear ribonucleoprotein D (AU-rich element RNA binding protein 1, 37 kDa) | 6 | | | | | | SLE vs HV |
| 275 | 3320 | HSP90AA1 | heat shock protein 90 kDa alpha (cytosolic), class A member 1 | 6 | | | | | | SLE vs RA |
| 276 | 7184 | HSP90B1 | heat shock protein 90 kDa beta (Grp94), member 1 | 6 | | | | | | SLE vs RA |
| 277 | 3304 | HSPA1B | heat shock 70 kDa protein 1B | 6 | | | | | | SLE vs RA |
| 278 | 3315 | HSPB1 | heat shock 27 kDa protein 1 | 4 | | | | x | x | SLE vs RA |
| 279 | 5654 | HTRA1 | HtrA serine peptidase 1 | 6 | | | | | | SLE vs RA |

TABLE 2-continued

List of all antigen reactivities

| SEQ ID No. | Gene GeneID | Gene Symbol | Gene Name | Group | Panel SLE | Panel L. Nephr. | SLE Cluster | Statistical Test ENA-4 neg vs HV | L. Nephr. vs SLE | SLE vs control |
|---|---|---|---|---|---|---|---|---|---|---|
| 280 | 3382 | ICA1 | islet cell autoantigen 1, 69 kDa | 6 | | | | | | SLE vs RA |
| 281 | 3550 | IK | IK cytokine, down-regulator of HLA II | 6 | | | | | | SLE vs HV |
| 282 | 80895 | ILKAP | integrin-linked kinase-associated serine/threonine phosphatase 2C | 6 | | | | | | SLE vs RA |
| 283 | 84162 | KIAA1109 | KIAA1109 | 6 | | | | | | SLE vs AID |
| 284 | 3856 | KRT8 | keratin 8 | 6 | | | | | | SLE vs RA |
| 285 | 23367 | LARP1 | La ribonucleoprotein domain family, member 1 | 6 | | | | | | SLE vs AID |
| 286 | 4001 | LMNB1 | lamin B1 | 6 | | | | | | SLE vs RA |
| 287 | 79888 | LPCAT1 | lysophosphatidylcho-line acyltransferase 1 | 5 | | | | | x | SLE vs HV |
| 288 | 10916 | MAGED2 | melanoma antigen family D, 2 | 5 | | | | | x | |
| 289 | 55700 | MAP7D1 | MAP7 domain containing 1 | 6 | | | | | | SLE vs RA |
| 290 | 5602 | MAPK10 | mitogen-activated protein kinase 10 | 6 | | | | | | SLE vs HV |
| 291 | 22919 | MAPRE1 | microtubule-associated protein, RP/EB family, member 1 | 6 | | | | | | SLE vs AID |
| 292 | 4137 | MAPT | microtubule-associated protein tau | 6 | | | | | | SLE vs RA |
| 293 | 23139 | MAST2 | microtubule associated serine/threonine kinase 2 | 6 | | | | | | SLE vs RA |
| 294 | 53615 | MBD3 | methyl-CpG binding domain protein 3 | 6 | | | | | | SLE vs RA |
| 295 | 56922 | MCCC1 | methylcrotonoyl-Coenzyme A carboxylase 1 (alpha) | 6 | | | | | | SLE vs HV |
| 296 | 1953 | MEGF6 | multiple EGF-like-domains 6 | 6 | | | | | | SLE vs RA |
| 297 | 4302 | MLLT6 | myeloid/lymphoid or mixed-lineage leukemia (trithorax homolog, Drosophila); translocated to, 6 | 6 | | | | | | SLE vs RA |
| 298 | 10200 | MPHOSPH6 | M-phase phosphoprotein 6 | 6 | | | | | | SLE vs RA |
| 299 | 10240 | MRPS31 | mitochondrial ribosomal protein S31 | 6 | | | | | | SLE vs HV |
| 300 | 84939 | MUM1 | melanoma associated antigen (mutated) 1 | 5 | | | | | x | |
| 301 | 4599 | MX1 | myxovirus (influenza virus) resistance 1, interferon-inducible protein p78 (mouse) | 6 | | | | | | SLE vs RA |
| 302 | 4716 | NDUFB10 | NADH dehydrogenase (ubiquinone) 1 beta subcomplex, 10, 22 kDa | 6 | | | | | | SLE vs RA |

TABLE 2-continued

List of all antigen reactivities

| SEQ ID No. | Gene GeneID | Gene Symbol | Gene Name | Group | Panel SLE | Panel L. Nephr. | SLE Cluster | Statistical Test ENA-4 neg vs HV | L. Nephr. vs SLE | SLE vs control |
|---|---|---|---|---|---|---|---|---|---|---|
| 303 | 4796 | NFKBIL2 | nuclear factor of kappa light polypeptide gene enhancer in B-cells inhibitor-like 2 | 6 | | | | | | SLE vs HV |
| 304 | 11188 | NISCH | nischarin | 6 | | | | | | SLE vs RA |
| 305 | 10381 | TUBB3 | tubulin, beta 3 class III | 6 | | | | | | SLE vs RA |
| 306 | 8602 | NOP14 | NOP14 nucleolar protein homolog (yeast) | 6 | | | | | | SLE vs RA |
| 307 | 9722 | NOS1AP | nitric oxide synthase 1 (neuronal) adaptor protein | 6 | | | | | | SLE vs RA |
| 308 | 29959 | NRBP1 | nuclear receptor binding protein 1 | 5 | | | | | x | |
| 309 | 142 | PARP1 | poly (ADP-ribose) polymerase 1 | 6 | | | | | | SLE vs RA |
| 310 | 5091 | PC | pyruvate carboxylase | 6 | | | | | | SLE vs RA |
| 311 | 23024 | PDZRN3 | PDZ domain containing ring finger 3 | 6 | | | | | | SLE vs RA |
| 312 | 8682 | PEA15 | phosphoprotein enriched in astrocytes 15 | 6 | | | | | | SLE vs RA |
| 313 | 5187 | PER1 | period homolog 1 (*Drosophila*) | 6 | | | | | | SLE vs HV |
| 314 | 57649 | PHF12 | PHD finger protein 12 | 5 | | | | | x | |
| 315 | 26227 | PHGDH | phosphoglycerate dehydrogenase | 5 | | | | | x | |
| 316 | 1263 | PLK3 | polo-like kinase 3 (*Drosophila*) | 6 | | | | | | SLE vs RA |
| 317 | 23654 | PLXNB2 | plexin B2 | 6 | | | | | | SLE vs RA |
| 318 | 56902 | PNO1 | partner of NOB1 homolog (*S. cerevisiae*) | 6 | | | | | | SLE vs RA |
| 319 | 5479 | PPIB | peptidylprolyl isomerase B (cyclophilin B) | 6 | | | | | | SLE vs HV |
| 320 | 56978 | PRDM8 | PR domain containing 8 | 6 | | | | | | SLE vs HV |
| 321 | 55119 | PRPF38B | PRP38 pre-mRNA processing factor 38 (yeast) domain containing B | 6 | | | | | | SLE vs RA |
| 322 | 5764 | PTN | pleiotrophin | 6 | | | | | | SLE vs HV |
| 323 | 5819 | PVRL2 | poliovirus receptor-related 2 (herpesvirus entry mediator B) | 5 | | | | | x | |
| 324 | 5831 | PYCR1 | pyrroline-5-carboxylate reductase 1 | 6 | | | | | | SLE vs RA |
| 325 | 65997 | RASL11B | RAS-like, family 11, member B | 6 | | | | | | SLE vs RA |
| 326 | 55658 | RNF126 | ring finger protein 126 | 6 | | | | | | SLE vs AID |
| 327 | 115992 | RNF166 | ring finger protein 166 | 6 | | | | | | SLE vs HV |
| 328 | 9025 | RNF8 | ring finger protein 8 | 6 | | | | | | SLE vs HV |
| 329 | 6092 | ROBO2 | roundabout, axon guidance receptor, homolog 2 (*Drosophila*) | 5 | | | | | x | |

TABLE 2-continued

List of all antigen reactivities

| SEQ ID No. | Gene GeneID | Gene Symbol | Gene Name | Group | Panel SLE | Panel L. Nephr. | SLE Cluster | Statistical Test ENA-4 neg vs HV | L. Nephr. vs SLE | SLE vs control |
|---|---|---|---|---|---|---|---|---|---|---|
| 330 | 64221 | ROBO3 | roundabout, axon guidance receptor, homolog 3 (*Drosophila*) | 5 | | | | | x | |
| 331 | 4736 | RPL10A | ribosomal protein L10a | 6 | | | | | | SLE vs RA |
| 332 | 6152 | RPL24 | ribosomal protein L24 | 6 | | | | | | SLE vs RA |
| 333 | 148418 | SAMD13 | sterile alpha motif domain containing 13 | 6 | | | | | | SLE vs HV |
| 334 | 57147 | SCYL3 | SCY1-like 3 (*S. cerevisiae*) | 6 | | | | | | SLE vs AID |
| 335 | 6382 | SDC1 | syndecan 1 | 6 | | | | | | SLE vs RA |
| 336 | 91461 | SGK493 | protein kinase-like protein SgK493 | 5 | | | | | x | |
| 337 | 6449 | SGTA | small glutamine-rich tetratricopeptide repeat (TPR)-containing, alpha | 6 | | | | | | SLE vs HV |
| 338 | 9627 | SNCAIP | synuclein, alpha interacting protein | 5 | | | | | x | |
| 339 | 9552 | SPAG7 | sperm associated antigen 7 | 6 | | | | | | SLE vs RA |
| 340 | 57522 | SRGAP1 | SLIT-ROBO Rho GTPase activating protein 1 | 6 | | | | | | SLE vs RA |
| 341 | 6744 | SSFA2 | sperm specific antigen 2 | 6 | | | | | | SLE vs RA |
| 342 | 6487 | ST3GAL3 | ST3 beta-galactoside alpha-2,3-sialyltransferase 3 | 6 | | | | | | SLE vs RA |
| 343 | 23345 | SYNE1 | spectrin repeat containing, nuclear envelope 1 | 6 | | | | | | SLE vs AID |
| 344 | 6879 | TAF7 | TAF7 RNA polymerase II, TATA box binding protein (TBP)-associated factor, 55 kDa | 6 | | | | | | SLE vs HV |
| 345 | 6895 | TARBP2 | TAR (HIV-1) RNA binding protein 2 | 6 | | | | | | SLE vs RA |
| 346 | 6949 | TCOF1 | Treacher Collins-Franceschetti syndrome 1 | 6 | | | | | | SLE vs RA |
| 347 | 7980 | TFPI2 | tissue factor pathway inhibitor 2 | 5 | | | | | x | |
| 348 | 56674 | TMEM9B | TMEM9 domain family, member B | 6 | | | | | | SLE vs RA |
| 349 | 11189 | TNRC4 | trinucleotide repeat containing 4 | 5 | | | | | x | |
| 350 | 10155 | TRIM28 | tripartite motif-containing 28 | 6 | | | | | | SLE vs HV |
| 351 | 7204 | TRIO | triple functional domain (PTPRF interacting) | 6 | | | | | | SLE vs RA |
| 352 | 203068 | TUBB | tubulin, beta | 6 | | | | | | SLE vs RA |
| 353 | 7280 | TUBB2A | tubulin, beta 2A | 6 | | | | | | SLE vs RA |
| 354 | 27229 | TUBGCP4 | tubulin, gamma complex associated protein 4 | 6 | | | | | | SLE vs RA |
| 355 | 10422 | UBAC1 | UBA domain containing 1 | 6 | | | | | | SLE vs RA |
| 356 | 7316 | UBC | ubiquitin C | 6 | | | | | | SLE vs RA |

TABLE 2-continued

List of all antigen reactivities

| SEQ ID No. | Gene GeneID | Gene Symbol | Gene Name | Group | Panel SLE | Panel L. Nephr. | SLE Cluster | Statistical Test ENA-4 neg vs HV | L. Nephr. vs SLE | SLE vs control |
|---|---|---|---|---|---|---|---|---|---|---|
| 357 | 55585 | UBE2Q1 | ubiquitin-conjugating enzyme E2Q family member 1 | 6 | | | | | | SLE vs HV |
| 358 | 65109 | UPF3B | UPF3 regulator of nonsense transcripts homolog B (yeast) | 5 | | | | | x | |
| 359 | 7378 | UPP1 | uridine phosphorylase 1 | 6 | | | | | | SLE vs AID |
| 360 | 64856 | VWA1 | von Willebrand factor A domain containing 1 | 6 | | | | | | SLE vs RA |
| 361 | 55884 | WSB2 | WD repeat and SOCS box-containing 2 | 5 | | | | | x | |
| 362 | 9877 | ZC3H11A | zinc finger CCCH-type containing 11A | 5 | | | | | x | |
| 363 | 55854 | ZC3H15 | zinc finger CCCH-type containing 15 | 6 | | | | | | SLE vs HV |
| 364 | 7592 | ZNF41 | zinc finger protein 41 | 6 | | | | | | SLE vs RA |
| 365 | 170959 | ZNF431 | zinc finger protein 431 | 6 | | | | | | SLE vs RA |
| 366 | 146542 | ZNF688 | zinc finger protein 688 | 6 | | | | | | SLE vs RA |
| 367 | 4670 | HNRNPM | heterogeneous nuclear ribonucleoprotein M | 7 | | | | | | SLE vs HV |
| 368 | 10540 | DCTN2 | dynactin 2 (p50) | 7 | | | | | | SLE vs HV |
| 369 | 10938 | EHD1 | EH-domain containing 1 | 7 | | | | | | SLE vs HV |
| 370 | 38 | ACAT1 | Acetyl-Coenzyme A acetyltransferase 1 (acetoacetyl Coenzyme A thiolase) | 7 | | | | | | SLE vs HV |
| 371 | 684 | BST2 | bone marrow stromal cell antigen 2 | 7 | | | | | | SLE vs HV |
| 372 | 1058 | CENPA | centromere protein A | 7 | | | | | | SLE vs HV |
| 373 | 1665 | DHX15 | DEAH (Asp-Glu-Ala-His) box polypeptide 15 | 7 | | | | | | SLE vs HV |
| 374 | 3092 | HIP1 | Huntingtin interacting protein 1 | 7 | | | | | | SLE vs HV |
| 375 | 3336 | HSPE1 | heat shock 10 kDa protein 1 (chaperonin 10) | 7 | | | | | | SLE vs HV |
| 376 | 5455 | POU3F3 | POU class 3 homeobox 3 | 7 | | | | | | SLE vs HV |
| 377 | 5918 | RARRES1 | retinoic acid receptor responder (tazarotene induced) 1 | 7 | | | | | | SLE vs HV |
| 378 | 6136 | RPL12 | ribosomal protein L12 | 7 | | | | | | SLE vs HV |
| 379 | 6626 | SNRPA | small nuclear ribonucleoprotein polypeptide A | 7 | | | | | | SLE vs HV |
| 380 | 6631 | SNRPC | small nuclear ribonucleoprotein polypeptide C | 7 | | | | | | SLE vs HV |
| 381 | 6757 | SSX2 | synovial sarcoma, X breakpoint 2 | 7 | | | | | | SLE vs HV |
| 382 | 9788 | MTSS1 | metastasis suppressor 1 | 7 | | | | | | SLE vs HV |
| 383 | 10134 | BCAP31 | B-cell receptor-associated protein 31 | 7 | | | | | | SLE vs HV |

TABLE 2-continued

List of all antigen reactivities

| SEQ ID No. | Gene GeneID | Gene Symbol | Gene Name | Group | Panel SLE | L. Nephr. | SLE Cluster | Statistical Test ENA-4 neg vs HV | L. Nephr. vs SLE | SLE vs control |
|---|---|---|---|---|---|---|---|---|---|---|
| 384 | 10522 | DEAF1 | deformed epidermal autoregulatory factor 1 (*Drosophila*) | 7 | | | | | | SLE vs HV |
| 385 | 10633 | RASL10A | RAS-like, family 10, member A | 7 | | | | | | SLE vs HV |
| 386 | 54795 | TRPM4 | transient receptor potential cation channel, subfamily M, member 4 | 7 | | | | | | SLE vs HV |
| 387 | 54913 | RPP25 | ribonuclease P/MRP 25 kDa subunit | 7 | | | | | | SLE vs HV |
| 388 | 54994 | C20orf11 | chromosome 20 open reading frame 11 | 7 | | | | | | SLE vs HV |
| 389 | 55727 | BTBD7 | BTB (POZ) domain containing 7 | 7 | | | | | | SLE vs HV |
| 390 | 79140 | CCDC28B | coiled-coil domain containing 28B | 7 | | | | | | SLE vs HV |
| 391 | 79613 | TMCO7 | transmembrane and coiled-coil domains 7 | 7 | | | | | | SLE vs HV |
| 392 | 5504 | PPP1R2 | protein phosphatase 1, regulatory (inhibitor) subunit 2 | 7 | | | | | | SLE vs HV |
| 393 | 8349 | HIST2H2BE | histone cluster 2, H2be | 7 | | | | | | SLE vs HV |
| 394 | 11168 | PSIP1 | PC4 and SFRS1 interacting protein 1 | 7 | | | | | | SLE vs HV |
| 395 | 149986 | LSM14B | LSM14B, SCD6 homolog B (*S. cerevisiae*) | 7 | | | | | | SLE vs HV |
| 396 | 655 | BMP7 | Bone morphogenetic protein 7 (osteogenic protein 1) | 7 | | | | | | SLE vs HV |
| 397 | 1676 | DFFA | DNA fragmentation factor, 45 kDa, alpha polypeptide | 7 | | | | | | SLE vs HV |
| 398 | 3071 | NCKAP1L | NCK-associated protein 1-like | 7 | | | | | | SLE vs HV |
| 399 | 3727 | JUND | jun D proto-oncogene | 7 | | | | | | SLE vs HV |
| 400 | 3960 | LGALS4 | lectin, galactoside-binding, soluble, 4 | 7 | | | | | | SLE vs HV |
| 401 | 4920 | ROR2 | Receptor tyrosine kinase-like orphan receptor 2 | 7 | | | | | | SLE vs HV |
| 402 | 7424 | VEGFC | vascular endothelial growth factor C | 7 | | | | | | SLE vs HV |
| 403 | 8906 | AP1G2 | adaptor-related protein complex 1, gamma 2 subunit | 7 | | | | | | SLE vs HV |
| 404 | 10297 | APC2 | adenomatosis polyposis coli 2 | 7 | | | | | | SLE vs HV |
| 405 | 10841 | FTCD | Formiminotransferase cyclodeaminase | 7 | | | | | | SLE vs HV |
| 406 | 11066 | SNRNP35 | small nuclear ribonucleoprotein 35 kDa (U11/U12) | 7 | | | | | | SLE vs HV |
| 407 | 11345 | GABARAPL2 | GABA(A) receptor-associated protein-like 2 | 7 | | | | | | SLE vs HV |
| 408 | 25854 | FAM149A | family with sequence similarity 149, member A | 7 | | | | | | SLE vs HV |
| 409 | 26065 | LSM14A | LSM14A, SCD6 homolog A (*S. cerevisiae*) | 7 | | | | | | SLE vs HV |

TABLE 2-continued

List of all antigen reactivities

| SEQ ID No. | Gene GeneID | Gene Symbol | Gene Name | Group | Panel SLE | Panel L. Nephr. | SLE Cluster | Statistical Test ENA-4 neg vs HV | L. Nephr. vs SLE | SLE vs control |
|---|---|---|---|---|---|---|---|---|---|---|
| 410 | 28998 | MRPL13 | mitochondrial ribosomal protein L13 | 7 | | | | | | SLE vs HV |
| 411 | 51520 | LARS | leucyl-tRNA synthetase | 7 | | | | | | SLE vs HV |
| 412 | 55747 | FAM21B | family with sequence similarity 21, member B | 7 | | | | | | SLE vs HV |
| 413 | 64841 | GNPNAT1 | glucosamine-phosphate N-acetyltransferase 1 | 7 | | | | | | SLE vs HV |
| 414 | 83483 | PLVAP | Plasmalemma vesicle associated protein | 7 | | | | | | SLE vs HV |
| 415 | 84968 | PNMA6A | paraneoplastic antigen like 6A | 7 | | | | | | SLE vs HV |
| 416 | 118430 | MUCL1 | Mucin-like 1 | 7 | | | | | | SLE vs HV |
| 417 | 122830 | NAT12 | N-acetyltransferase 12 | 7 | | | | | | SLE vs HV |
| 418 | 221092 | HNRNPUL2 | heterogeneous nuclear ribonucleoprotein U-like 2 | 7 | | | | | | SLE vs HV |
| 419 | 388962 | BOLA3 | bolA homolog 3 (*E. coli*) | 7 | | | | | | SLE vs HV |
| 420 | 729230 | FLJ78302 | Similar to C-C chemokine receptor type 2 (C-C CKR-2) (CC-CKR-2) (CCR-2) (CCR2) (Monocyte chemoattractant protein 1 receptor) (MCP-1-R) (CD192 antigen) | 7 | | | | | | SLE vs HV |
| 421 | 729447 | GAGE2A | G antigen 2A | 7 | | | | | | SLE vs HV |
| 422 | 1152 | CKB | No Gene Name; creatine kinase, brain | 7 | | | | | | SLE vs HV |
| 423 | 972 | CD74 | CD74 molecule, major histocompatibility complex, class II invariant chain | 7 | | | | | | SLE vs HV |
| 424 | 1397 | CRIP2 | cysteine-rich protein 2 | 7 | | | | | | SLE vs HV |
| 425 | 2040 | STOM | stomatin | 7 | | | | | | SLE vs HV |
| 426 | 2316 | FLNA | filamin A, alpha | 7 | | | | | | SLE vs HV |
| 427 | 4000 | LMNA | lamin A/C | 7 | | | | | | SLE vs HV |
| 428 | 4582 | MUC1 | mucin 1, cell surface associated | 7 | | | | | | SLE vs HV |
| 429 | 5230 | PGK1 | Phosphoglycerate kinase 1 | 7 | | | | | | SLE vs HV |
| 430 | 5340 | PLG | plasminogen | 7 | | | | | | SLE vs HV |
| 431 | 6525 | SMTN | smoothelin | 7 | | | | | | SLE vs HV |
| 432 | 8936 | WASF1 | WAS protein family, member 1 | 7 | | | | | | SLE vs HV |
| 433 | 23647 | ARFIP2 | ADP-ribosylation factor interacting protein 2 | 7 | | | | | | SLE vs HV |
| 434 | 6712 | SPTBN2 | spectrin, beta, non-erythrocytic 2 | 7 | | | | | | SLE vs HV |
| 435 | 6729 | SRP54 | signal recognition particle 54 kDa | 7 | | | | | | SLE vs HV |

TABLE 2-continued

List of all antigen reactivities

| SEQ ID No. | GeneID | Gene Symbol | Gene Name | Group | Panel SLE | L. Nephr. | SLE Cluster | Statistical Test ENA-4 neg vs HV | L. Nephr. vs SLE | SLE vs control |
|---|---|---|---|---|---|---|---|---|---|---|
| 436 | 9987 | HNRPDL | heterogeneous nuclear ribonucleoprotein D-like | 7 | | | | | | SLE vs HV |
| 437 | 337 | APOA4 | Apolipoprotein A-IV | 7 | | | | | | SLE vs HV |
| 438 | 950 | SCARB2 | scavenger receptor class B, member 2 | 7 | | | | | | SLE vs HV |
| 439 | 3183 | HNRNPC | heterogeneous nuclear ribonucleoprotein C (C1/C2) | 7 | | | | | | SLE vs HV |
| 440 | 3185 | HNRPF | Heterogeneous nuclear ribonucleoprotein F | 7 | | | | | | SLE vs HV |
| 441 | 3313 | HSPA9 | heat shock 70 kDa protein 9 (mortalin) | 7 | | | | | | SLE vs HV |
| 442 | 3467 | IFNW1 | Interferon, omega 1 | 7 | | | | | | SLE vs HV |
| 443 | 3799 | KIF5B | kinesin family member 5B | 7 | | | | | | SLE vs HV |
| 444 | 7918 | BAT4 | HLA-B associated transcript 4 | 7 | | | | | | SLE vs HV |
| 445 | 8337 | HIST2H2AA3 | histone cluster 2, H2aa3 | 7 | | | | | | SLE vs HV |
| 446 | 10195 | ALG3 | asparagine-linked glycosylation 3, alpha-1,3-mannosyltransferase homolog (*S. cerevisiae*) | 7 | | | | | | SLE vs HV |
| 447 | 23299 | BICD2 | bicaudal D homolog 2 (*Drosophila*) | 7 | | | | | | SLE vs HV |
| 448 | 80184 | CEP290 | centrosomal protein 290 kDa | 7 | | | | | | SLE vs HV |
| 449 | 90861 | HN1L | hematological and neurological expressed 1-like | 7 | | | | | | SLE vs HV |
| 450 | 349136 | WDR86 | WD repeat domain 86 | 7 | | | | | | SLE vs HV |
| | no Gene ID | dsDNA | dsDNA | 7 | | | | | | SLE vs HV |
| 451 | 60 | ACTB | actin, beta | 8 | | | | | | SLE vs HV |
| 452 | 498 | ATP5A1 | ATP synthase, H+ transporting, mitochondrial F1 complex, alpha subunit 1, cardiac muscle | 8 | | | | | | SLE vs HV |
| 453 | 506 | ATP5B | ATP synthase, H+ transporting, mitochondrial F1 complex, beta polypeptide | 8 | | | | | | SLE vs HV |
| 454 | 563 | AZGP1 | alpha-2-glycoprotein 1, zinc-binding | 8 | | | | | | SLE vs HV |
| 455 | 602 | BCL3 | B-cell CLL/lymphoma 3 | 8 | | | | | | SLE vs HV |
| 456 | 1729 | DIAPH1 | diaphanous-related formin 1 | 8 | | | | | | SLE vs HV |
| 457 | 1937 | EEF1G | eukaryotic translation elongation factor 1 gamma | 8 | | | | | | SLE vs HV |
| 458 | 1973 | EIF4A1 | eukaryotic translation initiation factor 4A1 | 8 | | | | | | SLE vs HV |

TABLE 2-continued

List of all antigen reactivities

| SEQ ID No. | Gene GeneID | Gene Symbol | Gene Name | Group | Panel SLE | Panel L. Nephr. | SLE Cluster | Statistical Test ENA-4 neg vs HV | L. Nephr. vs SLE | SLE vs control |
|---|---|---|---|---|---|---|---|---|---|---|
| 459 | 2280 | FKBP1A | FK506 binding protein 1A, 12 kDa | 8 | | | | | | SLE vs HV |
| 460 | 2495 | FTH1 | ferritin, heavy polypeptide 1 | 8 | | | | | | SLE vs HV |
| 461 | 2597 | GAPDH | glyceraldehyde-3-phosphate dehydrogenase | 8 | | | | | | SLE vs HV |
| 462 | 2819 | GPD1 | glycerol-3-phosphate dehydrogenase 1 (soluble) | 8 | | | | | | SLE vs HV |
| 463 | 3295 | HSD17B4 | hydroxysteroid (17-beta) dehydrogenase 4 | 8 | | | | | | SLE vs HV |
| 464 | 3305 | HSPA1L | heat shock 70 kDa protein 1-like | 8 | | | | | | SLE vs HV |
| 465 | 3312 | HSPA8 | heat shock 70 kDa protein 8 | 8 | | | | | | SLE vs HV |
| 466 | 4174 | MCM5 | minichromosome maintenance complex component 5 | 8 | | | | | | SLE vs HV |
| 467 | 4215 | MAP3K3 | mitogen-activated protein kinase kinase kinase 3 | 8 | | | | | | SLE vs HV |
| 468 | 4591 | TRIM37 | tripartite motif containing 37 | 8 | | | | | | SLE vs HV |
| 469 | 4691 | NCL | nucleolin | 8 | | | | | | SLE vs HV |
| 470 | 4898 | NRD1 | nardilysin (N-arginine dibasic convertase) | 8 | | | | | | SLE vs HV |
| 471 | 4904 | YBX1 | Y box binding protein 1 | 8 | | | | | | SLE vs HV |
| 472 | 5037 | PEBP1 | phosphatidylethanolamine binding protein 1 | 8 | | | | | | SLE vs HV |
| 473 | 5315 | PKM2 | pyruvate kinase, muscle | 8 | | | | | | SLE vs HV |
| 474 | 5481 | PPID | peptidylprolyl isomerase D | 8 | | | | | | SLE vs HV |
| 475 | 5684 | PSMA3 | proteasome (prosome, macropain) subunit, alpha type, 3 | 8 | | | | | | SLE vs HV |
| 476 | 6128 | RPL6 | ribosomal protein L6 | 8 | | | | | | SLE vs HV |
| 477 | 6129 | RPL7 | ribosomal protein L7 | 8 | | | | | | SLE vs HV |
| 478 | 6130 | RPL7A | ribosomal protein L7a | 8 | | | | | | SLE vs HV |
| 479 | 6132 | RPL8 | ribosomal protein L8 | 8 | | | | | | SLE vs HV |
| 480 | 6187 | RPS2 | ribosomal protein S2 | 8 | | | | | | SLE vs HV |
| 481 | 6189 | RPS3A | ribosomal protein S3A | 8 | | | | | | SLE vs HV |
| 482 | 6249 | CLIP1 | CAP-GLY domain containing linker protein 1 | 8 | | | | | | SLE vs HV |
| 483 | 6793 | STK10 | serine/threonine kinase 10 | 8 | | | | | | SLE vs HV |
| 484 | 6880 | TAF9 | TAF9 RNA polymerase II, TATA box binding protein (TBP)-associated factor, 32 kDa | 8 | | | | | | SLE vs HV |
| 485 | 7001 | PRDX2 | peroxiredoxin 2 | 8 | | | | | | SLE vs HV |
| 486 | 7552 | ZNF711 | zinc finger protein 711 | 8 | | | | | | SLE vs HV |

TABLE 2-continued

List of all antigen reactivities

| SEQ ID No. | Gene GeneID | Gene Symbol | Gene Name | Panel Group | SLE | L. Nephr. | SLE Cluster | ENA-4 neg vs HV | L. Nephr. vs SLE | SLE vs control |
|---|---|---|---|---|---|---|---|---|---|---|
| 487 | 8260 | ARD1A | N(alpha)-acetyltransferase 10, NatA catalytic subunit | 8 | | | | | | SLE vs HV |
| 488 | 8317 | CDC7 | cell division cycle 7 | 8 | | | | | | SLE vs HV |
| 489 | 8667 | EIF3H | eukaryotic translation initiation factor 3, subunit H | 8 | | | | | | SLE vs HV |
| 490 | 9223 | MAGI1 | membrane associated guanylate kinase, WW and PDZ domain containing 1 | 8 | | | | | | SLE vs HV |
| 491 | 9230 | RAB11B | RAB11B, member RAS oncogene family | 8 | | | | | | SLE vs HV |
| 492 | 9425 | CDYL | chromodomain protein, Y-like | 8 | | | | | | SLE vs HV |
| 493 | 9694 | EMC2 | ER membrane protein complex subunit 2 | 8 | | | | | | SLE vs HV |
| 494 | 10075 | HUWE1 | HECT, UBA and WWE domain containing 1, E3 ubiquitin protein ligase | 8 | | | | | | SLE vs HV |
| 495 | 10109 | ARPC2 | actin related protein 2/3 complex, subunit 2, 34 kDa | 8 | | | | | | SLE vs HV |
| 496 | 10180 | RBM6 | RNA binding motif protein 6 | 8 | | | | | | SLE vs HV |
| 497 | 10273 | STUB1 | STIP1 homology and U-box containing protein 1, E3 ubiquitin protein ligase | 8 | | | | | | SLE vs HV |
| 498 | 10432 | RBM14 | RNA binding motif protein 14 | 8 | | | | | | SLE vs HV |
| 499 | 10539 | GLRX3 | glutaredoxin 3 | 8 | | | | | | SLE vs HV |
| 500 | 10806 | SDCCAG8 | serologically defined colon cancer antigen 8 | 8 | | | | | | SLE vs HV |
| 501 | 11108 | PRDM4 | PR domain containing 4 | 8 | | | | | | SLE vs HV |
| 502 | 23002 | DAAM1 | dishevelled associated activator of morphogenesis 1 | 8 | | | | | | SLE vs HV |
| 503 | 23351 | KHNYN | KH and NYN domain containing | 8 | | | | | | SLE vs HV |
| 504 | 23589 | CARHSP1 | calcium regulated heat stable protein 1, 24 kDa | 8 | | | | | | SLE vs HV |
| 505 | 26986 | PABPC1 | poly(A) binding protein, cytoplasmic 1 | 8 | | | | | | SLE vs HV |
| 506 | 27072 | VPS41 | vacuolar protein sorting 41 homolog (S. cerevisiae) | 8 | | | | | | SLE vs HV |
| 507 | 30836 | DNTTIP2 | deoxynucleotidyltransferase, terminal, interacting protein 2 | 8 | | | | | | SLE vs HV |
| 508 | 51028 | VPS36 | vacuolar protein sorting 36 homolog (S. cerevisiae) | 8 | | | | | | SLE vs HV |

TABLE 2-continued

List of all antigen reactivities

| SEQ ID No. | GeneID | Gene Symbol | Gene Name | Group | Panel SLE | Panel L. Nephr. | SLE Cluster | ENA-4 neg vs HV | L. Nephr. vs SLE | SLE vs control |
|---|---|---|---|---|---|---|---|---|---|---|
| 509 | 51082 | POLR1D | polymerase (RNA) I polypeptide D, 16 kDa | 8 | | | | | | SLE vs HV |
| 510 | 51138 | COPS4 | COP9 signalosome subunit 4 | 8 | | | | | | SLE vs HV |
| 511 | 51466 | EVL | Enah/Vasp-like | 8 | | | | | | SLE vs HV |
| 512 | 54869 | EPS8L1 | EPS8-like 1 | 8 | | | | | | SLE vs HV |
| 513 | 54903 | MKS1 | Meckel syndrome, type 1 | 8 | | | | | | SLE vs HV |
| 514 | 57017 | COQ9 | coenzyme Q9 | 8 | | | | | | SLE vs HV |
| 515 | 57026 | PDXP | pyridoxal (pyridoxine, vitamin B6) phosphatase | 8 | | | | | | SLE vs HV |
| 516 | 57221 | ARFGEF3 | ARFGEF family member 3 | 8 | | | | | | SLE vs HV |
| 517 | 64753 | CCDC136 | coiled-coil domain containing 136 | 8 | | | | | | SLE vs HV |
| 518 | 80208 | SPG11 | spastic paraplegia 11 (autosomal recessive) | 8 | | | | | | SLE vs HV |
| 519 | 83858 | ATAD3B | ATPase family, AAA domain containing 3B | 8 | | | | | | SLE vs HV |
| 520 | 84893 | FBXO18 | F-box protein, helicase, 18 | 8 | | | | | | SLE vs HV |
| 521 | 129563 | DIS3L2 | DIS3 like 3'-5' exoribonuclease 2 | 8 | | | | | | SLE vs HV |
| 522 | 144097 | C11orf84 | chromosome 11 open reading frame 84 | 8 | | | | | | SLE vs HV |
| 523 | 256364 | EML3 | echinorm microtubule associated protein like 3 | 8 | | | | | | SLE vs HV |
| 524 | 347733 | TUBB2B | tubulin, beta 2B class IIb | 8 | | | | | | SLE vs HV |
| 525 | 3303 | HSPA1A | heat shock 70 kDa protein 1A | 8 | | | | | | SLE vs HV |
| 526 | 5163 | PDK1 | pyruvate dehydrogenase kinase, isozyme 1 | 8 | | | | | | SLE vs HV |
| 527 | 1001 | CDH3 | cadherin 3, type 1, P-cadherin (placental) | 8 | | | | | | SLE vs HV |

Example 9

Identification of Autoantibody Reactivities in ENA-4-Negative SLE Patients

In order to identify new SLE-specific autoantigens, the autoantibody profiles of new SLE-specific autoantigens were the autoantibody profiles of the group of SLE patients seropositive for the autoantigens Sm-protein, U1-RNP, Rho52/SS-A and Ro60/SS-B, with which the seronegative was compared. The result of the statistical test is summarised in Table 2.

Group 4 comprises additional antigens suitable for the identification of ENA-4-negative SLE patients.

FIG. 5 shows the volcano plot of the autoantibody reactivities of ENA-4-positives compared to ENA-4-negative SLE patients.

Example 10

Calculation of Antigen Panels for Improved Diagnosis of SLE

Due to the high clinical and serological heterogeneity of the SLE disease, it is not possible to diagnose this disease using just one biomarker. It is therefore necessary to combine (where possible) uncorrelated biomarker panels to form what are known as biomarker panels.

Group 1 of the antigens in Table 2 comprises the most important 24 antigens used for the calculation of biomarker panels for the diagnosis of SLE.

Table 4 shows different combinations of antigens which were used for the calculation of the biomarker panels (ENA-4, ENA-4+anti-rib, PI, PII, PIII, PVI, PV).

FIG. 6 shows the sensitivity and specificity and also the area under the curve (AUC) for the known 4 antigens compared with antigen panels that were calculated using a combination of the antigens from Table 2. Due to the inclusion of the 3 ribosomal antigens anti-rib) RPLP0, RPLP1 and RPLP2, the sensitivity could be increased already by 10% compared with the known 4 ENA antigens from 0.63 to 0.72. However, only a freely selected combination of known and new antigens could increase the sensitivity by 20% compared with the ENA-4 test to 0.8.

Antigens which have an adjusted p-value for the non-parametric mean value comparison between groups of <0.05, alongside a fold change of >1.5 and additionally an AUC resulting from the ROC analysis of >0.75 were selected on the basis of the univariate results for the generation of panels. In addition, the ENA-4 antigens were selected. For this pool of selected candidates, an L1-penalised logistic regression model was established within the scope of a nested cross validation. Antigens which were not taken into consideration within the scope of the model formation were removed from the further consideration. Within the remaining pools, panel contents were defined, for example in accordance with established markers and new markers.

Group 4 in Table 2 contains further statistically significant antigens which can be used for the identification of ENA-4-negative patients and for the definition of biomarker panels.

Group 6 in Table 2 contains further statistically significant antigens which can be used for the diagnosis and differential diagnosis of SLE compared with healthy controls and other autoimmune diseases.

TABLE 4

Composition of the diagnostic SLE Panel

| Gene Symbol | Gene Name | Antigen | ENA-4 | ENA-4 + anti-rib | PI | PII | PIII | PVI | PV |
|---|---|---|---|---|---|---|---|---|---|
| SNRPN SEQ ID NO. 14 | small nuclear ribonucleoprotein polypeptide N | Sm protein D | X | X | | X | | X | |
| TRIM21 SEQ ID NO. 19 | tripartite motif-containing 21 | SSA/R0 | X | X | X | X | | X | |
| TROVE2 SEQ ID NO. 20 | TROVE domain family, member 2 | SSA/Ro60 | X | X | X | X | | X | |
| SSB SEQ ID NO. 17 | Sjogren syndrome antigen B (autoantigen La) | SSB/La | X | X | X | X | | X | |
| SNRNP70 SEQ ID NO. 12 | small nuclear ribonucleoprotein 70 kDa (U1) | U1-RNP | X | X | X | X | | X | |
| SNRPB SEQ ID NO. 13 | small nuclear ribonucleoprotein polypeptides B and B1 | Sm protein B/B' | X | X | X | X | | X | |
| RPLP0 SEQ ID NO. 8 | ribosomal protein, large, P0 | anti-rib | | X | X | | X | X | |
| RPLP2 SEQ ID NO. 10 | ribosomal protein, large, P2 | anti-rib | | X | | | X | X | |
| RPLP1 SEQ ID NO. 9 | ribosomal protein, large, P1 | anti-rib | | X | | | X | X | |
| XRCC5 SEQ ID NO. 22 | X-ray repair complementing defective repair in Chinese hamster cells 5 (double-strand-break rejoining) | Ku80 | | | | | | | X |
| VIM SEQ ID NO. 21 | vimentin | | | | | | X | | X |
| SPTB SEQ ID NO. 16 | spectrin, beta, erythrocytic | | | | | | X | | X |
| DBT SEQ ID NO. 1 | dihydrolipoamide branched chain transacylase E2 | | | | X | X | X | X | X |
| EZR SEQ ID NO. 3 | ezrin | | | | X | X | X | X | X |
| HNRNPA2B1 SEQ ID NO. 6 | heterogeneous nuclear ribonucleoprotein A2/B1 | | | | | | X | | X |

TABLE 4-continued

Composition of the diagnostic SLE Panel

| Gene Symbol | Gene Name | Antigen | ENA-4 | ENA-4 + anti-rib | PI | PII | PIII | PVI | PV |
|---|---|---|---|---|---|---|---|---|---|
| TMPO SEQ ID NO. 18 | thymopoietin | | | | X | | X | X | X |
| MVP SEQ ID NO. 7 | major vault protein | | | | X | X | X | | X |
| ZNF574 SEQ ID NO. 24 | zinc finger protein 574 | | | | X | X | | | X |
| HIST1H2BD SEQ ID NO. 4 | histone cluster 1, H2bd | anti-Histone | | | | X | | | X |
| SH3KBP1 SEQ ID NO. 11 | SH3-domain kinase binding protein 1 | | | | | | | | X |
| ZNF217 SEQ ID NO. 23 | zinc finger protein 217 | | | | | | | X | X |
| SP100 SEQ ID NO. 15 | SP100 nuclear antigen | | | | X | X | X | X | X |
| HNRNPA1 SEQ ID NO. 5 | heterogeneous nuclear ribonucleoprotein A1 | | | | X | X | X | X | X |
| DLAT SEQ ID NO. 2 | dihydrolipoamide S-acetyltransferase | PDC-E2, M2 antigen | | | X | | X | X | X |

TABLE 5

AUC, sensitivity and specificity of the SLE panels

| | AUC | CI (AUC) | Sens. | CI (Sens.) | Spec. | CI (Spec) |
|---|---|---|---|---|---|---|
| a) SLE versus healthy controls | | | | | | |
| SLE vs PSS | | | | | | |
| Panel PI | 0.99 | [0.94, 0.98] | 0.83 | [0.77, 0.9] | 0.98 | [0.96, 1.0] |
| Panel PII | 0.90 | [0.84, 0.95] | 0.63 | [0.53, 0.73] | 0.94 | [0.91, 0.98] |
| Panel PIII | 0.91 | [0.87, 0.95] | 0.61 | [0.5, 0.72] | 0.95 | [0.92, 0.98] |
| Panel PIV | 0.90 | [0.86, 0.94] | 0.57 | [0.44, 0.71] | 0.95 | [0.91, 0.99] |
| Panel PV | 0.91 | [0.87, 0.96] | 0.64 | [0.52, 0.76] | 0.95 | [0.91, 0.99] |
| ENA-4 | 0.89 | [0.84, 0.94] | 0.63 | [0.49, 0.77] | 0.96 | [0.94, 0.98] |
| ENA-4 + anti-rib | 0.93 | [0.88, 0.98] | 0.72 | [0.6, 0.84] | 0.97 | [0.95, 0.99] |
| b) SLE versus SSc (PSS) | | | | | | |
| Panel PI | 0.9 | [0.85, 0.95] | 0.78 | [0.73, 0.83] | 0.83 | [0.71, 0.94] |
| Panel PII | 0.83 | [0.78, 0.88] | 0.72 | [0.61, 0.83] | 0.76 | [0.68, 0.85] |
| Panel PIII | 0.81 | [0.74, 0.88] | 0.68 | [0.56, 0.79] | 0.75 | [0.6, 0.89] |
| panel PIV | 0.83 | [0.78, 0.88] | 0.69 | [0.58, 0.81] | 0.77 | [0.67, 0.87] |
| Panel PV | 0.84 | [0.79, 0.9] | 0.71 | [0.62, 0.8] | 0.76 | [0.65, 0.87] |
| ENA-4 | 0.75 | [0.66, 0.85] | 0.6 | [0.5, 0.7] | 0.8 | [0.71, 0.88] |
| ENA-4 + anti-rib | 0.82 | [0.74, 0.9] | 0.63 | [0.51, 0.75] | 0.83 | [0.74, 0.93] |
| c) SLE versus all AID (early RA, SSc, SPA) | | | | | | |
| SLE vs Pool (EA, PSS, SPA) | | | | | | |
| Panel PI | 0.94 | [0.91, 0.96] | 0.6 | [0.51, 0.69] | 0.98 | [0.98, 0.99] |
| Panel PII | 0.83 | [0.78, 0.89] | 0.26 | [0.16, 0.35] | 0.98 | [0.97, 0.99] |
| Panel PIII | 0.83 | [0.74, 0.92] | 0.27 | [0.16, 0.37] | 0.99 | [0.98, 1] |
| Panel PIV | 0.83 | [0.79, 0.87] | 0.19 | [0.1, 0.28] | 0.98 | [0.97, 0.99] |

TABLE 5-continued

AUC, sensitivity and specificity of the SLE panels

|  | AUC | CI (AUC) | Sens. | CI (Sens.) | Spec. | CI (Spec) |
|---|---|---|---|---|---|---|
| Panel PV | 0.85 | [0.78, 0.91] | 0.34 | [0.22, 0.46] | 0.99 | [0.98, 0.99] |
| ENA-4 | 0.84 | [0.79, 0.9] | 0.35 | [0.22, 0.47] | 0.99 | [0.98, 0.99] |
| ENA-4 + anti-rib | 0.91 | [0.88, 0.93] | 0.49 | [0.41, 0.58] | 0.98 | [0.97, 0.99] |

Example 11

Identification of Lupus Nephritis Patients

The autoantibody profiles of SLE patients with lupus nephritis were compared with those of SLE patients without lupus nephritis. Following univariate statistical evaluation, a threshold value of p<0.05 and a 1.5 times modified reactivity compared with the control group were applied. 85 antigens met these criteria and are detailed in Table 2.

FIG. 7 shows the volcano plot of the sera compared with selected lupus nephritis antigens.

Group 2 in Table 2 contains 30 additional and important antigens which can be used for the generation of lupus nephritis biomarker panels.

An L1-penalised logistic regression model with five-fold cross validation and twenty times repetition was computed for the selection of the best candidates. The antigens selected most frequently in this model computation with a frequency of more than 50% constituted the best candidates for the diagnosis of lupus nephritis.

FIG. 8 shows the frequency distribution of the lupus nephritis antigens.

Group 5 comprises further statistically significant antigens suitable for the diagnosis of lupus nephritis.

Example 12

Identification of SLE Subforms and Subgroups

The large clinical heterogeneity of SLE constitutes a big problem both for diagnosis and active substance development.

The identification of specific antibody signatures in SLE patient subgroups thus constitutes a key step for the improved definition of patient groups in clinical studies. By way of example, as presented under Example 9, specific antibodies for lupus nephritis could be used to recruit this subgroup for drug studies.

A large number of new active substances and therapeutic antibodies are currently undergoing clinical development: inter alia, therapeutic antibodies against cell-surface receptors of immune cells, such as anti-CD20, anti-CD22, or against pro-inflammatory cytokines, such as anti-IL6, are being developed. It is therefore now possible, due to the identification of serologically-defined subgroups of SLE, to link this to a target-specific response to a drug.

It was first examined whether, on the basis of the typical ENA antigens and ribosomal antigens, different autoantibody signatures can already be identified in SLE patients and thus patient subgroups.

FIGS. 9a and b show a dendogram of the SLE antigens after calculation of Spearman's rank correlation coefficient FIG. 9a shows a dendogram for the antigens Sm, SS-B, Ro-52/SS-A, Ro60-SS-B and three ribosomal proteins.

3 antigen clusters can be already be defined on the basis of these 7 antigens.

For an improved definition of SLE subgroups, however, a larger number of antigens are necessary. 50 antigens from Table 2 were therefore selected, and the correlation thereof in SLE patients was examined by calculation of Spearman's rank correlation coefficient.

Group 3 contains 37 of the most important antigens necessary for the characterisation of SLE subgroups. Further antigens have already been defined in group 1 and group 2.

The presentation of the antigens as a dendogram shows groups of antigens of which the reactivities in SLE patients are correlated with one another.

As illustrated in FIG. 9b, at least 6 groups of correlated antigens can be identified as a result.

Interestingly, one of the clusters includes the antigens MVP, MIER2, CCS, DCAF6, which were identified in the table as biomarkers for lupus nephritis.

Due to the calculation of a PPLS-DA-based regression model, it is possible to visualise how well the selected antigens contribute to the discrimination of the SLE patients from healthy controls.

Figure 10A:
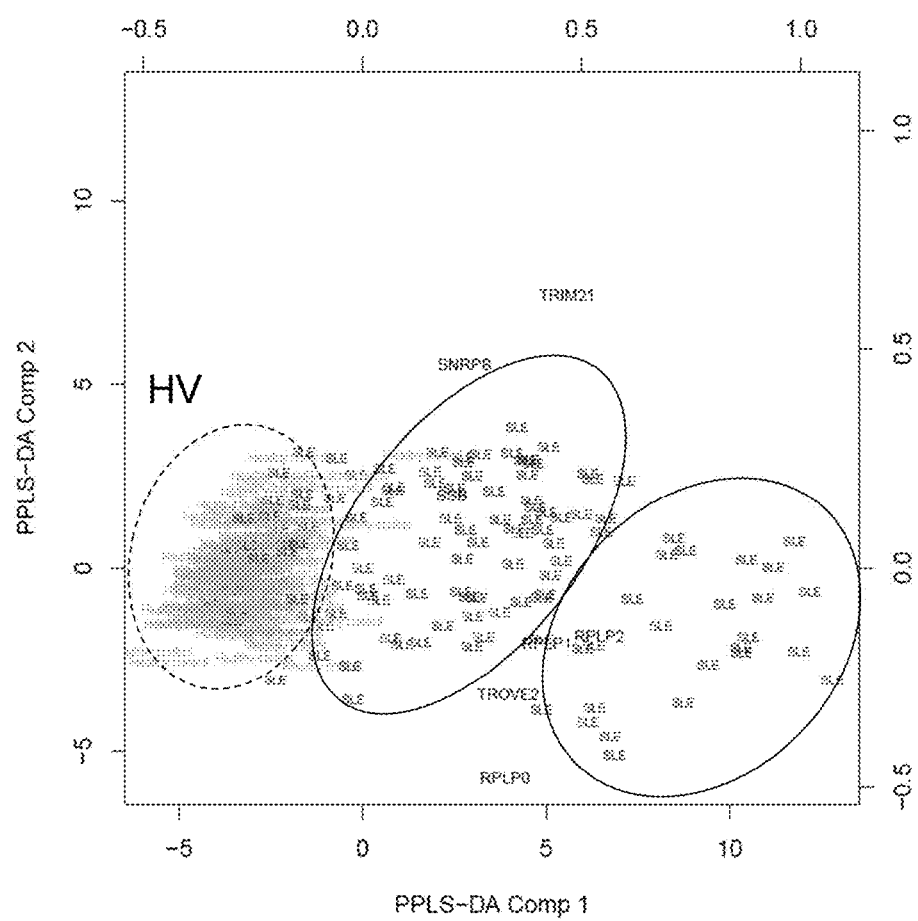

FIGS. 10a and b show the PPLS-DA biplot of the SLE patients and healthy controls with use of the SLE antigens.

FIG. 10a shows a PPLS-DA biplot for the selected ENA antigens and ribosomal proteins and measured values thereof in the SLE patients. FIG. 10a shows that the separation of healthy and SLE is not complete and that some SLE patients coincide with the group of healthy samples. However, there is already a division of the SLE patients into 2 clusters with just few antigens.

Figure 10B:
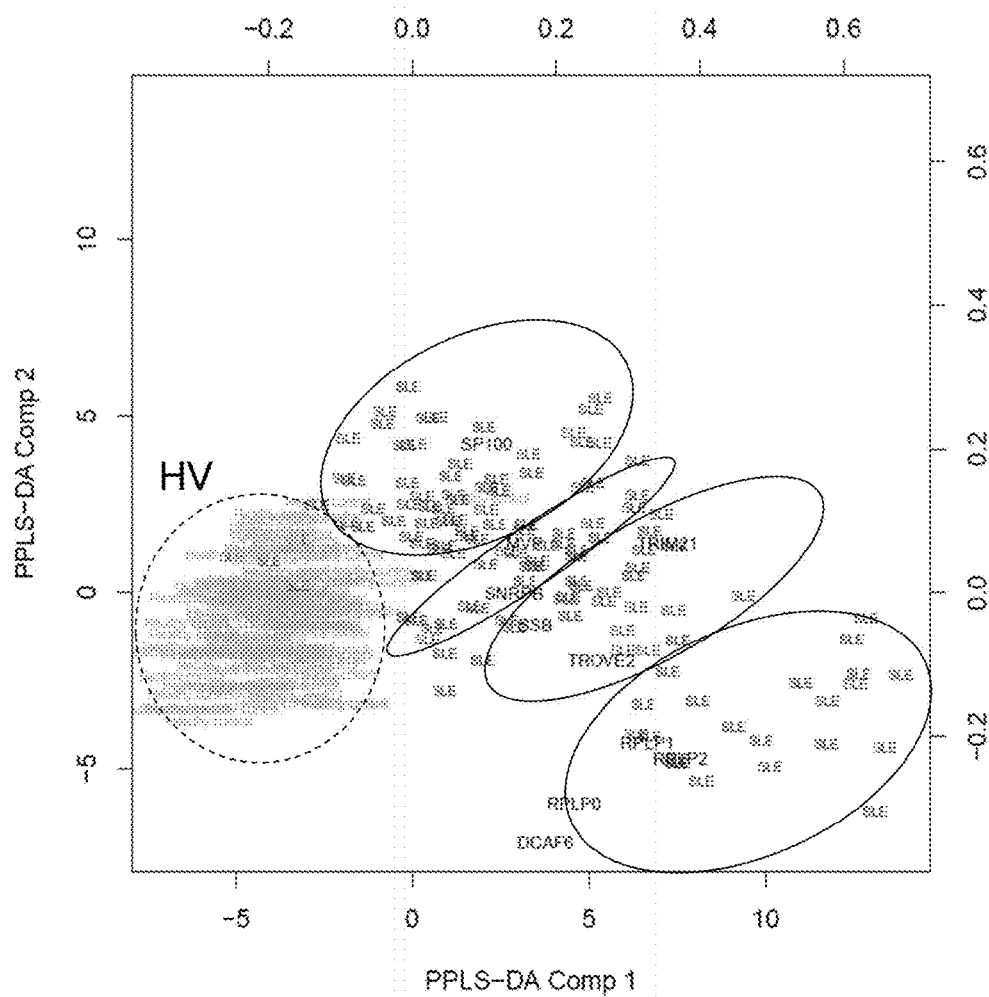

FIG. 10b shows a PPLS-DA biplot for 50 antigens which are contained in Table 2. The selection of further antigens results in a practically perfect separation of the SLE patients and healthy samples.

A further subdivision of the SLE patients into possible subgroups is provided by 50 antigens. These subgroups can be defined by specific antigens, some of which have been highlighted by way of example.

Example 13

Validation of SLE Antigens in an Independent Test Cohort II

For validation of the SLE-associated autoantigens specified in Table 2, the autoantibody reactivity in serum samples of a further independent cohort of 101 SLE patients, 105 healthy controls and 89 samples of the SLE cohort from Example 6 was measured. For this purpose the 529 human proteins specified in Table 2 (SEQ ID No. 1057 to 1584), and double-stranded DNA (dsDNA) thereof, were coupled to Luminex beads, and the antigen-coupled beads were measured in a multiplex assay with the patient samples. The binding of autoantibodies was measured by means of a PE-conjugated autoantibody in a Luminex instrument.

Following univariate statistical evaluation, a threshold value of p<0.05 (Wilcoxon rank-sum test) compared with the control group was applied.

A list of the significance values (p-values) for autoantibodies against 50 antigens in the SLE cohort II is shown in Table 6. Of the 50 antigens, 43 antigens in cohort I and cohort II achieved a p-value <0.05.

The frequency (in %) of autoantibodies against 50 antigens in the three SLE cohorts is shown in Table 7.

Figure 11:
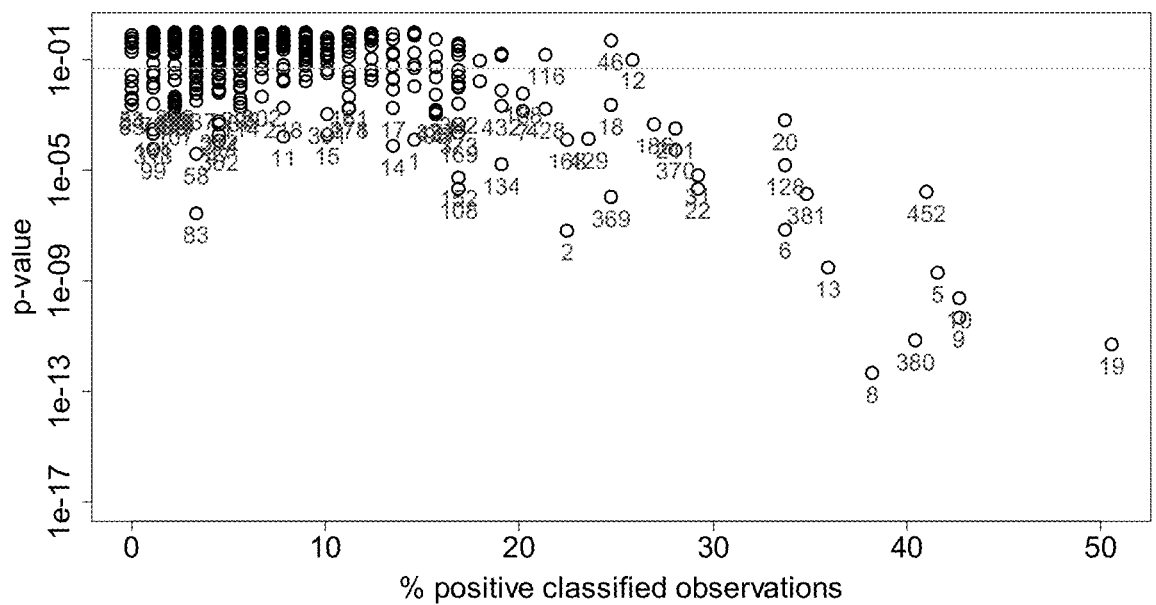
Figure 11:
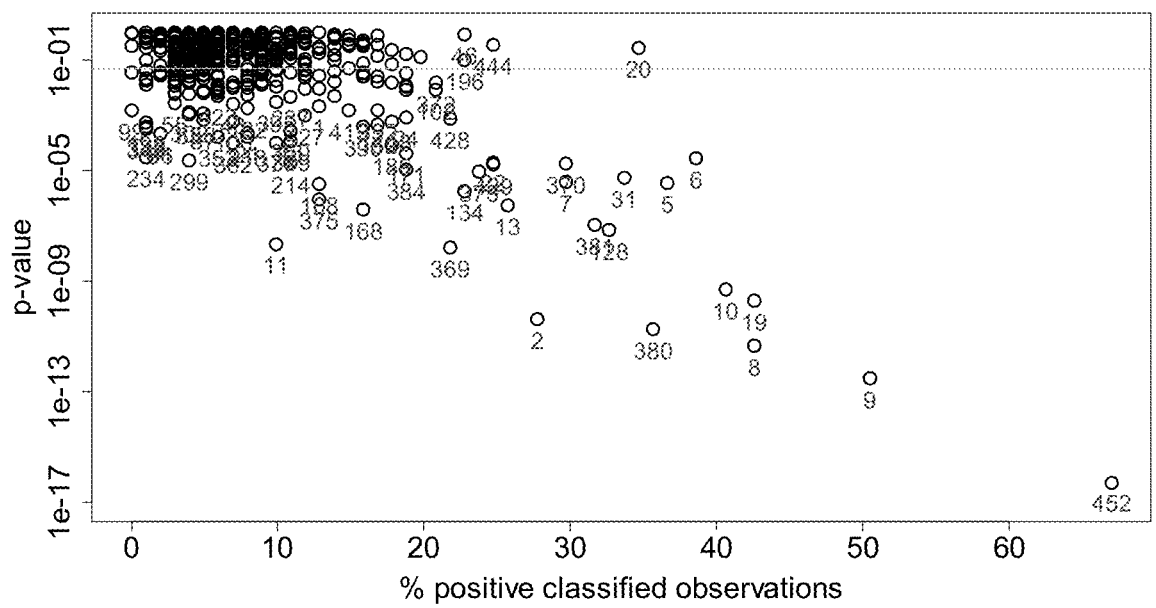
Figure 11:
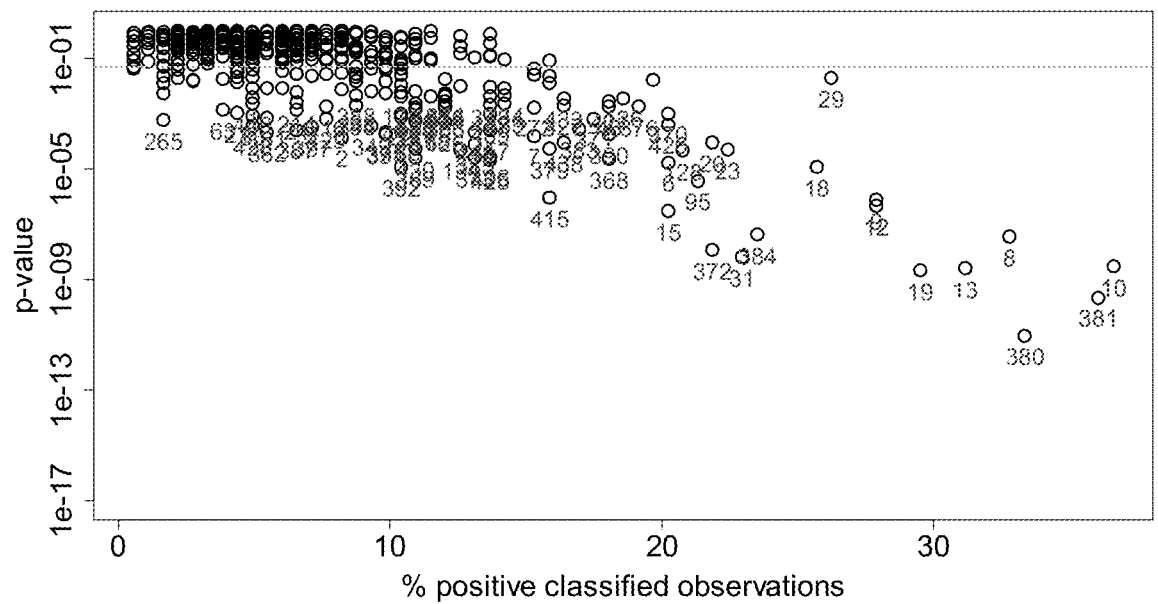

FIG. 11: shows the calculated p-value of the antigens from Table 2 and also the frequency of SLE patients who were classified as autoantibody-positive for this antigen.

Example 14

Validation of SLE Autoantigens in a Third Independent Test Cohort III

For validation of the SLE-associated autoantigens specified in Table 2, the autoantibody reactivity in serum samples of an independent cohort of 183 SLE patients and 109 healthy controls was measured. For this purpose, 6,912 human proteins were coupled to Luminex beads and the protein-coupled beads were measured in a multiplex assay with the patient samples. The binding of autoantibodies was measured by means of a PE-conjugated autoantibody in a Luminex instrument.

After univariate statistical evaluation, a threshold value of $p<0.05$ and a Cohen's d effect size of greater than 0.3 compared to the control group was provided.

A list of the significance values is shown in Table 6. The table contains selected markers which are part of the panels ENA+anti-rib, panel I, panel VI, panel VII and panel VIII.

The table contains further markers which achieved a p-value of <0.05 in all three cohorts.

TABLE 6 significance values (p-values) of 50 antigens in 3 SLE cohorts

| Seq. Nr | GeneID | Gene Symbol | SLE cohort I | SLE cohort II | SLE cohort III | Panel |
|---|---|---|---|---|---|---|
| 1 | 1629 | DBT | 1.28E−04 | 2.16E−03 | 3.82E−03 | Panel I; II; III; IV; V; VII |
| 2 | 1737 | DLAT | 6.33E−08 | 4.12E−11 | 1.31E−04 | Panel I; III; IV; VI; VII |
| 3 | 7430 | EZR | 1.44E−03 | 2.68E−01 | 9.79E−02 | panel I; II; III; IV |
| 4 | 3017 | HIST1H2BD | 9.43E−01 | 4.08E−01 | 4.00E−02 | Panel II, V |
| 5 | 3178 | HNRNPA1 | 1.99E−09 | 3.60E−06 | 2.81E−04 | Panel I; II, III; IV; V; VI; VII |
| 6 | 3181 | HNRNPA2B1 | 7.31E−08 | 2.81E−05 | 1.70E−05 | Panel III; V; VI; VII |
| 7 | 9961 | MVP | 1.40E−03 | 3.90E−06 | 1.56E−04 | Panel I; II; III; V; VI; VII |
| 8 | 6175 | RPLP0 | 4.59E−13 | 4.75E−12 | 3.51E−08 | ENA-4 + anti-rib, Panel I; III; VI; VII |
| 9 | 6176 | RPLP1 | 4.61E−11 | 3.05E−13 | 7.50E−07 | ENA-4 + anti-rib; Panel III; IV; VII |
| 10 | 6181 | RPLP2 | 2.38E−10 | 5.18E−10 | 2.94E−09 | ENA-4 + anti-rib; Panel I; VI; VII |
| 11 | 30011 | SH3KBP1 | 1.68E−04 | 2.22E−08 | 2.64E−02 | Panel V |
| 12 | 6625 | SNRNP70 | 4.87E−02 | 9.02E−02 | 1.22E−08 | ENA-4 + anti-rib; Panel I; II; IV |
| 13 | 6628 | SNRPB | 2.95E−09 | 5.57E−07 | 2.49E−09 | ENA-4 + anti-rib; Panel I; II; IV; VI; VII |
| 14 | 6638 | SNRPN | 7.44E−05 | 2.61E−02 | 3.64E−02 | ENA-4 + anti-rib, Panel II; Panel IV |
| 15 | 6672 | SP100 | 1.98E−04 | 2.47E−04 | 3.04E−07 | Panel I; II; III; IV; V; VII |
| 16 | 6710 | SPTB | 7.76E−06 | 5.13E−01 | 8.37E−01 | Panel III; V |
| 17 | 6741 | SSB | 1.75E−03 | 3.20E−02 | 7.82E−02 | ENA-4 + anti-rib; Panel I; II; IV |
| 18 | 7112 | TMPO | 2.20E−03 | 3.15E−02 | 1.15E−05 | Panel I; II; III; IV; VI |
| 19 | 6737 | TRIM21 | 5.07E−12 | 1.96E−10 | 6.35E−10 | Panel I; II; iV; VI; VII |
| 20 | 6738 | TROVE2 | 6.11E−04 | 2.59E−01 | 9.27E−05 | ENA-4 + anti-rib; Panel I; II; IV |
| 21 | 7431 | VIM | 2.37E−01 | 2.25E−04 | 1.06E−03 | Panel III; V |
| 22 | 7520 | XRCC5 | 2.06E−06 | 2.01E−05 | 7.83E−04 | Panel V; VI; VII |
| 23 | 7764 | ZNF217 | 3.28E−01 | 1.55E−01 | 5.04E−05 | Panel III; V |
| 24 | 64763 | ZNF574 | 1.02E−02 | 8.36E−05 | 1.33E−03 | Panel I; II; V; VII |
| 31 | 9973 | CCS | 6.65E−06 | 5.28E−06 | 6.62E−09 | Panel VII |
| 95 | 6629 | SNRPB2 | 1.06E−03 | 8.68E−03 | 3.66E−06 | Panel VIII |
| 128 | 10970 | CKAP4 | 1.52E−05 | 7.26E−08 | 4.60E−05 | Panel VIII |
| 134 | 1743 | DLST | 1.63E−05 | 1.78E−06 | 4.95E−05 | Panel VIII |
| 168 | 4841 | NONO | 1.27E−04 | 3.76E−07 | 5.17E−04 | Panel VI; VII |
| 169 | 29982 | NRBF2 | 2.22E−04 | 2.44E−02 | 7.44E−03 | Panel VIII |
| 171 | 4926 | NUMA1 | 1.62E−03 | 4.28E−05 | 4.31E−03 | Panel VIII |
| 213 | 7791 | ZYX | 4.54E−04 | 1.77E−05 | 2.57E−03 | Panel VII |
| 367 | 4670 | HNRNPM | 7.61E−03 | 8.98E−03 | 2.34E−05 | Panel VII |
| 368 | 10540 | DCTN2 | 1.11E−06 | 1.69E−08 | 2.49E−05 | Panel VII |

TABLE 6-continued significance values (p-values) of 50 antigens in 3 SLE cohorts

| Seq. Nr | GeneID | Gene Symbol | SLE cohort I | SLE cohort II | SLE cohort III | Panel |
|---|---|---|---|---|---|---|
| 369 | 10938 | EHD1 | 5.60E−05 | 1.73E−05 | 1.01E−03 | Panel VII |
| 371 | 684 | BST2 | 2.51E−02 | 1.44E−02 | 1.13E−08 | Panel VIII |
| 372 | 1058 | CENPA | 4.45E−04 | 8.70E−06 | 2.51E−05 | Panel VIII |
| 374 | 3092 | HIP1 | 4.42E−02 | 8.73E−07 | 2.03E−04 | Panel VIII |
| 375 | 3336 | HSPE1 | 2.15E−02 | 1.42E−02 | 1.73E−03 | Panel VIII |
| 376 | 5455 | POU3F3 | 1.31E−03 | 1.02E−04 | 6.18E−03 | Panel VIII |
| 379 | 6626 | SNRPA | 7.16E−12 | 1.85E−11 | 2.60E−16 | Panel VIII |
| 380 | 6631 | SNRPC | 1.42E−06 | 1.06E−07 | 3.73E−15 | Panel VIII |
| 381 | 6757 | SSX2 | 2.40E−03 | 1.78E−02 | 2.09E−04 | Panel VIII |
| 383 | 10134 | BCAP31 | 4.10E−02 | 1.04E−05 | 4.34E−08 | Panel VIII |
| 389 | 55727 | BTBD7 | 3.33E−02 | 3.68E−04 | 1.79E−04 | Panel VIII |
| 427 | 4000 | LMNA | 1.59E−03 | 7.49E−04 | 3.41E−04 | Panel VIII |
| 428 | 4582 | MUC1 | 1.35E−04 | 1.66E−05 | 6.29E−04 | Panel VIII |
| 430 | 5340 | PLG | 1.22E−03 | 1.64E−02 | 5.61E−03 | Panel VIII |
| 431 | 6525 | SMTN | 2.05E−03 | 1.53E−02 | 9.78E−03 | Panel VIII |
| 451 | dsDNA | dsDNA | 1.65E−06 | 5.35E−17 | NA | dsDNA |

TABLE 7

List of the frequency of SLE patients positively tested for autoantibodies in 3 independent cohorts. The frequency in % of individuals positively tested for autoantibodies from Table 6 was calculated by means of the 95% quantile of healthy controls.

Proportion of SLE patients positively tested for autoantibodies (%) based on the 95% quantile of the control group

| Seq. Nr. | GeneID | Gene Symbol | SLE cohort I | SLE cohort II | SLE cohort III | Panel |
|---|---|---|---|---|---|---|
| 1 | 1629 | DBT | 1.28E−04 | 2.16E−03 | 3.82E−03 | Panel I; II; III; IV; V; VII |
| 2 | 1737 | DLAT | 6.33E−08 | 4.12E−11 | 1.31E−04 | Panel I; III; IV; VI; VII |
| 3 | 7430 | EZR | 1.44E−03 | 2.68E−01 | 9.79E−02 | panel I; II; III; IV |
| 4 | 3017 | HIST1H2BD | 9.43E−01 | 4.08E−01 | 4.00E−02 | Panel II, V |
| 5 | 3178 | HNRNPA1 | 1.99E−09 | 3.60E−06 | 2.81E−04 | Panel I; II, III; IV; VI; VII |
| 6 | 3181 | HNRNPA2B1 | 7.31E−08 | 2.81E−05 | 1.70E−05 | Panel III; V; VI; VII |
| 7 | 9961 | MVP | 1.40E−03 | 3.90E−06 | 1.56E−04 | Panel I; II; III; V; VI; VII |
| 8 | 6175 | RPLP0 | 4.59E−13 | 4.75E−12 | 3.51E−08 | ENA-4 + anti-rib, Panel I; III; VI; VII |
| 9 | 6176 | RPLP1 | 4.61E−11 | 3.05E−13 | 7.50E−07 | ENA-4 + anti-rib; Panel III; IV; VII |
| 10 | 6181 | RPLP2 | 2.38E−10 | 5.18E−10 | 2.94E−09 | ENA-4 + anti-rib; Panel I; VI; VII |
| 11 | 30011 | SH3KBP1 | 1.68E−04 | 2.22E−08 | 2.64E−02 | Panel V |
| 12 | 6625 | SNRNP70 | 4.87E−02 | 9.02E−02 | 1.22E−08 | ENA-4 + anti-rib; Panel I; II; IV |
| 13 | 6628 | SNRPB | 2.95E−09 | 5.57E−07 | 2.49E−09 | ENA-4 + anti-rib; Panel I; II; IV; VI; VII |
| 14 | 6638 | SNRPN | 7.44E−05 | 2.61E−02 | 3.64E−02 | ENA-4 + anti-rib, Panel II; Panel IV |
| 15 | 6672 | SP100 | 1.98E−04 | 2.47E−04 | 3.04E−07 | Panel I; II; III; IV; V; VII |

TABLE 7-continued

List of the frequency of SLE patients positively
tested for autoantibodies in 3 independent cohorts.
The frequency in % of individuals positively tested for
autoantibodies from Table 6 was calculated by means of the 95%
quantile of healthy controls.

| Seq. Nr. | GeneID | Gene Symbol | SLE cohort I | SLE cohort II | SLE cohort III | Panel |
|---|---|---|---|---|---|---|
| | | | | | Proportion of SLE patients positively tested for autoantibodies (%) based on the 95% quantile of the control group | |
| 16 | 6710 | SPTB | 7.76E−06 | 5.13E−01 | 8.37E−01 | Panel III; V |
| 17 | 6741 | SSB | 1.75E−03 | 3.20E−02 | 7.82E−02 | ENA-4 + anti-rib; Panel I; II; IV |
| 18 | 7112 | TMPO | 2.20E−03 | 3.15E−02 | 1.15E−05 | Panel I; II; III; IV; VI |
| 19 | 6737 | TRIM21 | 5.07E−12 | 1.96E−10 | 6.35E−10 | Panel I; II; iV; VI; VII |
| 20 | 6738 | TROVE2 | 6.11E−04 | 2.59E−01 | 9.27E−05 | ENA-4 + anti-rib; Panel I; II; IV |
| 21 | 7431 | VIM | 2.37E−01 | 2.25E−04 | 1.06E−03 | Panel III; V |
| 22 | 7520 | XRCC5 | 2.06E−06 | 2.01E−05 | 7.83E−04 | Panel V; VI; VII |
| 23 | 7764 | ZNF217 | 3.28E−01 | 1.55E−01 | 5.04E−05 | Panel III; V |
| 24 | 64763 | ZNF574 | 1.02E−02 | 8.36E−04 | 1.33E−03 | Panel I; II; V; VII |
| 31 | 9973 | CCS | 6.65E−06 | 5.28E−06 | 6.62E−09 | Panel VII |
| 95 | 6629 | SNRPB2 | 1.06E−03 | 8.68E−03 | 3.66E−06 | Panel VIII |
| 128 | 10970 | CKAP4 | 1.52E−05 | 7.26E−08 | 4.60E−05 | Panel VIII |
| 134 | 1743 | DLST | 1.63E−05 | 1.78E−06 | 4.95E−05 | Panel VII |
| 168 | 4841 | NONO | 1.27E−04 | 3.76E−07 | 5.17E−04 | Panel VI; VII |
| 169 | 29982 | NRBF2 | 2.22E−04 | 2.44E−02 | 7.44E−03 | Panel VIII |
| 171 | 4926 | NUMA1 | 1.62E−03 | 4.28E−05 | 4.31E−03 | Panel VIII |
| 213 | 7791 | ZYX | 4.54E−04 | 1.77E−05 | 2.57E−03 | Panel VII |
| 367 | 4670 | HNRNPM | 7.61E−03 | 8.98E−03 | 2.34E−05 | Panel VII |
| 368 | 10540 | DCTN2 | 1.11E−06 | 1.69E−08 | 2.49E−05 | Panel VII |
| 369 | 10938 | EHD1 | 5.60E−05 | 1.73E−05 | 1.01E−03 | Panel VII |
| 371 | 684 | BST2 | 2.51E−02 | 1.44E−02 | 1.13E−08 | Panel VIII |
| 372 | 1058 | CENPA | 4.45E−04 | 8.70E−06 | 2.51E−05 | Panel VIII |
| 374 | 3092 | HIP1 | 4.42E−02 | 8.73E−07 | 2.03E−04 | Panel VIII |
| 375 | 3336 | HSPE1 | 2.15E−02 | 1.42E−02 | 1.73E−03 | Panel VIII |
| 376 | 5455 | POU3F3 | 1.31E−03 | 1.02E−04 | 6.18E−03 | Panel VIII |
| 379 | 6626 | SNRPA | 7.16E−12 | 1.85E−11 | 2.60E−16 | Panel VIII |
| 380 | 6631 | SNRPC | 1.42E−06 | 1.06E−07 | 3.73E−15 | Panel VIII |
| 381 | 6757 | SSX2 | 2.40E−03 | 1.78E−02 | 2.09E−04 | Panel VIII |
| 383 | 10134 | BCAP31 | 4.10E−02 | 1.04E−05 | 4.34E−08 | Panel VIII |
| 389 | 55727 | BTBD7 | 3.33E−02 | 3.68E−04 | 1.79E−04 | Panel VIII |
| 427 | 4000 | LMNA | 1.59E−03 | 7.49E−04 | 3.41E−04 | Panel VIII |
| 428 | 4582 | MUC1 | 1.35E−04 | 1.66E−05 | 6.29E−04 | Panel VIII |
| 430 | 5340 | PLG | 1.22E−03 | 1.64E−02 | 5.61E−03 | Panel VIII |
| 431 | 6525 | SMTN | 2.05E−03 | 1.53E−02 | 9.78E−03 | Panel VIII |
| dsDNA | dsDNA | | 1.65E−06 | 5.35E−17 | NA | dsDNA |

Example

Calculation of Biomarker Panels

As shown in Table 7, only at most approximately 60% of the SLE patients had antibodies for a specific autoantigen. In order to therefore increase the sensitivity of the diagnostic autoantibodies, such as anti-dsDNA, SSA-Ro (TRIM21/TROVE2) and U1-RNP (SNRNP70, SNRPNA, SNRNPC), new methods with which autoantibodies can be combined to form what are known as biomarker panels were tested.

For this pool of selected candidates, a logistic regression was carried out for panels PI to PVII. An L1-penalised logistic regression model was established within the scope of a nested cross validation for panels PVIII to PXI. Antigens which were not considered within the scope of the model formation were removed from the further consideration. The content of panels was defined within the remaining pool, for example in accordance with established markers and new markers.

The antigens specified in Table 2 were used for the calculation of biomarker panels for the diagnosis of SLE.

Table 4 shows different combinations of antigens which were used for the calculation of the biomarker panels (ENA-4, ENA-4+anti-rib, PI, PII, PIII, PVI, PV).

Table 8 shows further different combinations of antigens which were used for the calculation of panels and which were selected on account of their significance and reactivity in three SLE cohorts.

TABLE 8

Combinations of antigens from Table 2:

| Seq. ID Nr | GeneID | Gene Symbol | Panel ENA-4 | +anti-rib | Panel PI | Panel PII | Panel PIII | Panel PIV | Panel PV | Panel VI | Panel VII | Panel VIII | Panel IX | Panel X* | Panel XI* |
|---|---|---|---|---|---|---|---|---|---|---|---|---|---|---|---|
| 1 | 1629 | DBT | | | x | x | x | x | x | | x | x | x | x | x |
| 2 | 1737 | DLAT | | | x | | x | x | x | x | x | x | x | x | x |
| 5 | 3178 | HNRNPA1 | | | x | x | x | x | | x | x | x | x | x | x |
| 6 | 3181 | HNRNPA2B1 | | | | | x | x | x | x | x | x | x | x | x |
| 7 | 9961 | MVP | | | x | x | x | | x | | | x | x | x | x |
| 8 | 6175 | RPLP0 | | x | x | | x | x | | x | | x | x | x | x |
| 9 | 6176 | RPLP1 | | x | | | x | x | | | x | x | x | x | x |
| 10 | 6181 | RPLP2 | | x | x | | x | x | | x | | x | x | x | x |
| 13 | 6628 | SNRPB | x | x | x | x | | x | | x | | x | x | x | x |
| 15 | 6672 | SP100 | | | x | x | x | x | x | | x | x | x | x | x |
| 19 | 6737 | TRIM21 | x | x | x | x | | x | | x | | x | x | x | x |
| 22 | 7520 | XRCC5 | | | | | | | | x | x | x | x | x | x |
| 24 | 64763 | ZNF574 | | | x | x | | | x | | x | x | x | x | x |
| 134 | 1743 | DLST | | | | | | | | x | x | x | x | x | x |
| 168 | 4841 | NONO | | | | | | | | | x | x | x | x | x |
| 213 | 7791 | ZYX | | | | | | | | | x | x | x | x | x |
| 367 | 4670 | HNRNPM | | | | | | | | | x | x | x | x | x |
| 368 | 10540 | DCTN2 | | | | | | | | | x | x | x | x | x |
| 369 | 10938 | EHD1 | | | | | | | | | x | x | x | x | x |
| 4 | 3017 | HIST1H2BD | | | | x | | x | | | | x | x | x | x |
| 12 | 6625 | SNRNP70 | x | x | x | x | | x | | | | x | x | x | x |
| 17 | 6741 | SSB | x | x | x | x | | x | | | | x | x | x | x |
| 18 | 7112 | TMPO | | | x | x | x | x | x | x | | x | x | x | x |
| 20 | 6738 | TROVE2 | x | x | x | x | | x | | | | x | x | x | x |
| 21 | 7431 | VIM | | | | | x | | x | | | x | x | x | x |
| 23 | 7764 | ZNF217 | | | | | x | | x | | | x | x | x | x |
| 29 | 9478 | CABP1 | | | | | | | | | | x | x | x | x |
| 31 | 9973 | CCS | | | | | | | | | | x | x | x | x |
| 46 | 4869 | NPM1 | | | | | | | | | | x | x | x | x |
| 95 | 6629 | SNRPB2 | | | | | | | | | | x | x | x | x |
| 128 | 10970 | CKAP4 | | | | | | | | | | x | x | x | x |
| 136 | 51143 | DYNC1LI1 | | | | | | | | | | x | x | x | x |
| 143 | 23360 | FNBP4 | | | | | | | | | | x | x | x | x |
| 163 | 4688 | NCF2 | | | | | | | | | | x | x | x | x |
| 169 | 29982 | NRBF2 | | | | | | | | | | x | x | x | x |
| 171 | 4926 | NUMA1 | | | | | | | | | | x | x | x | x |
| 188 | 644096 | SDHAF1 | | | | | | | | | | x | x | x | x |
| 348 | 56674 | TMEM9B | | | | | | | | | | x | x | x | x |
| 370 | 38 | ACAT1 | | | | | | | | | | x | x | x | x |
| 371 | 684 | BST2 | | | | | | | | | | x | x | x | x |
| 372 | 1058 | CENPA | | | | | | | | | | x | x | x | x |
| 373 | 1665 | DHX15 | | | | | | | | | | x | x | x | x |
| 374 | 3092 | HIP1 | | | | | | | | | | x | x | x | x |
| 375 | 3336 | HSPE1 | | | | | | | | | | x | x | x | x |
| 376 | 5455 | POU3F3 | | | | | | | | | | x | x | x | x |
| 377 | 5918 | RARRES1 | | | | | | | | | | x | x | x | x |
| 378 | 6136 | RPL12 | | | | | | | | | | x | x | x | x |
| 379 | 6626 | SNRPA | | | | | | | | | | x | x | x | x |
| 380 | 6631 | SNRPC | | | | | | | | | | x | x | x | x |
| 381 | 6757 | SSX2 | | | | | | | | | | x | x | x | x |
| 382 | 9788 | MTSS1 | | | | | | | | | | x | x | x | x |
| 383 | 10134 | BCAP31 | | | | | | | | | | x | x | x | x |
| 384 | 10522 | DEAF1 | | | | | | | | | | x | x | x | x |
| 385 | 10633 | RASL10A | | | | | | | | | | x | x | x | x |
| 386 | 54795 | TRPM4 | | | | | | | | | | x | x | x | x |
| 387 | 54913 | RPP25 | | | | | | | | | | x | x | x | x |
| 388 | 54994 | C20orf11 | | | | | | | | | | x | x | x | x |
| 389 | 55727 | BTBD7 | | | | | | | | | | x | x | x | x |
| 390 | 79140 | CCDC28B | | | | | | | | | | x | x | x | x |
| 391 | 79613 | TMCO7 | | | | | | | | | | x | x | x | x |
| 423 | 972 | CD74 | | | | | | | | | | x | x | x | x |
| 424 | 1397 | CRIP2 | | | | | | | | | | x | x | x | x |
| 425 | 2040 | STOM | | | | | | | | | | x | x | x | x |
| 426 | 2316 | FLNA | | | | | | | | | | x | x | x | x |
| 427 | 4000 | LMNA | | | | | | | | | | x | x | x | x |
| 428 | 4582 | MUC1 | | | | | | | | | | x | x | x | x |
| 429 | 5230 | PGK1 | | | | | | | | | | x | x | x | x |
| 430 | 5340 | PLG | | | | | | | | | | x | x | x | x |
| 431 | 6525 | SMTN | | | | | | | | | | x | x | x | x |
| 432 | 8936 | WASF1 | | | | | | | | | | x | x | x | x |
| 433 | 23647 | ARFIP2 | | | | | | | | | | x | x | x | x |
| 3 | 7430 | EZR | | | x | x | x | x | x | | | | x | x | x |
| 11 | 30011 | SH3KBP1 | | | | | | | x | | | | x | x | x |
| 14 | 6638 | SNRPN | x | x | | x | | x | | | | | x | x | x |
| 16 | 6710 | SPTB | | | | x | | x | | | | | x | x | x |

TABLE 8-continued

Combinations of antigens from Table 2:

| Seq. ID Nr | GeneID | Gene Symbol | Panel ENA-4 | +anti-rib | Panel PI | Panel PII | Panel PIII | Panel PIV | Panel PV | Panel VI | Panel VII | Panel VIII | Panel IX | Panel X* | Panel XI* |
|---|---|---|---|---|---|---|---|---|---|---|---|---|---|---|---|
| 33 | 55802 | DCP1A | | | | | | | | | | | x | x | x |
| 41 | 54531 | MIER2 | | | | | | | | | | | x | x | x |
| 48 | 11040 | PIM2 | | | | | | | | | | | x | x | x |
| 74 | 10933 | MORF4L1 | | | | | | | | | | | x | x | x |
| 105 | 8615 | USO1 | | | | | | | | | | | x | x | x |
| 108 | 375690 | WASH5P | | | | | | | | | | | x | x | x |
| 114 | 55256 | ADI1 | | | | | | | | | | | x | x | x |
| 115 | 9255 | AIMP1 | | | | | | | | | | | x | x | x |
| 116 | 54522 | ANKRD16 | | | | | | | | | | | x | x | x |
| 132 | 8642 | DCHS1 | | | | | | | | | | | x | x | x |
| 140 | 100129583 | FAM47E | | | | | | | | | | | x | x | x |
| 145 | 64689 | GORASP1 | | | | | | | | | | | x | x | x |
| 152 | 23135 | KDM6B | | | | | | | | | | | x | x | x |
| 166 | 22861 | NLRP1 | | | | | | | | | | | x | x | x |
| 170 | 8439 | NSMAF | | | | | | | | | | | x | x | x |
| 174 | 5195 | PEX14 | | | | | | | | | | | x | x | x |
| 186 | 8578 | SCARF1 | | | | | | | | | | | x | x | x |
| 191 | 6421 | SFPQ | | | | | | | | | | | x | x | x |
| 197 | 54961 | SSH3 | | | | | | | | | | | x | x | x |
| 202 | 90326 | THAP3 | | | | | | | | | | | x | x | x |
| 255 | 55740 | ENAH | | | | | | | | | | | x | x | x |
| 263 | 150946 | FAM59B | | | | | | | | | | | x | x | x |
| 277 | 3304 | HSPA1B | | | | | | | | | | | x | x | x |
| 292 | 4137 | MAPT | | | | | | | | | | | x | x | x |
| 331 | 4736 | RPL10A | | | | | | | | | | | x | x | x |
| 343 | 23345 | SYNE1 | | | | | | | | | | | x | x | x |
| 350 | 10155 | TRIM28 | | | | | | | | | | | x | x | x |
| 358 | 65109 | UPF3B | | | | | | | | | | | x | x | x |
| 392 | 5504 | PPP1R2 | | | | | | | | | | | x | x | x |
| 393 | 8349 | HIST2H2BE | | | | | | | | | | | x | x | x |
| 394 | 11168 | PSIP1 | | | | | | | | | | | x | x | x |
| 395 | 149986 | LSM14B | | | | | | | | | | | x | x | x |
| 434 | 6712 | SPTBN2 | | | | | | | | | | | x | x | x |
| 435 | 6729 | SRP54 | | | | | | | | | | | x | x | x |
| 436 | 9987 | HNRPDL | | | | | | | | | | | x | x | x |

*The panels X and XI can be supplemented by 20 or more markers from the other available 1587 markers, in particular proteins.

Panel VI comprises 11 antigens which were measured in all three SLE cohorts with a p-value <0.05.

Panel VII comprises 19 antigens which were measured in the three SLE cohorts with a p-value <0.05.

Panel VIII comprises panel VII and a further 52 antigens which were found in cohort 3 and at least one of the other SLE cohorts with a p-value <0.05 for the comparison of SLE against healthy controls.

Panel IX comprises panel VII, panel VIII and a further 110 antigens which, in one or two SLE cohorts for the comparison of SLE against healthy controls, achieved a p-value of 0.05.

Panel X comprises panel VII, panel VIII, panel IX and a further 227 antigens which, as specified in Table 2, originate from different comparisons and achieved a p-value <0.05 in at least one SLE cohort.

Tables 9a, 9c and 9e show the area under the curve (AUC) confidence interval, sensitivity and specificity of different biomarker combinations in the three different SLE cohorts.

Tables 9b and 9d show the area under the curve (AUC), confidence interval, sensitivity and specificity of the different panels in the three SLE cohorts in combination with anti-dsDNA autoantibodies.

TABLE 9a

Area under the curve (AUC), sensitivity and specificity of the different panels in the SLE cohort I.

| Cohort I Panel | AUC | | | Sensitivity | | | Specificity | | |
|---|---|---|---|---|---|---|---|---|---|
| | mean | lower CI | upper CI | mean | lower CI | upper CI | mean | lower CI | upper CI |
| PI | 0.86 | 0.84 | 0.87 | 0.79 | 0.76 | 0.81 | 0.84 | 0.82 | 0.86 |
| PII | 0.88 | 0.87 | 0.90 | 0.81 | 0.79 | 0.84 | 0.82 | 0.80 | 0.85 |
| PIII | 0.84 | 0.83 | 0.86 | 0.74 | 0.71 | 0.76 | 0.80 | 0.77 | 0.83 |
| PIV | 0.85 | 0.84 | 0.87 | 0.80 | 0.77 | 0.82 | 0.83 | 0.81 | 0.85 |
| PV | 0.81 | 0.79 | 0.83 | 0.73 | 0.70 | 0.75 | 0.76 | 0.73 | 0.79 |
| PVI | 0.87 | 0.86 | 0.89 | 0.79 | 0.77 | 0.82 | 0.83 | 0.81 | 0.85 |
| Panel.ENA | 0.87 | 0.85 | 0.88 | 0.73 | 0.71 | 0.76 | 0.86 | 0.84 | 0.89 |
| Panel.ENA + antiRib | 0.87 | 0.85 | 0.88 | 0.78 | 0.75 | 0.80 | 0.83 | 0.81 | 0.85 |
| PVII | 0.79 | 0.77 | 0.81 | 0.75 | 0.72 | 0.78 | 0.77 | 0.74 | 0.79 |

TABLE 9a-continued

Area under the curve (AUC), sensitivity and specificity of the different panels in the SLE cohort I.

| Cohort I Panel | AUC mean | lower CI | upper CI | Sensitivity mean | lower CI | upper CI | Specificity mean | lower CI | upper CI |
|---|---|---|---|---|---|---|---|---|---|
| PVIII | 0.85 | 0.83 | 0.86 | 0.75 | 0.72 | 0.78 | 0.82 | 0.79 | 0.84 |
| PIX | 0.83 | 0.81 | 0.84 | 0.73 | 0.71 | 0.76 | 0.81 | 0.78 | 0.83 |
| PX | 0.83 | 0.81 | 0.84 | 0.73 | 0.70 | 0.76 | 0.78 | 0.76 | 0.81 |
| PXI | 0.83 | 0.81 | 0.84 | 0.74 | 0.71 | 0.76 | 0.79 | 0.76 | 0.81 |

TABLE 9b

Area under the curve (AUC), upper and lower confidence interval (CI), sensitivity and specificity of the biomarker panels in SLE cohort I in combination with anti-dsDNA autoantibodies.

| Cohort I Panel plus dsDNA | AUC mean | lower CI | upper CI | Sensitivity mean | lower CI | upper CI | Specificity mean | lower CI | upper CI |
|---|---|---|---|---|---|---|---|---|---|
| PI | 0.86 | 0.84 | 0.87 | 0.79 | 0.77 | 0.81 | 0.83 | 0.81 | 0.85 |
| PII | 0.87 | 0.85 | 0.88 | 0.80 | 0.77 | 0.82 | 0.81 | 0.79 | 0.83 |
| PIII | 0.83 | 0.81 | 0.85 | 0.74 | 0.71 | 0.77 | 0.78 | 0.76 | 0.81 |
| PIV | 0.86 | 0.84 | 0.87 | 0.79 | 0.76 | 0.82 | 0.83 | 0.81 | 0.85 |
| PV | 0.80 | 0.78 | 0.82 | 0.72 | 0.70 | 0.75 | 0.76 | 0.73 | 0.78 |
| PVI | 0.86 | 0.85 | 0.88 | 0.79 | 0.77 | 0.82 | 0.82 | 0.80 | 0.85 |
| Panel.ENA | 0.86 | 0.85 | 0.88 | 0.73 | 0.71 | 0.76 | 0.86 | 0.84 | 0.89 |
| Panel.ENA + antiRib | 0.86 | 0.85 | 0.88 | 0.76 | 0.74 | 0.78 | 0.83 | 0.80 | 0.85 |
| PVII | 0.79 | 0.77 | 0.81 | 0.74 | 0.71 | 0.77 | 0.76 | 0.73 | 0.78 |
| PVIII | 0.89 | 0.88 | 0.90 | 0.80 | 0.78 | 0.83 | 0.85 | 0.83 | 0.87 |
| PIX | 0.90 | 0.89 | 0.92 | 0.81 | 0.79 | 0.83 | 0.85 | 0.83 | 0.87 |
| PX | 0.84 | 0.82 | 0.86 | 0.73 | 0.70 | 0.75 | 0.81 | 0.79 | 0.84 |
| PXI | 0.89 | 0.88 | 0.90 | 0.81 | 0.78 | 0.83 | 0.84 | 0.82 | 0.86 |

TABLE 9c

Area under the curve (AUC), shows the sensitivity and specificity of the different panels in the SLE cohort II.

| Cohort II Panel | AUC mean | lower CI | upper CI | Sensitivity mean | lower CI | upper CI | Specificity mean | lower CI | upper CI |
|---|---|---|---|---|---|---|---|---|---|
| PI | 0.84 | 0.83 | 0.86 | 0.74 | 0.72 | 0.76 | 0.79 | 0.77 | 0.81 |
| PII | 0.78 | 0.77 | 0.80 | 0.68 | 0.65 | 0.70 | 0.72 | 0.70 | 0.75 |
| PIII | 0.83 | 0.81 | 0.84 | 0.73 | 0.70 | 0.75 | 0.78 | 0.76 | 0.81 |
| PIV | 0.86 | 0.84 | 0.87 | 0.76 | 0.74 | 0.78 | 0.81 | 0.79 | 0.84 |
| PV | 0.77 | 0.75 | 0.78 | 0.67 | 0.65 | 0.69 | 0.74 | 0.72 | 0.76 |
| PVI | 0.87 | 0.86 | 0.88 | 0.77 | 0.74 | 0.79 | 0.82 | 0.80 | 0.84 |
| Panel.ENA | 0.76 | 0.74 | 0.77 | 0.59 | 0.56 | 0.61 | 0.78 | 0.75 | 0.80 |
| Panel.ENA + antiRib | 0.84 | 0.83 | 0.86 | 0.73 | 0.71 | 0.76 | 0.83 | 0.82 | 0.85 |
| PVII | 0.84 | 0.82 | 0.86 | 0.76 | 0.74 | 0.78 | 0.80 | 0.77 | 0.82 |
| PVIII | 0.85 | 0.83 | 0.86 | 0.76 | 0.74 | 0.78 | 0.80 | 0.78 | 0.82 |
| PIX | 0.84 | 0.83 | 0.86 | 0.76 | 0.74 | 0.78 | 0.79 | 0.77 | 0.81 |
| PX | 0.83 | 0.81 | 0.85 | 0.76 | 0.73 | 0.78 | 0.78 | 0.76 | 0.80 |
| PXI | 0.82 | 0.81 | 0.84 | 0.74 | 0.71 | 0.76 | 0.79 | 0.76 | 0.81 |

TABLE 9d

Area under the curve (AUC), sensitivity and specificity of the different panels in SLE cohort II in combination with anti-dsDNA autoantibodies.

| Cohort II Panel plus dsDNA | AUC mean | lower CI | upper CI | Sensitivity mean | lower CI | upper CI | Specificity mean | lower CI | upper CI |
|---|---|---|---|---|---|---|---|---|---|
| PI | 0.84 | 0.82 | 0.85 | 0.73 | 0.71 | 0.76 | 0.78 | 0.76 | 0.81 |
| PII | 0.78 | 0.76 | 0.80 | 0.67 | 0.65 | 0.70 | 0.73 | 0.70 | 0.75 |
| PIII | 0.82 | 0.81 | 0.84 | 0.73 | 0.71 | 0.75 | 0.76 | 0.74 | 0.79 |
| PIV | 0.85 | 0.84 | 0.87 | 0.76 | 0.73 | 0.78 | 0.80 | 0.78 | 0.83 |
| PV | 0.77 | 0.75 | 0.78 | 0.67 | 0.65 | 0.69 | 0.71 | 0.69 | 0.74 |
| PVI | 0.87 | 0.85 | 0.88 | 0.77 | 0.75 | 0.79 | 0.82 | 0.80 | 0.84 |
| Panel.ENA | 0.77 | 0.76 | 0.79 | 0.60 | 0.58 | 0.63 | 0.77 | 0.75 | 0.80 |
| Panel.ENA + antiRib | 0.85 | 0.84 | 0.86 | 0.73 | 0.71 | 0.76 | 0.83 | 0.81 | 0.85 |
| PVII | 0.84 | 0.82 | 0.85 | 0.75 | 0.73 | 0.78 | 0.79 | 0.77 | 0.82 |
| PVIII | 0.85 | 0.83 | 0.86 | 0.72 | 0.70 | 0.75 | 0.83 | 0.80 | 0.85 |
| PIX | 0.78 | 0.77 | 0.80 | 0.64 | 0.62 | 0.67 | 0.78 | 0.75 | 0.80 |
| PX | 0.84 | 0.83 | 0.85 | 0.72 | 0.70 | 0.75 | 0.83 | 0.81 | 0.85 |
| PXI | 0.87 | 0.85 | 0.88 | 0.75 | 0.73 | 0.77 | 0.84 | 0.82 | 0.86 |

TABLE 9e

Area under the curve (AUC), sensitivity and specificity of the different panels in the SLE cohort III.

| Cohort III Panel | AUC mean | lower CI | upper CI | Sensitivity mean | lower CI | upper CI | Specificity mean | lower CI | upper CI |
|---|---|---|---|---|---|---|---|---|---|
| PI | 0.83 | 0.82 | 0.84 | 0.71 | 0.69 | 0.73 | 0.80 | 0.78 | 0.81 |
| PII | 0.82 | 0.81 | 0.84 | 0.71 | 0.69 | 0.72 | 0.80 | 0.79 | 0.81 |
| PIII | 0.79 | 0.78 | 0.80 | 0.65 | 0.63 | 0.67 | 0.76 | 0.74 | 0.78 |
| PIV | 0.82 | 0.81 | 0.83 | 0.71 | 0.69 | 0.73 | 0.79 | 0.78 | 0.81 |
| PV | 0.77 | 0.76 | 0.78 | 0.66 | 0.64 | 0.67 | 0.76 | 0.74 | 0.78 |
| PVI | 0.84 | 0.83 | 0.85 | 0.71 | 0.70 | 0.73 | 0.81 | 0.79 | 0.82 |
| Panel.ENA | 0.78 | 0.77 | 0.80 | 0.65 | 0.63 | 0.67 | 0.82 | 0.81 | 0.84 |
| Panel.ENA + antiRib | 0.79 | 0.78 | 0.80 | 0.67 | 0.66 | 0.69 | 0.83 | 0.82 | 0.85 |
| PVII | 0.83 | 0.82 | 0.84 | 0.72 | 0.71 | 0.74 | 0.79 | 0.77 | 0.81 |
| PVIII | 0.83 | 0.82 | 0.84 | 0.73 | 0.72 | 0.75 | 0.77 | 0.76 | 0.79 |
| PIX | 0.81 | 0.79 | 0.82 | 0.72 | 0.70 | 0.74 | 0.76 | 0.74 | 0.77 |
| PX | 0.79 | 0.78 | 0.81 | 0.73 | 0.71 | 0.75 | 0.76 | 0.74 | 0.78 |
| PXI | 0.78 | 0.77 | 0.80 | 0.70 | 0.69 | 0.72 | 0.75 | 0.73 | 0.77 |

FIG. 11: The figure shows the comparison of the calculated p-values and autoantibody frequencies (% positive classified observations) for the antigens from Table 2 in the three SLE cohorts. The antigens are illustrated as circles with the consecutive number. The horizontal line marks the threshold value of p<0.05 for the comparison of SLE compared with healthy controls.

LITERATURE

Li P H, Wong W H, Lee T L, Lau C S, Chan T M, Leung A M, Tong K L, Tse N K, Mok C C, Wong S N, Lee K W, Ho M H, Lee P P, Chong C Y, Wong R W, Mok M Y, Ying S K, Fung S K, Lai W M, Yang W, Lau Y L. Relationship between autoantibody clustering and clinical subsets in SLE: cluster and association analyses in Hong Kong Chinese. Rheumatology (Oxford). 2013 February; 52(2): 337-45. doi: 10.1093/rheumatology/kes261. Epub 2012 Oct. 4. PubMed PMID: 23038697.

Liu C C, Kao A H, Manzi S, Ahearn J M. Biomarkers in systemic lupus erythematosus: challenges and prospects for the future. Ther Adv Musculoskelet Dis. 2013 August; 5(4):210-33.

Ching K H, Burbelo P D, Tipton C, Wei C, Petri M, Sanz I, Iadarola M J. Two major autoantibody clusters in systemic lupus erythematosus. PLoS One. 2012; 7(2): e32001. doi: 10.1371/journal.pone.0032001. Epub 2012 Feb. 21. PubMed PMID: 22363785; PubMed Central PMCID: PMC3283706.

Stohl W. Future prospects in biologic therapy for systemic lupus erythematosus. Nat Rev Rheumatol. 2013 Sep. 10. doi: 10.1038/nrrheum.2013.136. [Epub ahead of print] PubMed PMID: 24018550.

Thanou A, Merrill J T. Treatment of systemic lupus erythematosus: new therapeutic avenues and blind alleys. Nat Rev Rheumatol. 2013 Oct. 8. doi:10.1038/nrrheum.2013.145. [Epub ahead of print] PubMed PMID: 24100460.

Sherer Y, Gorstein A, Fritzler M J, Shoenfeld Y. Autoantibody explosion in systemic lupus erythematosus: more than 100 different antibodies found in SLE patients. Semin Arthritis Rheum. 2004 October; 34(2):501-37. Review. PubMed PMID: 15505768.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10746735B2). An electronic copy of the "Sequence Listing" will also be available from the USPTO upon request and payment of the fee set forth in 37 CFR 1.19(b)(3).

The invention claimed is:

1. A method for identifying markers for systemic lupus erythematosus (SLE), comprising:
   a) bringing serum samples of SLE patients into contact with more than 5000 antigens coupled to beads, measuring the binding of each individual antigen to autoantibodies in the serum samples of the SLE patients using an immunofluorescence assay, and determining the median fluorescence intensity (MFI) for each individual antigen;
   b) bringing serum samples of patients with rheumatoid arthritis (RA) into contact with the more than 5000 antigens coupled to beads, measuring the binding of each individual antigen to autoantibodies in the serum samples of the RA patients using said immunofluorescence assay, and determining from this—the median fluorescence intensity (MFI) for each individual antigen;
   c) bringing serum samples of healthy individuals into contact with the more than 5000 antigens coupled to beads, measuring the binding of each individual antigen to autoantibodies in the serum samples of the healthy individuals using said immunofluorescence assay, and determining the median fluorescence intensity (MFI) for each individual antigen;
   d) statistically evaluating the MFI for each individual antigen obtained from a), b), and c) using a univariate analysis and identifying marker candidate antigens with which SLE patients can be differentiated from RA patients and from healthy individuals;
   e) bringing serum samples of patients with early RA into contact with the marker candidate antigens identified in d) coupled to beads, measuring the binding of each individual marker candidate antigens to autoantibodies in the serum samples of patients with early RA using said immunofluorescence assay, and determining the median fluorescence intensity (MFI) for each individual marker candidate antigen;
   f) bringing serum samples of patients with systemic sclerosis (SSc) into contact with the marker candidate antigens identified in d) coupled to beads, measuring the binding of each marker candidate antigen to autoantibodies in the serum samples of SSc patients using said immunofluorescence assay, and determining the median fluorescence intensity (MFI) for each individual marker candidate antigen;
   g) bringing serum samples of patients with ankylosing spondylitis or Bekhterev's disease (SPA) into contact with the marker candidate antigens identified in d) coupled to beads, measuring the binding of each marker candidate antigen to autoantibodies in the serum samples of SPA patients using said immunofluorescence assay, and determining the median fluorescence intensity (MFI) for each individual marker candidate antigen;
   h) statistically evaluating the MFI for each individual marker candidate antigen obtained from e), f), and g) using an univariate analysis and identifying a marker for SLE when a threshold value of 3 standard deviations above the mean value of the healthy samples is not reached; and
   i) identifying a SLE patient for stratification and administering at least one therapeutic agent to the SLE patient for treatment or monitoring the SLE patient for control of the SLE patient's therapy;
      wherein the marker for SLE is selected from the sequences of SEQ ID NO: 1-11, 13, 15, 16, 18, 19, 20-24, 28, 29, 31, 46, 61, 95, 126, 128, 134, 136, 143, 152, 163, 169, 171, 173, 188, 191, 213, 214, 241, 258, 270, 302, 348, 349, 367-370, 372-375, 378-391, 403, 406, 408, 415, and 423-433.

2. The method of claim 1 for identifying markers for SLE, comprising selecting a marker for SLE which, in the univariate analysis, has an adjusted p-value for the non-parametric mean value comparison between the groups of less than 0.05 and at the same time have a fold change of greater than 1.5 and an AUC resulting from the ROC analysis of greater than 0.75.

3. The method of claim 1, wherein the marker for SLE is selected from proteins encoded by SEQ ID NO: 1-11, 13, 15, 16, 18, 19, 20-24, 28, 29, 31, 46, 61, 95, 126, 128, 134, 136, 143, 152, 163, 169, 171, 173, 188, 191, 213, 214, 241, 258, 270, 302, 348, 349, 367-370, 372-375, 378-391, 403, 406, 408, 415, and 423-433.

4. The method of claim 2, wherein the marker for SLE is selected from proteins encoded by SEQ ID NO: 1-11, 13, 15, 16, 18, 19, 20-24, 28, 29, 31, 46, 61, 95, 126, 128, 134, 136, 143, 152, 163, 169, 171, 173, 188, 191, 213, 214, 241, 258, 270, 302, 348, 349, 367-370, 372-375, 378-391, 403, 406, 408, 415, and 423-433.

* * * * *

UNITED STATES PATENT AND TRADEMARK OFFICE
CERTIFICATE OF CORRECTION

Page 1 of 1

PATENT NO. : 10,746,735 B2
APPLICATION NO. : 15/117508
DATED : August 18, 2020
INVENTOR(S) : Angelika Lüking et al.

It is certified that error appears in the above-identified patent and that said Letters Patent is hereby corrected as shown below:

On the Title Page

Item (30), in the Foreign Application Priority Data:
Line 1, "14154557" should read --14154557.4--; and
Line 2, "14178090" should read --14178090.8--.

In the Claims

In Claim 1, Column 87, Line 29, "from this—the median" should read --from this the median--.

In Claim 1, Column 88, Line 26, "an univariate analysis" should read --a univariate analysis--.

In Claim 1, Column 88, Line 30, "a SLE patient" should read --an SLE patient--.

In Claim 2, Column 88, Line 44, "have a fold change" should read --has a fold change--.

Signed and Sealed this
Second Day of February, 2021

Drew Hirshfeld
*Performing the Functions and Duties of the
Under Secretary of Commerce for Intellectual Property and
Director of the United States Patent and Trademark Office*